(12) United States Patent
Koppitz et al.

(10) Patent No.: US 9,512,126 B2
(45) Date of Patent: Dec. 6, 2016

(54) SUBSTITUTED IMIDAZOPYRIDAZINES

(71) Applicants: Bayer Intellectual Property GmbH, Monheim (DE); BAYER PHARMA AKTIENGESELLSCHAFT, Berlin (DE)

(72) Inventors: Marcus Koppitz, Berlin (DE); Ulrich Klar, Berlin (DE); Antje Margret Wengner, Berlin (DE); Roland Neuhaus, Berlin (DE); Gerhard Siemeister, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/384,828

(22) PCT Filed: Mar. 11, 2013

(86) PCT No.: PCT/EP2013/054841
§ 371 (c)(1),
(2) Date: Sep. 12, 2014

(87) PCT Pub. No.: WO2013/135612
PCT Pub. Date: Sep. 19, 2013

(65) Prior Publication Data
US 2015/0104526 A1 Apr. 16, 2015

(30) Foreign Application Priority Data

Mar. 14, 2012 (EP) .................................. 12159455
Feb. 6, 2013 (EP) .................................. 13154139

(51) Int. Cl.
*A01N 43/00* (2006.01)
*A61K 31/33* (2006.01)
*C07D 487/00* (2006.01)
*C07D 487/04* (2006.01)
*A61K 31/5025* (2006.01)
*A61K 45/06* (2006.01)

(52) U.S. Cl.
CPC ......... *C07D 487/04* (2013.01); *A61K 31/5025* (2013.01); *A61K 45/06* (2013.01)

(58) Field of Classification Search
USPC .......................................... 514/183; 544/236
See application file for complete search history.

(56) References Cited

U.S. PATENT DOCUMENTS

| | | | |
|---|---|---|---|
| 6,514,989 | B1 | 2/2003 | Nettekoven et al. |
| 9,199,999 | B2 | 12/2015 | Klar et al. |
| 9,212,184 | B2 | 12/2015 | Koppitz et al. |
| 9,255,100 | B2 | 2/2016 | Klar et al. |
| 9,284,317 | B2 | 3/2016 | Koppitz et al. |
| 2008/0021059 | A1 | 1/2008 | Butler et al. |
| 2008/0045536 | A1 | 2/2008 | Vaccaro et al. |
| 2008/0090818 | A1 | 4/2008 | Andrews et al. |
| 2012/0059162 | A1 | 3/2012 | Kusakabe et al. |
| 2012/0238565 | A1 | 9/2012 | Swinnen et al. |

FOREIGN PATENT DOCUMENTS

| | | |
|---|---|---|
| JP | 2004346016 A | 12/2004 |
| WO | 98/08847 A1 | 3/1998 |
| WO | 98/54158 A1 | 12/1998 |
| WO | 2004346016 A | 12/2004 |
| WO | 2005/030121 A2 | 4/2005 |
| WO | 2007/025090 A2 | 3/2007 |
| WO | 2007/038314 A2 | 4/2007 |
| WO | 2007/065010 A2 | 6/2007 |
| WO | 2008/021389 A2 | 2/2008 |
| WO | 2008/025821 A1 | 3/2008 |
| WO | 2008/141065 A1 | 11/2008 |
| WO | 2009/010530 A1 | 1/2009 |
| WO | 2009/021083 A1 | 2/2009 |
| WO | 2009/024824 A1 | 2/2009 |
| WO | 2009/027283 A1 | 3/2009 |
| WO | 2009/047514 A1 | 4/2009 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*

(Continued)

*Primary Examiner* — Marcos Sznaidman

(57) ABSTRACT

The present invention relates to substituted imidazopyridazine compounds of general formula I in which $R^3$, $R^5$ and A are as defined in the claims, to methods of preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

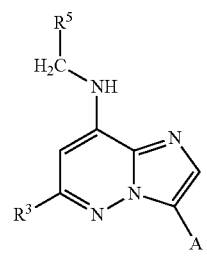

16 Claims, No Drawings

(56) References Cited

FOREIGN PATENT DOCUMENTS

| WO | 2009/068482 A1 | 6/2009 |
|---|---|---|
| WO | 2009/155121 A2 | 12/2009 |
| WO | 2010/042699 A1 | 4/2010 |
| WO | 2010/092015 A1 | 8/2010 |
| WO | 2010/092041 A1 | 8/2010 |
| WO | 2010/124826 A1 | 11/2010 |
| WO | 2011/013729 A1 | 2/2011 |
| WO | 2011/026579 A1 | 3/2011 |
| WO | 2011/063907 A1 | 6/2011 |
| WO | 2011/063908 A1 | 6/2011 |
| WO | 2011/064328 A1 | 6/2011 |
| WO | 2011/086098 A1 | 7/2011 |
| WO | 2011/086099 A1 | 7/2011 |
| WO | 2011/092272 A1 | 8/2011 |
| WO | 2012/032031 A1 | 3/2012 |
| WO | 2012/143329 A1 | 10/2012 |
| WO | 2013/135612 A1 | 9/2013 |

OTHER PUBLICATIONS

Gura et. al. (Science, 1997, 278:1041-1042).*
Johnson et. al. (British Journal of Cancer, 2001, 84:1424-1431).*
Dorer et. al. (Current Biology (2005) 15:1070-1076).*
Abrieu et al., "Mps1 Is a Kinetochore-Associated Kinase Essential for the Vertebrate Mitotic Checkpoint," Cell, Jul. 13, 2001, 106:83-93.
Berge et al., "Pharmaceutical Salts," Journal of Pharmaceutical Sciences, Jan. 1977, 66(1):1-19.
Dorer et al., "A Small-Molecule Inhibitor of Mps1 Blocks the Spindle-Checkpoint Responseto a Lack of Tension on Mitotic Chromosomes," Current Biology, Jun. 7, 2005, 15:1070-1076.
East et al., "DNA gyrase (GyrB)/topoisomerase IV (ParE) inhibitors: Synthesis and antibacterial activity," Bioorganic & Med. Chem. Letters, 2009, 19:894-899.
Fowler et al., "Selective Reduction of Radiotracer Trapping by Deuterium Substitution: Comparison of Carbon-I I-L-Deprenyl and Carbon-1 1-Deprenyl-D2 for MAO B Mapping," The Journal of Nuclear Medicine, 36(7):1255-1262.
Jelluma et al., "Chromosomal Instability by Inefficient Mps1 Auto-Activation Due to a Weakened Mitotic Checkpoint and Lagging Chromosomes," PloS One, Jun. 2008, 3(e2415):1-8.
Jones et al., "Chemical Genetics Reveals a Role for Mps1 Kinase in Kinetochore Attachment during Mitosis," Current Biology, Jan. 26, 2005, 15:160-165.
King, R., "When 2+2=5: The origins and fates of aneuploid and tetraploid cells," Biochimica et Biophysica Acta, 2008, 1786:4-14.
Kops et al., "On the Road to Cancer: Aneuploidy and the Mitotic Checkpoint," Nature Reviews/Cancer, Oct. 2005, 5:773-785.
Musacchio et al., "The spindle-assembly checkpoint in space and time," Nature Reviews/Molecular Cell Biology, May 2007, 8:379-393.
Schmidt et al., "Mitotic drug targets and the development of novel anti-mitotic anticancer drugs," Drug Resistance Updates, 2007, 10:162-181.
Schmidt et al., "Ablation of the spindle assembly checkpoint by a compound targeting Mps1," EMBO Reports, 2005, 5(9):866-872.
Schmidt et al., ""Exploiting the Compromised Spindle Assembly Checkpoint Functionof Tumor Cells,"" Cell Cycle, Jan. 2006, 5(2):159-163.
Suijkerbuijk et al., "Preventing aneuploidy: The contribution of mitotic checkpoint proteins," Biochimica et Biophysica Acta, 2008, 1786:24-31.
Weaver et al., "Aneuploidy: Instigator and Inhibitor of Tumorigenesis," Cancer Research, 2007, 67(21):10103-10105.
Yuan et al., "Increased Expression of Mitotic Checkpoint Genes in Breast Cancer Cells with Chromosomal Instability," Clinical Cancer Research, Jan. 15, 2006, 12(2):405-410.
Chemical Abstract XP-002574925.
Chemical Abstract XP-002574926.
Chemical Abstract XP-002574927.
Chemical Abstract XP-002574929.
Chemical Abstract XP-002574930.
Chemical Abstract XP-002574931.
Chemical Abstract XP-002574932.
Chemical Abstract XP-002574933.
Chemical Abstract XP-002574934.
Chemical Abstract XP-002574935.
Richardson et al., "Triazolo[1,5-a]pyrimidines as novel CDK2 inhibitors: Protein structure-guided design and SAR," Bioorganic & Medicinal Chemistry Letters, 2006, 16:1353-1357.
Zhao et al., "Synthesis and Anti-tumor Activities of Novel [1,2,4]triazolo[1,5-a]pyrimidines," Molecules, 2007, 1-2:1136-1146.
Related copending U.S. Appl. No. 13/512,721, filed Aug. 13, 2012.
Related copending U.S. Appl. No. 13/704,859, filed Feb. 25, 2013.
Related copending U.S. Appl. No. 14/113,017, filed Jan. 6, 2014.
Related copending U.S. Appl. No. 14/362,836, filed Jun. 4, 2014.
National Cancer Institute, "Non-Small Cell Lung Cancer Treatment (PDQ®)-Patient Version," Updated May 12, 2015.
Stucke et al., "Human Mps1 kinase is required for the spindle assembly checkpoint but not for centrosome duplication," The EMBO Journal, 2002, 21(7):1723-1732.
Strickley, R.G., "Parenteral Formulations of Small Molecules Therapeutics Marketed in the United States (1999)—Part I," PDA Journal of Pharmaceutical Science & Technology, Aug. 14, 2014, 53(6):324-349.
Cross et al., "IUPAC Commission on Nomenclature of Organic Chemistry—Rules for the Nomenclature of Organic Chemistry," International Union of Pure and Applied Chemistry, 1976, 45(1-B):12-30.
Nema et al., "Excipients and Their Use in Injectable Products," PDA Journal of Pharmaceutical Science & Technology, Jul.-Aug. 1997, 51(4):166-171.
Powell et al., "Compendium of Excipients for Parenteral Formulations," PDA Journal of Pharmaceutical Science & Technology, Sep.-Oct. 1998, 52(5):238-311.
Rautio et al., "Prodrugs: design and clinical applications," Nature Reviews | Drug Discovery, Mar. 2008, 7:255-270.
SoftFocus Library SFK 39, BioFocus DPI, publicly available Sep. 20, 2005.
Lopez et al., "Transdifferentiated Retinal Pigment Epithelial Cells Are Immunoreactive for Vascular Endothelial Growth Factor in Surgically Excised Age-Related Macular Degeneration-Related Choroidal Neovascular Membranes," Investigative Ophthalmology & Visual Science, Apr. 1996, 37(5): 855-868.
Pe'er et al., "Hypoxia-Induced Expression of Vascular Endothelial Growth Factor by Retinal Cells is a Common Factor in Neovascularizing Ocular Diseases," Laboratory Investigation, 72(6, 19):638-645.
Related co-pending U.S. Appl. No. 13/635,734, filed Apr. 2, 2013.
Related co-pending U.S. Appl. No. 14/110,105, filed May 22, 2014.
Related co-pending U.S. Appl. No. 14/384,828, filed Sep. 12, 2014.
Related co-pending U.S. Appl. No. 14/771,648, filed Aug. 31, 2015.
Related co-pending U.S. Appl. No. 14/898,421, filed Dec. 14, 2015.

* cited by examiner

SUBSTITUTED IMIDAZOPYRIDAZINES

The present invention relates to substituted imidazopyridazine compounds of general formula I as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, TTK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumourigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81]. Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Established anti-mitotic drugs such as vinca alkaloids, taxanes or epothilones activate the SAC inducing a mitotic arrest either by stabilising or destabilising microtubule dynamics. This arrest prevents separation of sister chromatids to form the two daughter cells. Prolonged arrest in mitosis forces a cell either into mitotic exit without cytokinesis or into mitotic catastrophe leading to cell death.

In contrast, inhibitors of Mps-1 induce a SAC inactivation that accelerates progression of cells through mitosis resulting in severe chromosomal missegregation and finally in cell death.

These findings suggest that Mps-1 inhibitors should be of therapeutic value for the treatment of proliferative disorders associated with enhanced uncontrolled proliferative cellular processes such as, for example, cancer, inflammation, arthritis, viral diseases, neurodegenerative diseases such as Alzheimer's disease, cardiovascular diseases, or fungal diseases in a warm-blooded animal such as man.

Therefore, inhibitors of Mps-1 represent valuable compounds that should complement therapeutic options either as single agents or in combination with other drugs.

Different compounds have been disclosed in prior art which show an inhibitory effect on Mps-1 kinase. WO2010124826A1 discloses substituted imidazoquinoxaline compounds as inhibitors of Mps-1 kinase or TTK. WO2011026579A1 discloses substituted aminoquinoxalines as Mps-1 inhibitors. WO2011063908A1, WO2011064328A1 as well as WO2011063907 A1 disclose triazolopyridine derivates as inhibitors of Mps-1 kinase.

Imidazopyridazine derivates have been disclosed for the treatment or prophylaxis of different diseases:

WO 2007038314 A2 relates to fused heterocyclic compounds useful as kinase modulators, including MK2 modulation. In particular, WO 2007038314 A2 relates to imidazo[1,2-b]pyridazines.

US patent application publication US 20080045536 A1 similarly relates to fused heterocyclic compounds useful as kinase modulators, including MK2 modulation. In particular, it relates to imidazo[1,2-b]pyridazines.

WO 2010042699 A1 relates to fused heterocyclic compounds useful as kinase modulators, particularly CK2 modulation. In particular, WO 2010042699 A1 relates to imidazo[1,2-b]pyridazines which are substituted with a nitrite group in position 3.

WO 2007025090 A2 relates to heterocyclic compounds useful as inhibitors of MEK kinase. In particular, WO 2007025090 A2 relates inter alia to imidazo[1,2-b] pyridazines.

WO 199808847 A1 relates to heterocyclic compounds useful as corticotropin releasing factor (hormone) CRF (CRH) antagonists. In particular, WO 199808847 A1 relates inter alia to imidazo[1,2-b]pyridazines.

WO 2011013729A1 discloses fused imidazole derivatives as Mps-1 inhibitors. Among the disclosed fused imidazole derivates there are also imidazo[1,2-b]pyridazines. For example, WO 2011013729A1 discloses compounds of formula C1:

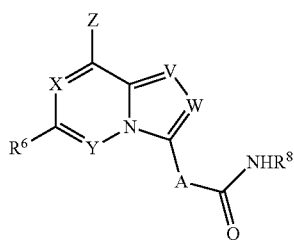

in which (X, Y, V, W) is (—N═, ═CR¹—, ═N—, —CR⁷═), (—CR²═, ═N—, ═N—, —CR⁷═), (—N═, ═CR¹—, ═N—, —N═) or (—N═, ═CR¹—, —O—, —N═);

R⁸ is substituted or unsubstituted cycloalkyl;

Z is a group represented by formula —NR³R⁴ or a group represented by formula —OR⁵;

A is substituted or unsubstituted aromatic hydrocarbon ring, substituted or unsubstituted aromatic heterocyclic ring, substituted or unsubstituted non-aromatic hydrocarbon ring or substituted or unsubstituted non-aromatic heterocyclic ring;

R¹, R³, R⁴, R⁵, and R⁶ represent a large variety of substituents (see WO 2011013729A1, e.g. claim 1).

However, WO 2011013729A1 does not specifically disclose anyone of the compounds of the present invention.

WO 2012032031A1 inter alia is related to Mps-1 inhibitors of formula C2:

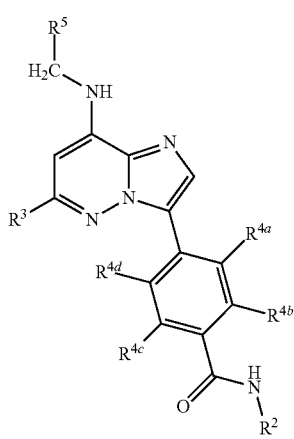

The PCT application contains the following three compounds in which R³ is a benzyl group with a substituted phenyl:

Surprisingly it was found that the metabolic stability of such compounds is increased by substitution of at least one of the benzylic hydrogen atoms by a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group.

The inventors of the present invention surprisingly observed that compounds of general formula I as described and defined herein combine a high activity in Mps-1 inhibition with a high metabolic stability.

The state of the art described above does not specifically describe the imidazopyridazine compounds of claims 1 to 8, or a stereoisomer, a tautomer, an N-oxide, a hydrate, a solvate, or a salt thereof, or a mixture of same, as described and defined herein, and as hereinafter referred to as "compounds of the present invention", or their pharmacological activity and stability. It has now been found, and this constitutes the basis of the present invention, that said compounds of the present invention have surprising and advantageous properties.

In particular, said compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula I:

in which:
A represents wherein * indicates the point of attachment of said group with the rest of the molecule;

$R^2$ represents a methyl-, ethyl- or cyclopropyl- group;
wherein said methyl- or ethyl- group is optionally substituted, identically or differently, with 1, 2, 3 or 4 groups selected from: halogen, —OH, —CN, $C_1$-$C_3$-alkoxy-;
wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-;

$R^3$ represents
—C($R^{3a}$)($R^{3b}$)($R^{3c}$)
or
$R^3$ represents wherein * indicates the point of attachment of said group with the rest of the molecule;
$R^{3a}$, $R^{3b}$
represent, independently from each other, a hydrogen atom or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group;
or
$R^{3a}$, $R^{3b}$
together represent =O or =C($R^{3d}$)($R^{3e}$)
or
$R^{3a}$, $R^{3b}$
together with the carbon atom they are attached to, form a cyclopropyl- or cyclobutyl-ring;
wherein said cyclopropyl- or cyclobutyl-ring is optionally substituted, identically or differently, with 1 or 2 $R^{3d}$ groups;
$R^{3c}$ represents an aryl- or heteroaryl- group;
wherein said aryl- or heteroaryl- group is substituted, identically or differently, with 1, 2, 3 or 4 $R^7$ groups;
$R^{3d}$, $R^{3e}$
represent, independently from each other, a hydrogen atom or a $C_1$-$C_3$-alkyl- group;
$R^4$ represents a hydrogen atom, a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;
$R^5$ represents a hydrogen atom or a
$C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group;
wherein said $C_1$-$C_6$-alkyl-, —(CH$_2$)$_n$—$C_2$-$C_6$-alkenyl, —(CH$_2$)$_n$—$C_2$-$C_6$-alkynyl, —(CH$_2$)$_m$—$C_3$-$C_6$-cycloalkyl, —(CH$_2$)$_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group is optionally substituted, identically or differently, with 1, 2, 3, 4 or 5 $R^8$ groups;

$R^6$, $R^{6a}$, $R^{6b}$ represent, independently from each other, a hydrogen atom or a $C_1$-$C_6$-alkyl- group;

$R^7$ represents a halogen atom, or a hydroxy-, —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl- or halo-$C_1$-$C_6$-alkoxy-$C_1$-$C_6$-alkyl- group;

$R^8$ represents a hydrogen atom or a halogen atom or a —CN, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O$_2$)$R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;

wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;

n is an integer of 0, 1 or 2;

or a stereoisomer, a tautomer, an N-oxide, a hydrate, a solvate, or a salt thereof, or a mixture of same.

The present invention also relates to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically, or differently, i.e. one halogen atom being independent from another. Particularly, said halogen atom is F. Said halo-$C_1$-$C_6$-alkyl group is, for example, —CF$_3$, —CHF$_2$, —CH$_2$F, —CF$_2$CF$_3$, or —CH$_2$CF$_3$.

The term "$C_1$-$C_6$-alkoxy" is to be understood as preferably meaning a linear or branched, saturated, monovalent, hydrocarbon group of formula —O—$C_1$-$C_6$-alkyl, in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is/are replaced, in identically or differently, by one or more halogen atoms. Particularly, said halogen atom is F. Said halo-$C_1$-$C_6$-alkoxy group is, for example, —OCF$_3$, —OCHF$_2$, —OCH$_2$F, —OCF$_2$CF$_3$, or —OCH$_2$CF$_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically, or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is/are replaced, in identically or differently, by one or more halogen atoms. Particularly, said halogen atom is F. Said halo-$C_1$-$C_6$-alkoxy-$C_1$-$C_6$-alkyl group is, for example, —CH$_2$CH$_2$OCF$_3$, —CH$_2$CH$_2$OCHF$_2$, —CH$_2$CH$_2$OCH$_2$F, —CH$_2$CH$_2$OCF$_2$CF$_3$, or —CH$_2$CH$_2$OCH$_2$CF$_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1- dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_3$-$C_6$-cycloalkyl" is to be understood as meaning a saturated, monovalent, monocyclic hydrocarbon ring which contains 3, 4, 5 or 6 carbon atoms. Said $C_3$-$C_6$-cycloalkyl group is for example, a monocyclic hydrocarbon ring, e.g. a cyclopropyl, cyclobutyl, cyclopentyl, or cyclohexyl ring.

The term "3- to 7-membered heterocycloalkyl", is to be understood as meaning a saturated, monovalent, mono- or bicyclic hydrocarbon ring which contains 2, 3, 4, 5, or 6 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl- group; it being possible for said heterocycloalkyl group to be attached to the rest of the molecule via any one of the carbon atoms or, if present, a nitrogen atom.

Particularly, said 3- to 7-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In accordance with a first aspect, the present invention is directed to compounds of general formula I:

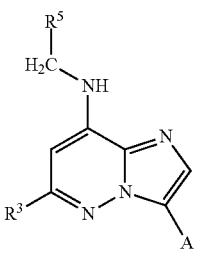

I in which:
A represents

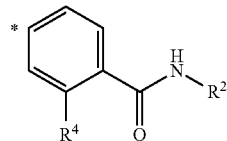

wherein * indicates the point of attachment of said group with the rest of the molecule;
$R^2$ represents a methyl-, ethyl- or cyclopropyl- group;
wherein said methyl- or ethyl- group is optionally substituted, identically or differently, with 1, 2, 3 or 4 groups selected from: halogen, —OH, —CN, $C_1$-$C_3$-alkoxy-;
wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-;
$R^3$ represents
—C($R^{3a}$)($R^{3b}$)($R^{3c}$)
or
$R^3$ represents

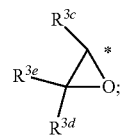

wherein * indicates the point of attachment of said group with the rest of the molecule;
$R^{3a}$, $R^{3b}$
represent, independently from each other, a hydrogen atom or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group;
or
$R^{3a}$, $R^{3b}$
together represent =O or =C($R^{3d}$)($R^{3e}$)
or
$R^{3a}$, $R^{3b}$
together with the carbon atom they are attached to, form a cyclopropyl- or cyclobutyl-ring;
wherein said cyclopropyl- or cyclobutyl-ring is optionally substituted, identically or differently, with 1 or 2 $R^{3d}$ groups;

$R^{3c}$ represents an aryl- or heteroaryl- group;
    wherein said aryl- or heteroaryl- group is substituted, identically or differently, with 1, 2, 3 or 4 $R^7$ groups;

$R^{3d}$, $R^{3e}$
    represent, independently from each other, a hydrogen atom or a $C_1$-$C_3$-alkyl- group;

$R^4$ represents a hydrogen atom, a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;

$R^5$ represents a hydrogen atom or a
    $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group;
    wherein said $C_1$-$C_6$-alkyl-, —$(CH_2)_n$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group is optionally substituted, identically or differently, with 1, 2, 3, 4 or 5 $R^8$ groups;

$R^6$, $R^{6a}$, $R^{6b}$
    represent, independently from each other, a hydrogen atom or a $C_1$-$C_6$-alkyl- group;

$R^7$ represents a halogen atom, or a hydroxy-, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl- group;

$R^8$ represents a hydrogen or halogen atom or a —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, 3- to 7-membered heterocycloalkyl-, aryl-, heteroaryl-, —C(=O)$R^6$, —C(=O)N(H)$R^{6a}$, —C(=O)N($R^{6a}$)$R^{6b}$, —C(=O)O—$R^6$, —N($R^{6a}$)$R^{6b}$, —NO$_2$, —N(H)C(=O)$R^6$, —N($R^{6c}$)C(=O)$R^6$, —N(H)C(=O)N($R^{6a}$)$R^{6b}$, —N($R^{6c}$)C(=O)N($R^{6a}$)$R^{6b}$, —N(H)C(=O)O$R^6$, —N($R^{6c}$)C(=O)O$R^6$, —N(H)S(=O)$R^6$, —N($R^{6c}$)S(=O)$R^6$, —N(H)S(=O)$_2$$R^6$, —N($R^{6c}$)S(=O)$_2$$R^6$, —N=S(=O)($R^{6a}$)$R^{6b}$, —O$R^6$, —O(C=O)$R^6$, —O(C=O)N($R^{6a}$)$R^{6b}$, —O(C=O)O$R^6$, —S$R^6$, —S(=O)$R^6$, —S(=O)N(H)$R^6$, —S(=O)N($R^{6a}$)$R^{6b}$, —S(=O$_2$)$R^6$, —S(=O)$_2$N(H)$R^6$, —S(=O)$_2$N($R^{6a}$)$R^{6b}$, —S(=O)(=N$R^{6c}$)$R^6$ or —S(=O)$_2$-(3- to 7-membered heterocycloalkyl) group;
    wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2; and
n is an integer of 0, 1 or 2.

In a preferred embodiment, the invention relates to compounds of formula I, supra, wherein A represents a group selected from:

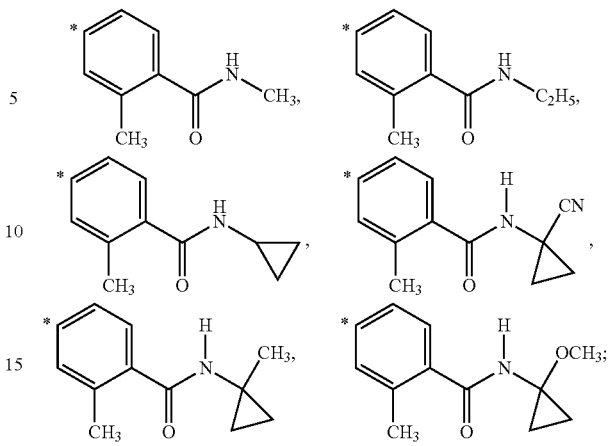

wherein * indicates the point of attachment of said groups with the rest of the molecule.

Preferably, A represents

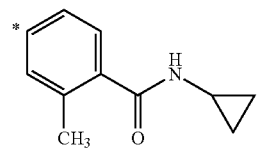

wherein * indicates the point of attachment of said group with the rest of the molecule.

In another preferred embodiment, the invention relates to compounds of formula I, supra, wherein $R^2$ represents a methyl- or ethyl- group; wherein said methyl- or ethyl- group is optionally substituted, identically or differently, with 1, 2, 3 or 4 groups selected from: halogen, —OH, —CN, $C_1$-$C_3$-alkoxy-.

In another preferred embodiment, the invention relates to compounds of formula I, supra, wherein $R^2$ represents a methyl- or ethyl- group.

In another preferred embodiment, the invention relates to compounds of formula I, supra, wherein $R^2$ represents a cyclopropyl- group; wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-.

In another preferred embodiment, the invention relates to compounds of formula I, supra, wherein $R^2$ represents a cyclopropyl- group.

In another preferred embodiment, the invention relates to compounds of formula I, supra, wherein $R^3$ represents

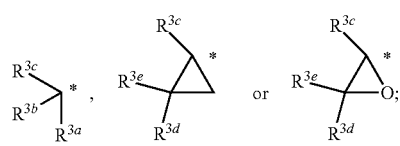

wherein * indicates the point of attachment of said group with the rest of the molecule;
wherein $R^{3a}$, $R^{3b}$, $R^{3c}$, $R^{3d}$, and $R^{3e}$ are as defined above or hereinafter.

In a preferred embodiment, the invention relates to compounds of formula I, supra, wherein $R^3$ represents a group selected from:

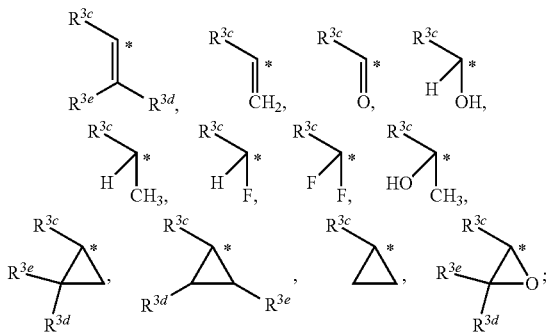

wherein * indicates the point of attachment of said groups with the rest of the molecule;
wherein $R^{3c}$, $R^{3d}$, and $R^{3e}$ are as defined above or hereinafter.

In another preferred embodiment, the invention relates to compounds of formula I, supra, wherein $R^{3a}$ and $R^{3b}$ represent, independently from each other, a hydrogen atom, or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group. So, if $R^{3a}$ is a hydrogen atom, then $R^{3b}$ is not a hydrogen atom, and if $R^{3b}$ is a hydrogen atom, then $R^{3a}$ is not a hydrogen atom; if Rya a hydroxy group, then $R^{3b}$ is not a hydroxy group, and if $R^{3b}$ is a hydroxy group, then $R^{3a}$ is not a hydroxy group. The halogen atom preferably is a fluorine atom.

In another preferred embodiment, the invention relates to compounds of formula I, supra, wherein $R^{3a}$, $R^{3b}$ represent, independently from each other, a hydrogen atom, or a halogen atom or a hydroxy- or $C_1$-$C_3$-alkyl- group, with the proviso that not both of $R^{3a}$ and $R^{3b}$ represent a hydrogen atom and not both of $R^{3a}$ and $R^{3b}$ represent a hydroxy group. The halogen atom preferably is a fluorine atom.

In another preferred embodiment, the invention relates to compounds of formula I, supra, wherein $R^{3a}$, $R^{3b}$ represent, independently from each other, a hydrogen atom or a halogen atom, with the proviso that not both of $R^{3a}$ and $R^{3b}$ represent a hydrogen atom. The halogen atom preferably is a fluorine atom.

In another preferred embodiment, the invention relates to compounds of formula I, supra, wherein $R^{3a}$, $R^{3b}$ together represent =O or =C($R^{3d}$)($R^{3e}$).

In another preferred embodiment, the invention relates to compounds of formula I, supra, wherein $R^{3a}$, $R^{3b}$ together with the carbon atom they are attached to, form a cyclopropyl- or cyclobutyl-ring; wherein said cyclopropyl- or cyclobutyl-ring is optionally substituted with a $C_1$-$C_3$-alkyl- group.

In another preferred embodiment, the invention relates to compounds of formula I, supra, wherein $R^{3a}$, $R^{3b}$ together with the carbon atom they are attached to, form a cyclopropyl-ring.

In another preferred embodiment, the invention relates to compounds of formula I, supra, wherein $R^{3a}$, $R^{3b}$ represent, independently from each other, a hydrogen atom, or a halogen atom or a hydroxy- or $C_1$-$C_3$-alkyl- group, with the proviso that not both of $R^{3a}$ represent a hydrogen atom and not both of $R^{3a}$ and $R^{3b}$ represent a hydroxy group; or $R^{3a}$, $R^{3b}$ together represent =O or =CH$_2$.

In another preferred embodiment, the invention relates to compounds of formula I, supra, wherein $R^3$ represents

wherein * indicates the point of attachment of said group with the rest of the molecule;
wherein $R^{3c}$ is as defined above or hereinafter.

The invention relates to compounds of formula I, supra, wherein $R^{3c}$ represents an aryl- or heteroaryl- group; wherein said aryl- or heteroaryl- group is substituted, identically, or differently, with 1, 2, 3 or 4 $R^7$ groups. Preferably, the aryl- group is a phenyl- group and the heteroaryl- group is a pyridyl- group.

In a preferred embodiment, the invention relates to compounds of formula I, supra, wherein $R^{3c}$ represents an aryl- group; wherein said aryl- group is substituted, identically or differently, with 1, 2 or 3 $R^7$ groups.

In another preferred embodiment, the invention relates to compounds of formula I, supra, wherein $R^{3c}$ represents a phenyl- group; wherein said phenyl- group is substituted, identically or differently, with 1, 2, 3 or 4 $R^7$ groups.

In another preferred embodiment, the invention relates to compounds of formula I, supra, wherein $R^{3c}$ represents a phenyl- group; wherein said phenyl- group is substituted, identically or differently, with 1, 2 or 3 $R^7$ groups.

In another preferred embodiment, the invention relates to compounds of formula I, supra, wherein $R^{3c}$ represents a phenyl- group; wherein said phenyl- group is substituted, identically or differently, with 1 or 2 $R^7$ groups.

In another preferred embodiment, the invention relates to compounds of formula I, supra, wherein $R^{3c}$ represents a group selected from:

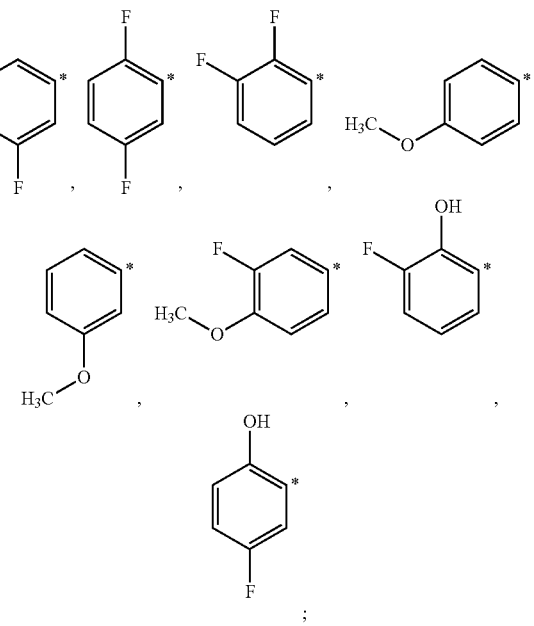

wherein * indicates the point of attachment of said groups with the rest of the molecule.

Compounds of the present invention, in which $R^{3c}$ comprises a hydroxy- group in ortho position to the point of attachment of $R^{3c}$ to the rest of the molecule, show a very high inhibitory effect on Mps-1. Thus, in another preferred embodiment, the invention relates to compounds of formula I, supra, wherein $R^{3c}$ represents

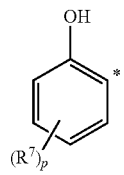

wherein * indicates the point of attachment of said group with the rest of the molecule, $R^7$ is as defined above or hereinafter, and p is 1 or 2.

In another preferred embodiment, the invention relates to compounds of formula I, supra, wherein $R^{3c}$ represents

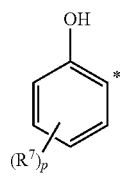

wherein * indicates the point of attachment of said group with the rest of the molecule, $R^7$ represents a fluorine atom, and p is 1 or 2.

In another preferred embodiment, the invention relates to compounds of formula I, supra, wherein $R^{3c}$ represents

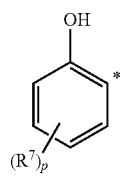

wherein * indicates the point of attachment of said group with the rest of the molecule, $R^7$ represents a fluorine atom, and p is 1.

In another preferred embodiment, the invention relates to compounds of formula I, supra, wherein $R^{3c}$ represents a group selected from:

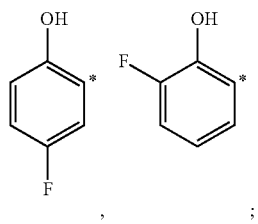

wherein * indicates the point of attachment of said groups with the rest of the molecule.

In another preferred embodiment, the invention relates to compounds of formula I, supra, wherein both of $R^{3d}$ and $R^{3e}$ represent a hydrogen atom.

In another preferred embodiment, the invention relates to compounds of formula I, supra, wherein $R^4$ represents a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group.

In another preferred embodiment, the invention relates to compounds of formula I, supra, wherein $R^4$ represents a $C_1$-$C_3$-alkyl- group.

In another preferred embodiment, the invention relates to compounds of formula I, supra, wherein $R^4$ represents a methyl- group.

In another preferred embodiment, the invention relates to compounds of formula I, supra, wherein $R^5$ represents a hydrogen atom or a $C_1$-$C_6$-alkyl-, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl- group;
wherein said $C_1$-$C_6$-alkyl-, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, 3- to 7-membered heterocycloalkyl-, $C_4$-$C_8$-cycloalkenyl-, aryl- or heteroaryl-group is optionally substituted, identically or differently, with 1, 2, 3, 4 or 5 $R^8$ groups.

In another preferred embodiment, the invention relates to compounds of formula I, supra, wherein $R^5$ represents a $C_1$-$C_6$-alkyl-, —$(CH_2)_m$-(3- to 7-membered heterocycloalkyl), $C_1$-$C_6$-alkoxy-$C_1$-$C_6$-alkyl- or halo-$C_1$-$C_6$-alkyl- group; wherein said —$(CH_2)_m$-(3- to 7-membered heterocycloalkyl) group is optionally substituted, identically or differently, with 1, 2 or 3 $R^8$ groups.

In another preferred embodiment, the invention relates to compounds of formula I, supra, wherein $R^5$ represents a group selected from:

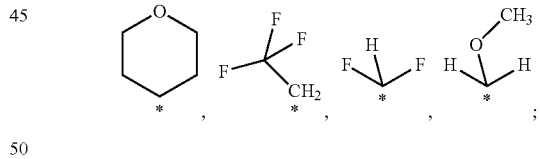

wherein * indicates the point of attachment of said groups with the rest of the molecule.

In another preferred embodiment, the invention relates to compounds of formula I, supra, wherein $R^5$ represents

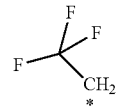

wherein * indicates the point of attachment of said group with the rest of the molecule.

In another preferred embodiment, the invention relates to compounds of formula I, supra, wherein $R^7$ represents a halogen atom, or a HO—, —CN, $C_1$-$C_3$-alkoxy-, $C_1$-$C_3$- alkyl-, halo-$C_1$-$C_3$-alkyl-, HO—$C_1$-$C_3$-alkyl-, $C_1$-$C_3$-alkoxy-$C_1$-$C_3$-alkyl- or halo-$C_1$-$C_3$-alkoxy-$C_1$-$C_3$-alkyl- group.

In another preferred embodiment, the invention relates to compounds of formula I, supra, wherein $R^7$ represents a halogen atom, or a HO—, —CN, $C_1$-$C_3$-alkoxy-, $C_1$-$C_3$-alkyl- or halo-$C_1$-$C_3$-alkyl- group.

In another preferred embodiment, the invention relates to compounds of formula I, supra, wherein $R^7$ represents a halogen atom, or a HO— or $C_1$-$C_3$-alkoxy- group.

In another preferred embodiment, the invention relates to compounds of formula I, supra, wherein $R^7$ represents a fluorine atom, or a HO— or methoxy- group.

In another preferred embodiment, the invention relates to compounds of formula I, supra, wherein $R^7$ represents a fluorine atom.

In another preferred embodiment, the invention relates to compounds of formula I, supra, wherein $R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group.

In another preferred embodiment, the invention relates to compounds of formula I, supra, wherein $R^8$ represents a halogen atom or a $C_1$-$C_3$-alkyl- group.

In another preferred embodiment, with respect to compounds of formula I, supra, m is 0.

In another preferred embodiment, with respect to compounds of formula I, supra, m is 1.

In another preferred embodiment, with respect to compounds of formula I, supra, n is 0.

In another preferred embodiment, with respect to compounds of formula I, supra, n is 1.

In an embodiment of the above-mentioned aspects, the invention relates to compounds of formula I, according to any of the above-mentioned embodiments, in the form of or a stereoisomer, a tautomer, an N-oxide, a hydrate, a solvate, or a salt thereof, or a mixture of same.

It is to be understood that the present invention relates also to any combination of the preferred embodiments described above. Some examples of combinations are given hereinafter. However, the invention is not limited to these combinations.

In a preferred embodiment, the invention relates to compounds of general formula I, supra, in which:

A represents

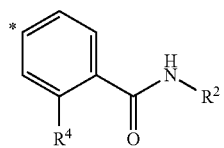

wherein * indicates the point of attachment of said group with the rest of the molecule;

$R^2$ represents a methyl-, ethyl- or cyclopropyl- group;

wherein said methyl- or ethyl- group is optionally substituted, identically or differently, with 1, 2, 3 or 4 groups selected from: halogen, —OH, —CN, $C_1$-$C_3$-alkoxy-;

wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-;

$R^3$ represents
—C($R^{3a}$)($R^{3b}$)($R^{3c}$);
or
$R^3$ represents

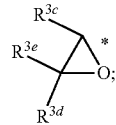

wherein * indicates the point of attachment of said group with the rest of the molecule;

$R^{3a}$, $R^{3b}$
represent, independently from each other, a hydrogen atom or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group;
or
$R^{3a}$, $R^{3b}$
together represent =O or =C($R^{3d}$)($R^{3e}$);
or
$R^{3a}$, $R^{3b}$
together with the carbon atom they are attached to, form a cyclopropyl- or cyclobutyl-ring;

wherein said cyclopropyl- or cyclobutyl-ring is optionally substituted, identically, or differently, with 1 or 2 $R^{3d}$ groups;

$R^{3c}$ represents an aryl- or heteroaryl- group;

wherein said aryl- or heteroaryl- group is substituted, identically or differently, with 1, 2, 3 or 4 $R^7$ groups;

$R^{3d}$, $R^{3e}$
represent, independently from each other, a hydrogen atom or a $C_1$-$C_3$-alkyl- group;

$R^4$ represents a hydrogen atom, a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;

$R^5$ represents a $C_1$-$C_6$-alkyl-, —$(CH_2)_m$-(3- to 7-membered heterocycloalkyl), $C_1$-$C_6$-alkoxy-$C_1$-$C_6$-alkyl- or halo-$C_1$-$C_6$-alkyl- group;

wherein said —$(CH_2)_m$-(3- to 7-membered heterocycloalkyl) group is optionally substituted, identically or differently, with 1, 2 or 3 $R^8$ groups;

$R^6$, $R^{6a}$, $R^{6b}$
represent, independently from each other, a hydrogen atom or a $C_1$-$C_6$-alkyl- group;

$R^7$ represents a halogen atom, or a hydroxy-, —CN, $C_1$-$C_6$-alkoxy-, $C_1$-$C_6$-alkyl-, halo-$C_1$-$C_6$-alkyl-, $R^{6a}(R^{6b})$N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl- group;

$R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group; wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;

or a stereoisomer, a tautomer, an N-oxide, a hydrate, a solvate, or a salt thereof, or a mixture of same.

In another preferred embodiment, the invention relates to compounds of general formula I, supra, in which:

A represents

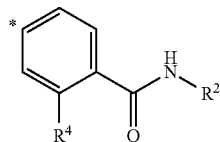

wherein * indicates the point of attachment of said group with the rest of the molecule;

$R^2$ represents a methyl-, ethyl- or cyclopropyl- group;
  wherein said methyl- or ethyl- group is optionally substituted, identically or differently, with 1, 2, 3 or 4 groups selected from: halogen, —OH, —CN, $C_1$-$C_3$-alkoxy-;
  wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-;

$R^3$ represents
  —C($R^{3a}$)($R^{3b}$)($R^{3c}$);

$R^{3a}$, $R^{3b}$
  represent, independently from each other, a hydrogen atom or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group;

or
$R^{3a}$, $R^{3b}$
  together represent =O or =C($R^{3d}$)($R^{3e}$);

or
$R^{3a}$, $R^{3b}$
  together with the carbon atom they are attached to, form a cyclopropyl- or cyclobutyl-ring;
  wherein said cyclopropyl- or cyclobutyl-ring is optionally substituted, identically or differently, with 1 or 2 $R^{3d}$ groups;

$R^{3c}$ represents an aryl- group;
  wherein said aryl- group is substituted, identically or differently, with 1, 2, 3 or 4 $R^7$ groups;

$R^{3d}$, $R^{3e}$
  represent, independently from each other, a hydrogen atom or a $C_1$-$C_3$-alkyl- group;

$R^4$ represents a hydrogen atom, a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;

$R^5$ represents a $C_1$-$C_6$-alkyl-, —(CH$_2$)$_m$-(3- to 7-membered heterocycloalkyl), $C_1$-$C_6$-alkoxy-$C_1$-$C_6$-alkyl- or halo-$C_1$-$C_6$-alkyl- group;
  wherein said —(CH$_2$)$_m$-(3- to 7-membered heterocycloalkyl) group is optionally substituted, identically or differently, with 1, 2 or 3 $R^8$ groups;

$R^6$, $R^{6a}$, $R^{6b}$
  represent, independently from each other, a hydrogen atom or a $C_1$-$C_6$-alkyl- group;

$R^7$ represents a halogen atom, or a hydroxy-, —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl- group;

$R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group;
  wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;

or a stereoisomer, a tautomer, an N-oxide, a hydrate, a solvate, or a salt thereof, or a mixture of same.

In another preferred embodiment, the invention relates to compounds of general formula I, supra, in which:

A represents

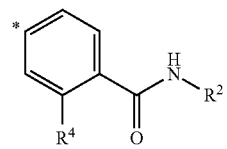

wherein * indicates the point of attachment of said group with the rest of the molecule;

$R^2$ represents a cyclopropyl- group;
  wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-;

$R^3$ represents
  —C($R^{3a}$)($R^{3b}$)($R^{3c}$);

$R^{3a}$, $R^{3b}$
  represent, independently from each other, a hydrogen atom or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group;

or
$R^{3a}$, $R^{3b}$
  together represent =O or =C($R^{3d}$)($R^{3e}$);

or
$R^{3a}$, $R^{3b}$
  together with the carbon atom they are attached to, form a cyclopropyl-ring;
  wherein said cyclopropyl-ring is optionally substituted, identically or differently, with 1 or 2 $R^{3d}$ groups;

$R^{3c}$ represents an phenyl- group;
  wherein said phenyl- group is substituted, identically or differently, with 1, 2, 3 or 4 $R^7$ groups;

$R^{3d}$, $R^{3e}$
  represent, independently from each other, a hydrogen atom or a $C_1$-$C_3$-alkyl- group;

$R^4$ represents a hydrogen atom, a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;

$R^5$ represents a $C_1$-$C_6$-alkyl-, —(CH$_2$)$_m$-(3- to 7-membered heterocycloalkyl), $C_1$-$C_6$-alkoxy-$C_1$-$C_6$-alkyl- or halo-$C_1$-$C_6$-alkyl- group;
  wherein said —(CH$_2$)$_m$-(3- to 7-membered heterocycloalkyl) group is optionally substituted, identically or differently, with 1, 2 or 3 $R^8$ groups;

$R^6$, $R^{6a}$, $R^{6b}$
  represent, independently from each other, a hydrogen atom or a $C_1$-$C_6$-alkyl- group;

$R^7$ represents a halogen atom, or a hydroxy-, —CN, $C_1$-$C_6$-alkoxy-, $C_1$-$C_6$-alkyl-, halo-$C_1$-$C_6$-alkyl-, $R^{6a}$($R^{6b}$)N—

$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl- group;

$R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group; wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;

or a stereoisomer, a tautomer, an N-oxide, a hydrate, a solvate, or a salt thereof, or a mixture of same.

In another preferred embodiment, the invention relates to compounds of general formula I, supra, in which:

A represents

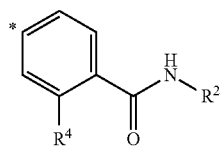

wherein * indicates the point of attachment of said group with the rest of the molecule;

$R^2$ represents a cyclopropyl- group;

$R^3$ represents
—C($R^{3a}$)($R^{3b}$)($R^{3c}$);

$R^{3a}$, $R^{3b}$
represent, independently from each other, a hydrogen atom or a halogen atom, with the proviso that not both of $R^{3a}$ and $R^{3b}$ represent a hydrogen atom;

or $R^{3a}$, $R^{3b}$
together represent =O or =$CH_2$;

$R^{3c}$ represents a phenyl- group;
wherein said phenyl- group is substituted, identically or differently, with 1, 2 or 3 $R^7$ groups;

$R^4$ represents a hydrogen atom, a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;

$R^5$ represents a $C_1$-$C_6$-alkyl-, —($CH_2$)$_m$-(3- to 7-membered heterocycloalkyl), $C_1$-$C_6$-alkoxy-$C_1$-$C_6$-alkyl- or halo-$C_1$-$C_6$-alkyl- group;
wherein said —($CH_2$)$_m$-(3- to 7-membered heterocycloalkyl) group is optionally substituted, identically or differently, with 1, 2 or 3 $R^8$ groups;

$R^6$, $R^{6a}$, $R^{6b}$
represent, independently from each other, a hydrogen atom or a $C_1$-$C_6$-alkyl- group;

$R^7$ represents a halogen atom, or a hydroxy-, —CN, $C_1$-$C_6$-alkoxy-, $C_1$-$C_6$-alkyl-, halo-$C_1$-$C_6$-alkyl-, $R^{6a}$($R^{6b}$)N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl- group;

$R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group; wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;

or a stereoisomer, a tautomer, an N-oxide, a hydrate, a solvate, or a salt thereof, or a mixture of same.

In another preferred embodiment, the invention relates to compounds of general formula I, supra, in which:

A represents

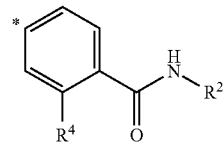

wherein * indicates the point of attachment of said group with the rest of the molecule;

$R^2$ represents a cyclopropyl- group;

$R^3$ represents
—C($R^{3a}$)($R^{3b}$)($R^{3c}$);

$R^{3a}$, $R^{3b}$
represent, independently from each other, a hydrogen atom or a halogen atom, with the proviso that not both of $R^{3a}$ and $R^{3b}$ represent a hydrogen atom;

or $R^{3a}$, $R^{3b}$
together represent =O or =$CH_2$;

$R^{3c}$ represents a phenyl- group;
wherein said phenyl- group is substituted, identically or differently, with 1, 2 or 3 $R^7$ groups;

$R^4$ represents a methyl- group;

$R^5$ represents a $C_1$-$C_6$-alkyl-, —($CH_2$)$_m$-(3- to 7-membered heterocycloalkyl), $C_1$-$C_6$-alkoxy-$C_1$-$C_6$-alkyl- or halo-$C_1$-$C_6$-alkyl- group;
wherein said —($CH_2$)$_m$-(3- to 7-membered heterocycloalkyl) group is optionally substituted, identically or differently, with 1, 2 or 3 $R^8$ groups;

$R^6$, $R^{6a}$, $R^{6b}$
represent, independently from each other, a hydrogen atom or a $C_1$-$C_6$-alkyl- group;

$R^7$ represents a halogen atom, or a HO— or $C_1$-$C_3$-alkoxy- group;

$R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group; wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;

or a stereoisomer, a tautomer, an N-oxide, a hydrate, a solvate, or a salt thereof, or a mixture of same.

In another preferred embodiment, the invention relates to compounds of general formula I, supra, in which:

A represents

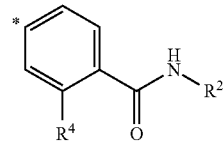

wherein * indicates the point of attachment of said group with the rest of the molecule;

$R^2$ represents a cyclopropyl- group;
wherein said cyclopropyl- group is optionally substituted, identically or differently, with 1, 2, 3 or 4 groups selected from: halogen, —OH, —CN, $C_1$-$C_3$-alkyl-, $C_1$-$C_3$-alkoxy-, HO—$C_1$-$C_3$-alkyl-, halo-$C_1$-$C_3$-alkyl-;

$R^3$ represents
—C($R^{3a}$)($R^{3b}$)($R^{3c}$);
$R^{3a}$, $R^{3b}$
represent, independently from each other, a hydrogen atom, or a halogen atom or a hydroxy- or $C_1$-$C_3$-alkyl- group, with the proviso that not both of $R^{3a}$ and $R^{3b}$ represent a hydrogen atom and not both of $R^{3a}$ and $R^{3b}$ represent a hydroxy group;
or
$R^{3a}$, $R^{3b}$
together represent =O or =$CH_2$;
$R^{3c}$ represents a phenyl- group;
wherein said phenyl- group is substituted, identically or differently, with 1, 2 or 3 $R^7$ groups;
$R^4$ represents a methyl- group;
$R^5$ represents

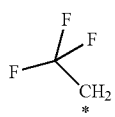

wherein * indicates the point of attachment of said group with the rest of the molecule;
$R^7$ represents a halogen atom, or a HO— or $C_1$-$C_3$-alkoxy- group;
$R^8$ represents a halogen atom or a $C_1$-$C_3$-alkyl- group;
or a stereoisomer, a tautomer, an N-oxide, a hydrate, a solvate, or a salt thereof, or a mixture of same.

In another preferred embodiment, the invention relates to compounds of general formula I, supra, in which:
A represents

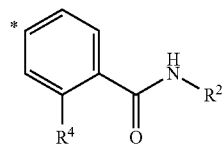

wherein * indicates the point of attachment of said group with the rest of the molecule;
$R^2$ represents a cyclopropyl- group;
$R^3$ represents
—C($R^{3a}$)($R^{3b}$)($R^{3c}$);
$R^{3a}$, $R^{3b}$
together with the carbon atom they are attached to, form a cyclopropyl-ring;
$R^{3c}$ represents a phenyl- group;
wherein said phenyl- group is substituted, identically or differently, with 1 or 2 $R^7$ groups;
$R^4$ represents a methyl- group;
$R^5$ represents

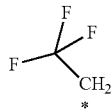

wherein * indicates the point of attachment of said group with the rest of the molecule;

$R^7$ represents a halogen atom, preferably a fluorine atom, or a hydroxy- or methoxy- group;
or a stereoisomer, a tautomer, an N-oxide, a hydrate, a solvate, or a salt thereof, or a mixture of same.

In another preferred embodiment, the invention relates to compounds of general formula I, supra, in which:
A represents

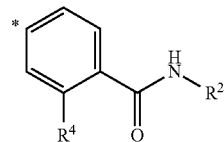

wherein * indicates the point of attachment of said group with the rest of the molecule;
$R^2$ represents a cyclopropyl- group;
$R^3$ represents
—C($R^{3a}$)($R^{3b}$)($R^{3c}$);
or
$R^3$ represents

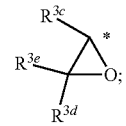

wherein * indicates the point of attachment of said group with the rest of the molecule;
$R^{3a}$, $R^{3b}$
represent, independently from each other, a hydrogen atom or a halogen atom or a hydroxy-, $C_1$-$C_3$-alkyl-, HO—$C_1$-$C_3$-alkyl-, $C_2$-$C_4$-alkenyl-, halo-$C_1$-$C_3$-alkyl-, $C_1$-$C_3$-alkoxy- or halo-$C_1$-$C_3$-alkoxy- group, with the proviso that not both of $R^{3a}$ and $R^{3b}$ represent a hydrogen atom and not both of $R^{3a}$ and $R^{3b}$ represent a hydroxy group;
or
$R^{3a}$, $R^{3b}$
together represent =O or =C($R^{3d}$)($R^{3e}$);
or
$R^{3a}$, $R^{3b}$
together with the carbon atom they are attached to, form a cyclopropyl- or cyclobutyl-ring;
wherein said cyclopropyl- or cyclobutyl-ring is optionally substituted, identically or differently, with 1 or 2 $R^{3d}$ groups;
$R^3$ represents

wherein * indicates the point of attachment of said group with the rest of the molecule;
$R^{3d}$, $R^{3e}$
represent, independently from each other, a hydrogen atom or a $C_1$-$C_3$-alkyl- group;

$R^4$ represents a halogen atom, or a —CN, $C_1$-$C_3$-alkyl-, $C_1$-$C_3$-alkoxy-, halo-$C_1$-$C_3$-alkyl- or halo-$C_1$-$C_3$-alkoxy- group;

$R^5$ represents a $C_1$-$C_6$-alkyl-, —$(CH_2)_m$-(3- to 7-membered heterocycloalkyl), $C_1$-$C_6$-alkoxy-$C_1$-$C_6$-alkyl- or halo-$C_1$-$C_6$-alkyl- group;
  wherein said —$(CH_2)_m$-(3- to 7-membered heterocycloalkyl) group is optionally substituted, identically or differently, with 1, 2 or 3 $R^8$ groups;

$R^6$, $R^{6a}$, $R^{6b}$ represent, independently from each other, a hydrogen atom or a $C_1$-$C_6$-alkyl- group;

$R^7$ represents a halogen atom, or a hydroxy-, $C_1$-$C_6$-alkoxy-, $C_1$-$C_6$-alkyl-, halo-$C_1$-$C_6$-alkyl-, $R^{6a}(R^{6b})N$—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl- group;

$R^8$ represents a halogen atom, or a —CN, hydroxy-, $C_1$-$C_6$-alkyl-, halo-$C_1$-$C_6$-alkyl-, HO—$C_1$-$C_6$-alkyl-, $C_1$-$C_6$-alkoxy- or halo-$C_1$-$C_6$-alkoxy- group; wherein said 3- to 7-membered heterocycloalkyl- or heteroaryl- group is optionally substituted, identically or differently, with 1, 2, 3 or 4 $C_1$-$C_6$-alkyl- groups;

m is an integer of 0, 1 or 2;
p is an integer of 1 or 2;
or a stereoisomer, a tautomer, an N-oxide, a hydrate, a solvate, or a salt thereof, or a mixture of same.

In another preferred embodiment, the invention relates to compounds of general formula I, supra, in which:
A represents

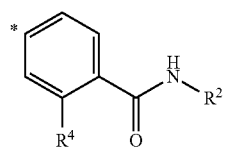

wherein * indicates the point of attachment of said group with the rest of the molecule;
$R^2$ represents a cyclopropyl- group;
$R^3$ represents a group selected from:

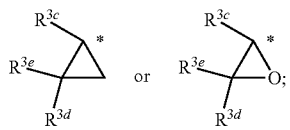

wherein * indicates the point of attachment of said group with the rest of the molecule;
$R^{3c}$ represents

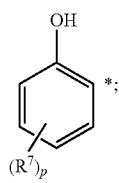

wherein * indicates the point of attachment of said group with the rest of the molecule;
$R^{3d}$ represents a hydrogen atom;
$R^{3e}$ represents a hydrogen atom;

$R^4$ represents a methyl- group;
$R^5$ represents

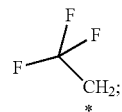

wherein * indicates the point of attachment of said group with the rest of the molecule;
$R^7$ represents a halogen atom, preferably a fluorine atom;
p is an integer of 1 or 2;
or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula I, supra.

More particularly still, the present invention covers compounds of general formula I which are disclosed in the Experimental Section of this text, infra.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

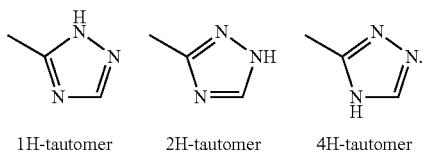

1H-tautomer     2H-tautomer     4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

Furthermore, the present invention includes all possible crystalline forms, or polymorphs, of the compounds of the present invention, either as single polymorphs, or as a mixture of more than one polymorph, in any ratio.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

In an embodiment of the above-mentioned aspects, the invention relates to compounds of formula I, according to any of the above-mentioned embodiments, in the form of or a stereoisomer, a tautomer, an N-oxide, a hydrate, a solvate, or a salt thereof, or a mixture of same.

The compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Therefore, the compounds of formula I, supra, are expected to be valuable as therapeutic agents.

Accordingly, in another embodiment, the present invention is directed to a compound of general formula I, supra, or a stereoisomer, a tautomer, an N-oxide, a hydrate, a solvate, or a salt thereof, particularly a pharmaceutically acceptable salt thereof, or a mixture of same, for use in the treatment or prophylaxis of a disease.

In another embodiment, the present invention provides a method of treating disorders associated with enhanced uncontrolled proliferative cellular processes in a patient in need of such treatment, comprising administering to the patient an effective amount of a compound of formula I.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The terms "cell proliferative disorder" or "disorder associated with enhanced uncontrolled proliferative cellular processes" include disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

In another embodiment, the present invention is directed to a compound of general formula I, or a stereoisomer, a tautomer, an N-oxide, a hydrate, a solvate, or a salt thereof, particularly a pharmaceutically acceptable salt thereof, or a mixture of same, for use in the treatment or prophylaxis of a disease, wherein said disease is a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is mediated by the mitogen-activated protein kinase (MEK-ERK) pathway, more particularly in which the disease of uncontrolled cell growth, proliferation and/or survival, inappropriate cellular immune response, or inappropriate cellular inflammatory response is a haemotological tumour, a solid tumour and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The present invention also relates to useful forms of the compounds as disclosed herein, such as metabolites, hydrates, solvates, prodrugs, salts, in particular pharmaceutically acceptable salts, in vivo hydrolysable esters, and co-precipitates. The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentane ionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Compounds of formula I may be administered as the sole pharmaceutical agent or in combination with one or more additional therapeutic agents where the combination causes no unacceptable adverse effects. This combination therapy includes administration of a single pharmaceutical dosage formulation which contains a compound of formula I and one or more additional therapeutic agents, as well as administration of the compound of formula I and each additional therapeutic agent in its own separate pharmaceutical dosage formulation. For example, a compound of formula I and a therapeutic agent may be administered to the patient together in a single oral dosage composition such as a tablet or capsule, or each agent may be administered in separate dosage formulations.

Where separate dosage formulations are used, the compound of formula I and one or more additional therapeutic agents may be administered at essentially the same time (e.g., concurrently) or at separately staggered times (e.g., sequentially).

In another aspect, the invention provides a pharmaceutical composition comprising a compound of general formula I, or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

Preferably, the pharmaceutical combination comprises:
one or more compounds of general formula I, or a stereoisomer, a tautomer, an N-oxide, a hydrate, a solvate, or a salt thereof, particularly a pharmaceutically acceptable salt thereof, or a mixture of same; and one or more agents selected from: a taxane, such as Docetaxel, Paclitaxel, or Taxol; an epothilone, such as Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an antiandrogen, such as Flutamide, Cyproterone acetate, or Bicalutamide; Bortezomib; a platinum derivative, such as Cisplatin, or Carboplatin; Chlorambucil; Methotrexate; and Rituximab.

In still another aspect, the invention provides a process for preparing a pharmaceutical composition. The process includes the step of combining at least one compound of formula I as defined above with at least one pharmaceutically acceptable carrier, and bringing the resulting combination into a suitable administration form.

In still another aspect, the invention provides use of a compound of formula I as defined above for manufacturing a pharmaceutical composition for the treatment or prevention of a cell proliferative disorder. In certain embodiments, the cell proliferative disorder is cancer.

The active component of formula I can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Regardless of the route of administration selected, the compounds of the invention, which may be used in a suitable hydrated form, and/or the pharmaceutical compositions of the present invention, are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient.

In accordance with another aspect, the present invention covers methods of preparing compounds of the present invention.

In accordance with a first embodiment, the present invention also relates to a method of preparing a compound of general formula I, supra, said method comprising the step of allowing an intermediate compound of general formula Ia:

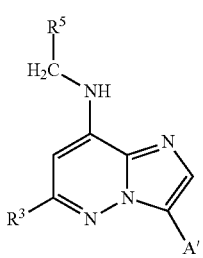

Ia in which $R^3$ and $R^5$ are as defined for general formula I, supra;
and A' is

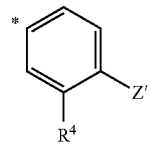

wherein * indicates the point of attachment of said group with the rest of the molecule, $R^4$ is as defined for general formula I, supra, and Z' represents a group selected from: —C(=O)OH and —C(=O)O—($C_1$-$C_6$-alkyl);
to react with a compound of general formula Ib:

$H_2NR^2$

Ib in which $R^2$ is as defined as for general formula I, supra; thereby giving, upon optional deprotection, a compound of general formula I:

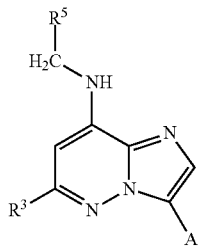

I in which $R^3$, $R^5$ and A are as defined for general formula I, supra.

In accordance with another embodiment, the present invention also relates to a method of preparing a compound of general formula I, supra, said method comprising the step of allowing an intermediate compound of general formula II:

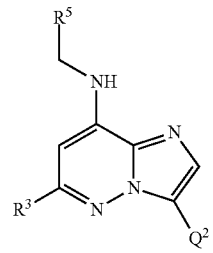

II in which $R^3$ and $R^5$ are as defined for general formula I, supra, and $Q^2$ is a leaving group, preferably $Q^2$ is a halogen atom;
to react with a compound of general formula IIa:

A—Y

IIa in which A is as defined for general formula I, supra, and Y is a substituent which is displaced in a coupling reaction, such as a boronic acid group, or an ester of a boronic acid group, for example,
thereby giving, upon optional deprotection, a compound of general formula I:

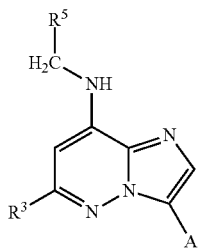

in which $R^3$, $R^5$ and A are as defined for general formula I, supra.

In accordance with another embodiment, the present invention also relates to a method of preparing a compound of general formula I, supra, said method comprising the step of allowing an intermediate compound of general formula VII:

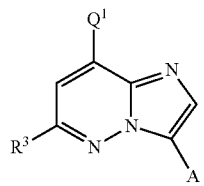

in which $R^3$ and A are as defined for general formula I, supra, and $Q^1$ is a leaving group, for example a halogen atom,
to react with a compound of general formula VIIIa:

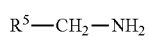

R⁵—CH₂—NH₂ in which $R^5$ is as defined for general formula I, supra,
thereby giving, upon optional deprotection, a compound of general formula I:

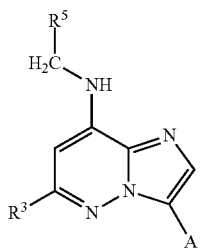

in which $R^3$, $R^5$ and A are as defined for general formula I, supra.

In accordance with another embodiment, the present invention also relates to a method of preparing a compound of general formula I, supra, said method comprising the step of allowing an intermediate compound of general formula VII:

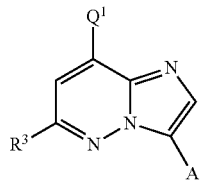

in which $R^3$ and A are as defined for general formula I, supra, and $Q^1$ is an optionally protected $NH_2$— group,
to react with a compound of general formula VIIIb:

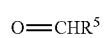

O=CHR⁵ in which $R^5$ is as defined for general formula I, supra,
thereby giving, upon optional deprotection, a compound of general formula I:

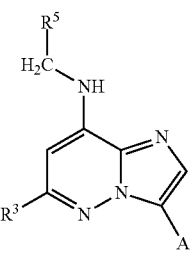

in which $R^3$, $R^5$ and A are as defined for general formula I, supra.

In accordance with another embodiment, the present invention also relates to a method of preparing a compound of general formula I, supra, said method comprising the step of conversion of a compound of general formula XVII:

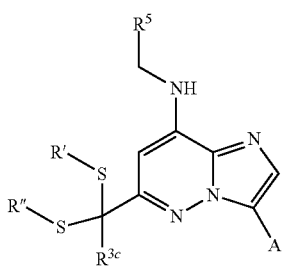

in which $R^{3c}$, $R^5$ and A are as defined for general formula I, supra; and
R' and R" represent, independent from each other, a $C_1$-$C_6$-alkyl- group; or
R' and R" together represent an alkylene group, for a example an ethylene group —$CH_2$—$CH_2$—;

to a compound of general formula XIII:

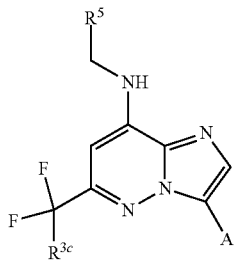

XIII in which $R^{3c}$, $R^5$ and A are as defined for general formula I, supra.

In accordance with another embodiment, the present invention also relates to a method of preparing a compound of general formula I, supra, said method comprising the step of conversion of a compound of general formula XXI:

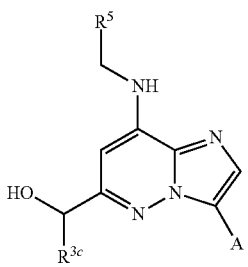

XXI in which $R^{3c}$, $R^5$ and A are as defined for general formula I, supra;
to a compound of general formula XX:

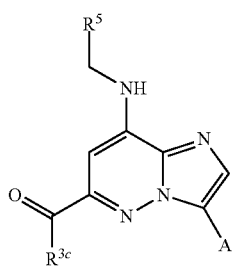

XX in which $R^{3c}$, $R^5$ and A are as defined for general formula I, supra.

In accordance with another embodiment, the present invention also relates to a method of preparing a compound of general formula I, supra, said method comprising the step of conversion of a compound of general formula XIX:

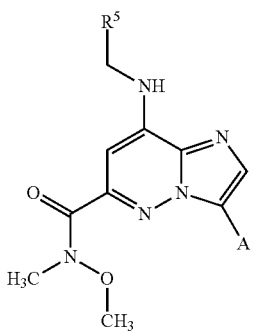

XIX in which $R^5$ and A are as defined for general formula I, supra;
to a compound of general formula XX:

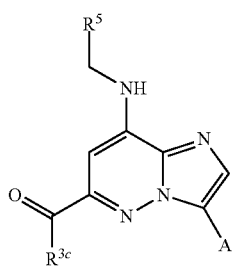

XX in which $R^{3c}$, $R^5$ and A are as defined for general formula I, supra.

In accordance with another embodiment, the present invention also relates to a method of preparing a compound of general formula I, supra, said method comprising the step of conversion of a compound of general formula XXII:

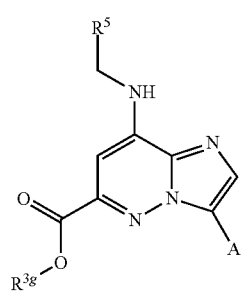

XXII in which $R^5$ and A are as defined for general formula I, supra, and $R^{3g}$ is a hydrogen atom or a $C_1$-$C_6$-alkyl- group;

to a compound of general formula XX:

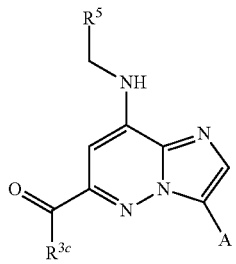

XX in which $R^{3c}$, $R^5$ and A are as defined for general formula I, supra.

In accordance with another embodiment, the present invention also relates to a method of preparing a compound of general formula I, supra, said method comprising the step of conversion of a compound of general formula XXI:

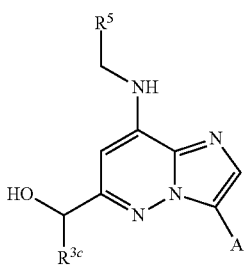

XXI in which $R^5$, $R^{3c}$ and A are as defined for general formula I, supra;
to a compound of general formula XVIII:

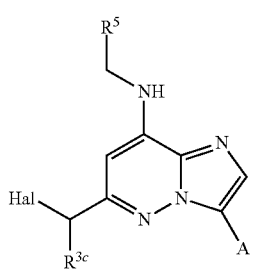

XVIII in which $R^{3c}$, $R^5$ and A are as defined for general formula I, supra, and Hal is a halogene atom, preferably a fluorine atom.

In accordance with another embodiment, the present invention also relates to a method of preparing a compound of general formula I, supra, said method comprising the step of conversion of a compound of general formula XX:

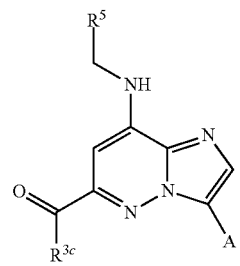

XX in which $R^5$, $R^{3c}$ and A are as defined for general formula I, supra,
to a compound of general formula XVI:

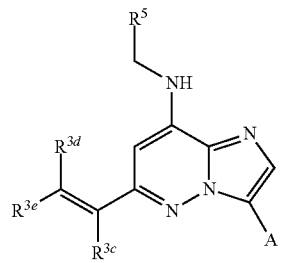

XVI in which $R^{3c}$, $R^{3d}$, $R^{3e}$, $R^5$ and A are as defined for general formula I, supra.

In accordance with another embodiment, the present invention also relates to a method of preparing a compound of general formula I, supra, said method comprising the step of conversion of a compound of general formula XVI:

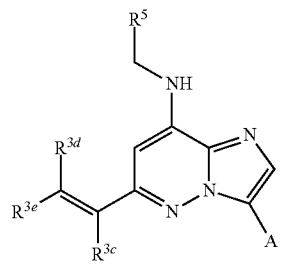

XVI in which $R^{3c}$, $R^{3d}$, $R^{3e}$, $R^5$ and A are as defined for general formula I, supra;
to a compound of general formula XXV:

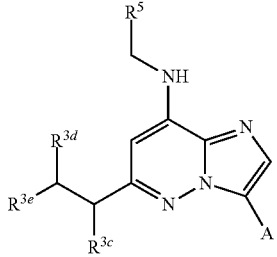

XXV in which $R^{3c}$, $R^{3d}$, $R^{3e}$, $R^5$ and A are as defined for general formula I, supra.

In accordance with another embodiment, the present invention also relates to a method of preparing a compound of general formula I, supra, said method comprising the step of conversion of a compound of general formula XVI:

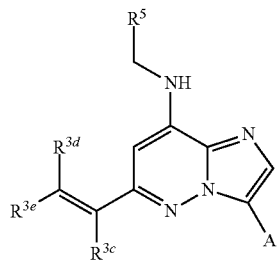

XVI in which $R^{3c}$, $R^{3d}$, $R^{3e}$, $R^5$ and A are as defined for general formula I, supra;

to a compound of general formula XII:

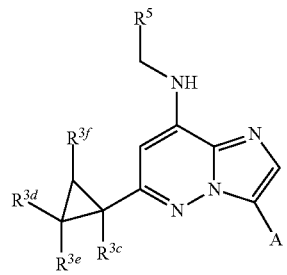

XII in which $R^{3c}$, $R^{3d}$, $R^{3e}$, $R^5$ and A are as defined for general formula I, supra, and $R^{3f}$ is a hydrogen atom or a $C_1$-$C_6$-alkyl- group.

In accordance with another embodiment, the present invention also relates to a method of preparing a compound of general formula I, supra, said method comprising the step of conversion of a compound of general formula XVI:

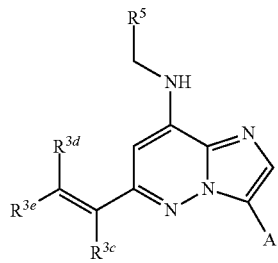

XVI in which $R^{3c}$, $R^{3d}$, $R^{3e}$, $R^5$ and A are as defined for general formula I, supra;

to a compound of general formula XXVI:

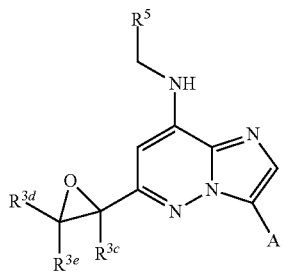

XXVI in which $R^{3c}$, $R^{3d}$, $R^{3e}$, $R^5$ and A are as defined for general formula I, supra.

In accordance with another embodiment, the present invention also relates to a method of preparing a compound of general formula I, supra, said method comprising the step of conversion of a compound of general formula XV:

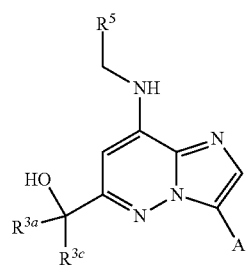

XV in which $R^{3a}$, $R^{3c}$, $R^5$ and A are as defined for general formula I, supra;

to a compound of general formula XI:

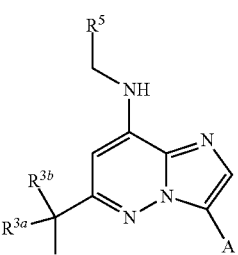

XI in which $R^{3a}$, $R^{3b}$, $R^{3c}$, $R^5$ and A are as defined for general formula I, supra.

In accordance with a further aspect, the present invention covers intermediate compounds which are useful in the preparation of compounds of the present invention of general formula I, particularly in the method described herein.

In particular, the present invention covers intermediate compounds of general formula Ia:

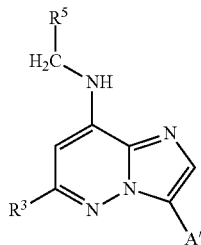

Ia in which $R^3$ and $R^5$ are as defined for general formula I, supra;
and A' is

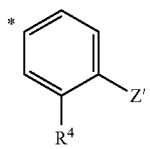

wherein * indicates the point of attachment of said group with the rest of the molecule; $R^4$ is as defined for general formula I, supra, and Z' represents a group selected from: —C(=O)OH and —C(=O)O—($C_1$-$C_6$-alkyl).

In accordance with yet another aspect, the present invention covers intermediate compounds of general formula II:

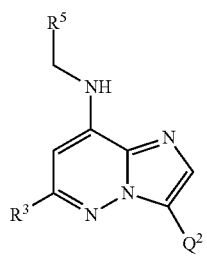

II in which $R^3$ and $R^5$ are as defined for general formula I, supra, and $Q^2$ is a leaving group, preferably $Q^2$ is a halogen atom.

In accordance with a further aspect, the present invention covers intermediate compounds of general formula VII:

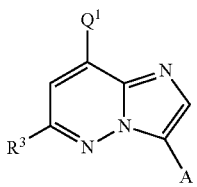

VII in which A, and $R^3$ are as defined for general formula I, supra, and $Q^1$ represents an optionally protected $NH_2$— group or a leaving group.

In accordance with a further aspect, the present invention covers intermediate compounds of general formula XV:

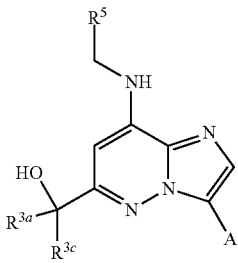

XV in which $R^{3a}$, $R^{3c}$, $R^5$ and A are as defined for general formula I, supra.

In accordance with a further aspect, the present invention covers intermediate compounds of general formula XVI:

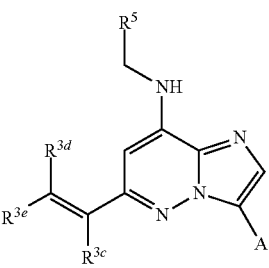

XVI in which $R^{3c}$, $R^{3d}$, $R^{3e}$, $R^5$ and A are as defined for general formula I, supra.

In accordance with a further aspect, the present invention covers intermediate compounds of general formula XVII:

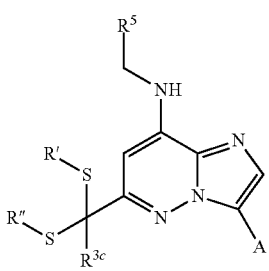

XVII in which $R^{3c}$, $R^5$ and A are as defined for general formula I, supra; and
R' and R" represent, independent from each other, a $C_1$-$C_6$-alkyl- group; or
R' and R" together represent an alkylene group.

In accordance with a further aspect, the present invention covers intermediate compounds of general formula XIX:

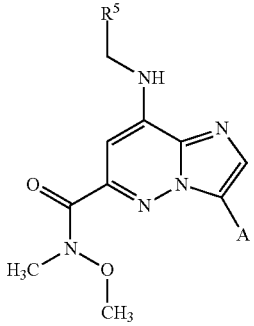

XIX in which $R^5$ and A are as defined for general formula I, supra.

In accordance with a further aspect, the present invention covers intermediate compounds of general formula XX:

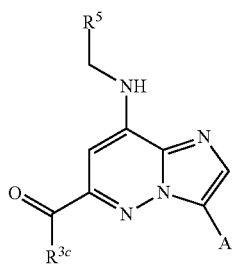

XX in which $R^5$, $R^{3c}$ and A are as defined for general formula I, supra.

In accordance with a further aspect, the present invention covers intermediate compounds of general formula XXI:

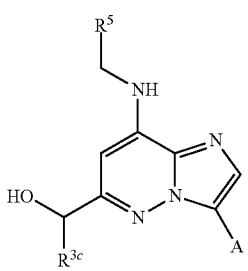

XXI in which $R^{3c}$, $R^5$ and A are as defined for general formula I, supra.

In accordance with a further aspect, the present invention covers intermediate compounds of general formula XXII:

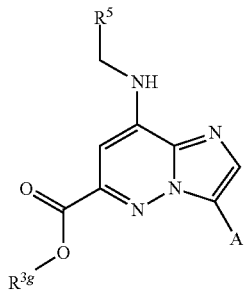

XXII in which $R^5$ and A are as defined for general formula I, supra, and $R^{3g}$ is a hydrogen atom or a $C_1$-$C_6$-alkyl- group.

In accordance with a further aspect, the present invention relates to the use of a compound of general formula II, VII, XV, XVI, XVII, XIX, XX, XXI or XXII, supra, for the preparation of a compound of general formula I, supra.

EXPERIMENTAL SECTION

The following Table lists the abbreviations used in this paragraph, and in the Examples section.

| Abbreviation | Meaning |
| --- | --- |
| EDC | 1-Ethyl-3-(3-dimethyllaminopropyl)carbodiimide |
| DCM | dichloromethane |
| DIPEA | N,N-diisopropylethylamine |
| DMF | N,N-Dimethylformamide |
| DMSO | Dimethyl sulfoxide |
| Pd(dppf)Cl$_2$ | Dichloro[1,1'-bis(diphenylphosphino)ferrocene]palladium(II) |
| P(oTol)$_3$ | tri-o-tolylphosphine |
| NMR | nuclear magnetic resonance spectroscopy |
| rt | Room temperature |
| RT | Retention time in minutes |
| MW | molecular weight |
| NMP | N-methylpyrrolidinone |
| Oxone | Potassium peroxymonosulfate |
| UPLC | ultra performance liquid chromatography |

Synthesis of Compounds of General Formula I of the Present Invention

Compounds of general formula I can be synthesized as depicted in Scheme 1 and Scheme 2, with A, $R^3$, $R^{3a}$, $R^{3b}$, $R^{3c}$, $R^{3d}$, $R^{3e}$, $R^5$ having the meaning as given for general formula I, supra;

$R^{3f}$, $R^{3g}$ represent, independently from each other, a hydrogen atom or a $C_1$-$C_3$-alkyl- group;

$R^{3'}$, $Q^2$ represent leaving groups; and $Q^1$ represents an optionally protected $NH_2$— group or a leaving group.

Examples for typical leaving groups include but are not limited to halogen atoms like a chlorine, bromine or iodine atom, or a methylsulfonyl- group, or a triflate- or nonaflate- group.

Scheme 1

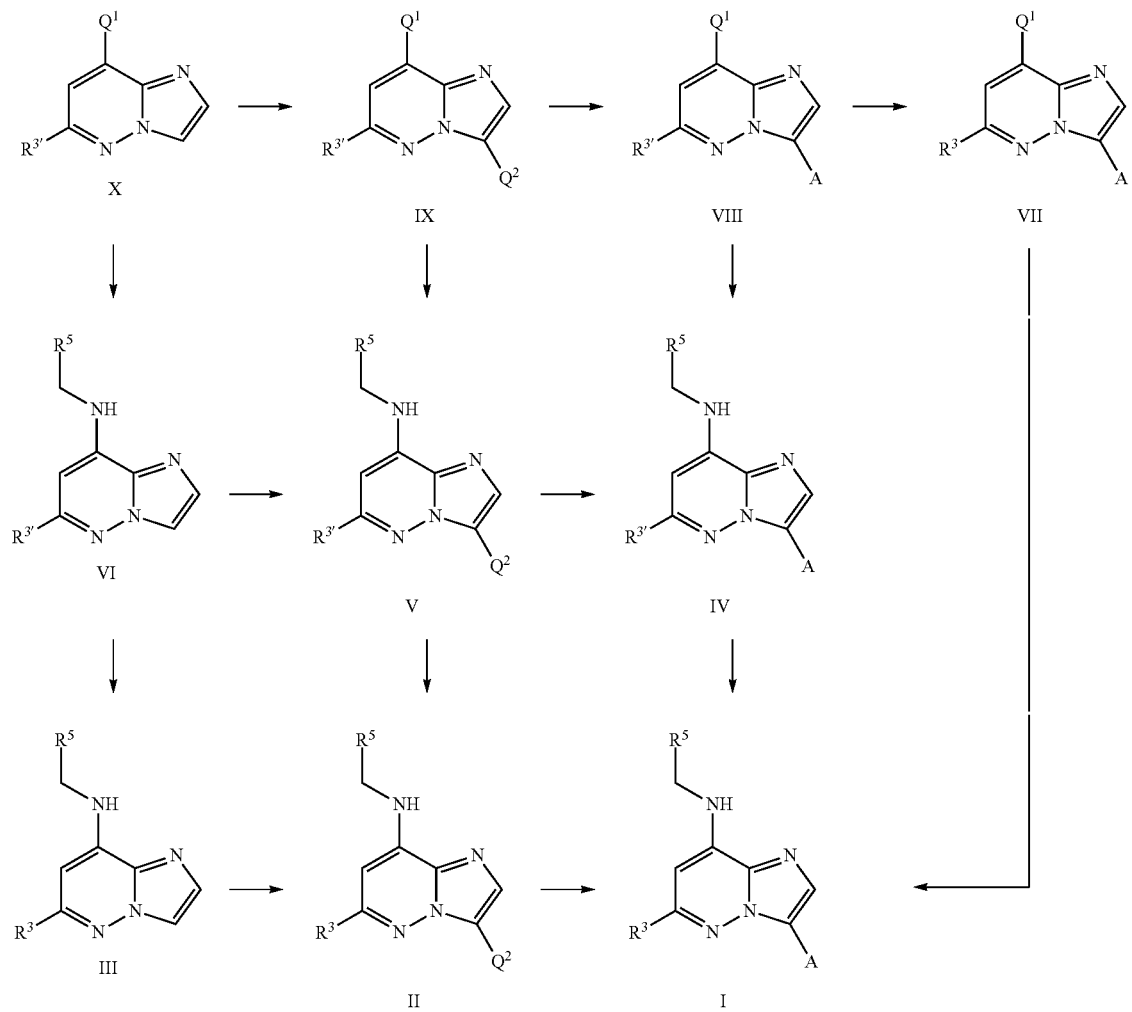

Scheme 1 exemplifies routes that allow variations for $R^3$, $R^{3'}$, $R^5$, $Q^1$, $Q^2$ and A during the synthesis. Functional moieties in $R^3$, $R^{3'}$, $R^5$, $Q^1$, $Q^2$ and A can be converted at every suitable stage of the synthesis.

However, also other routes were used for synthesis of the target compounds.

Compounds of formula X may be commercially available or can be synthesized according to procedures known to persons skilled in the art, for example applying procedures described in WO200738314A2.

A leaving group $Q^2$ can be introduced in compounds of general formula X, VI or III by procedures known to persons skilled in the art to give compounds of general formula IX, V or II. As an example, halogens can be introduced using halogenation reagents like N-iodosuccinimide (NIS), N-bromosuccinimide (NBS), or N-chlorosuccinimide (NCS), in an inert solvent like N,N-dimethylformamide or 1-methyl-pyrrolidin-2-one, for example, at temperatures ranging from room temperature to the boiling point of the solvent, for example.

Compounds of general formula I, IV or VIII can be obtained from compounds of general formula II, V or IX via a coupling reaction between a reagent of formula Y-A, in which A is defined supra and Y represents a suitable functional group by which the group A can be transferred to the Q- group bearing carbon atom of compounds of formula II, V or IX. Examples of suitable functional groups for Y in A-Y include boronic acids A-B(OH)$_2$, or esters of boronic acids A-B(OC$_1$-C$_6$-alkyl)$_2$. Said coupling reactions are performed in the presence of suitable catalysts, such as, for example, palladium based catalysts like, for example, Palladium (II) acetate, tetrakis(triphenylphosphine)palladium (0), bis(triphenylphosphine)-palladium (II) chloride or (1,1,-bis(diphenylphosphino)ferrocene)-dichloropalladium (II) and optionally suitable additives such as, for example, phosphines like, for example, P(oTol)$_3$ or triphenylphosphine and optionally with a suitable base, such as, for example, potassium carbonate, sodium 2-methylpropan-2-olate, tetrabutylammonium fluoride or tribasic potassium phosphate in a suitable solvent, such as, for example, tetrahydrofuran.

Examples of such coupling reactions may be found in the textbook entitled "Metal-Catalyzed Cross-Coupling Reactions", Armin de Meijere (Editor), François Diederich (Editor) September 2004, Wiley Interscience ISBN: 978-3-527-30518-6.

Compounds of general formula I, II, III or VII can be obtained from compounds of general formula IV, V, VI or VIII via a coupling reaction using a reagent of formula Y—R³ in which R³ is defined supra and Y represents an acidic hydrogen that can be removed by suitable bases, for example sodium hydride, in a suitable solvent, such as DMSO or tetrahydrofuran at temperatures ranging from rt to the boiling point. The resulting nucleophiles, like, for example, carbon anion bearing groups can be used to replace R³' in compounds of general formula IV, V, VI or VIII to add carbon-atom attached groups to give compounds of general formula I, II, III or VII.

Y in Y—R³ may also represent cationic moieties, like, for example, lithium cations or magnesium cations.

In the case Q¹ represents a leaving group, the introduction of a R⁵—CH₂— group can be achieved by nucleophilic substitution of Q¹ in compounds of formula VII, VIII, IX or X i.e. by a reaction with suitable amines R⁵—CH₂—NH₂ in the presence of a suitable base, such as, for example DIPEA in a suitable solvent such as N,N-dimethylformamide or 1-methylpyrrolidin-2-one, at temperatures ranging from room temperature to the boiling point of the solvent to give amines of general formula I, IV, V or VI.

In the case Q¹ represents a leaving group, the introduction of a R⁵—CH₂— group can also be achieved in a coupling reaction in which Q¹ in compounds of formula VII, VIII, IX or X is reacted with suitable amines R⁵—CH₂—NH₂ optionally in the presence of a suitable catalyst, such as Pd₂ dba₃ and BINAP for example, and optionally with a suitable base, such as, for example, sodium tert-butylate in a suitable solvent, such as, for example, N,N-dimethylformamide or 1-methylpyrrolidin-2-one to give amines of general formula I, IV, V or VI.

In the case Q¹ represents an optionally protected NH₂— group the introduction of a R⁵—CH₂— group, after deprotection to a NH₂— group, can be achieved by a reductive amination reaction using an aldehyde of formula O=CHR⁵, a suitable reducing agent, for example sodium tris(acetato-kappaO)(hydrido)borate or sodium cyanoborohydride in a suitable solvent like, for example, acetic acid at reaction temperatures ranging from room temperature to the boiling point of the solvent.

Scheme 2 exemplifies alternative routes that allow variations of R³ as last step during the synthesis. Functional moieties in R³, R⁵ and A can be converted at every suitable stage of the synthesis. Moreover, introduction of R³ via the exemplified routes is also possible at other stages of the synthesis.

Scheme 2

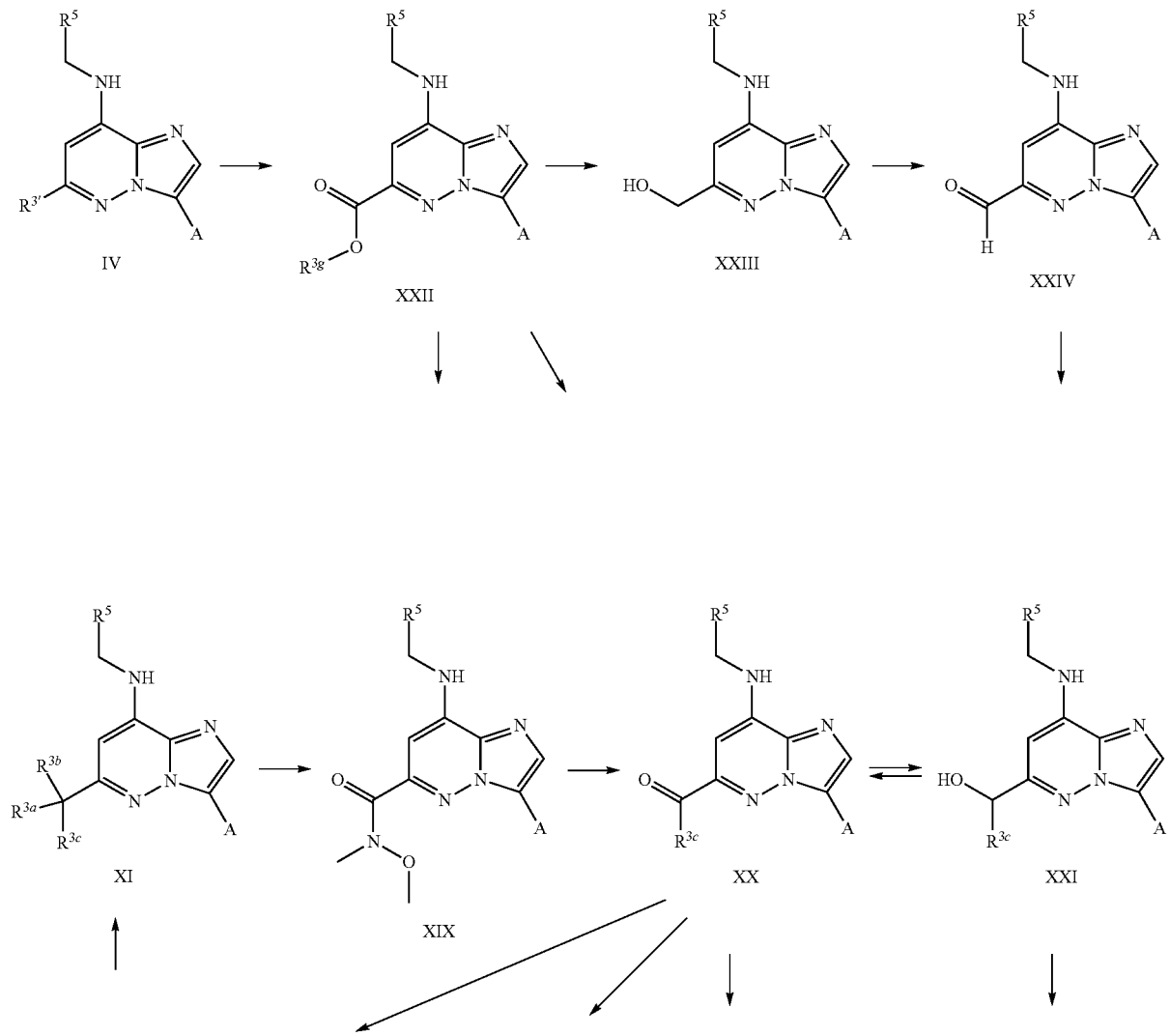

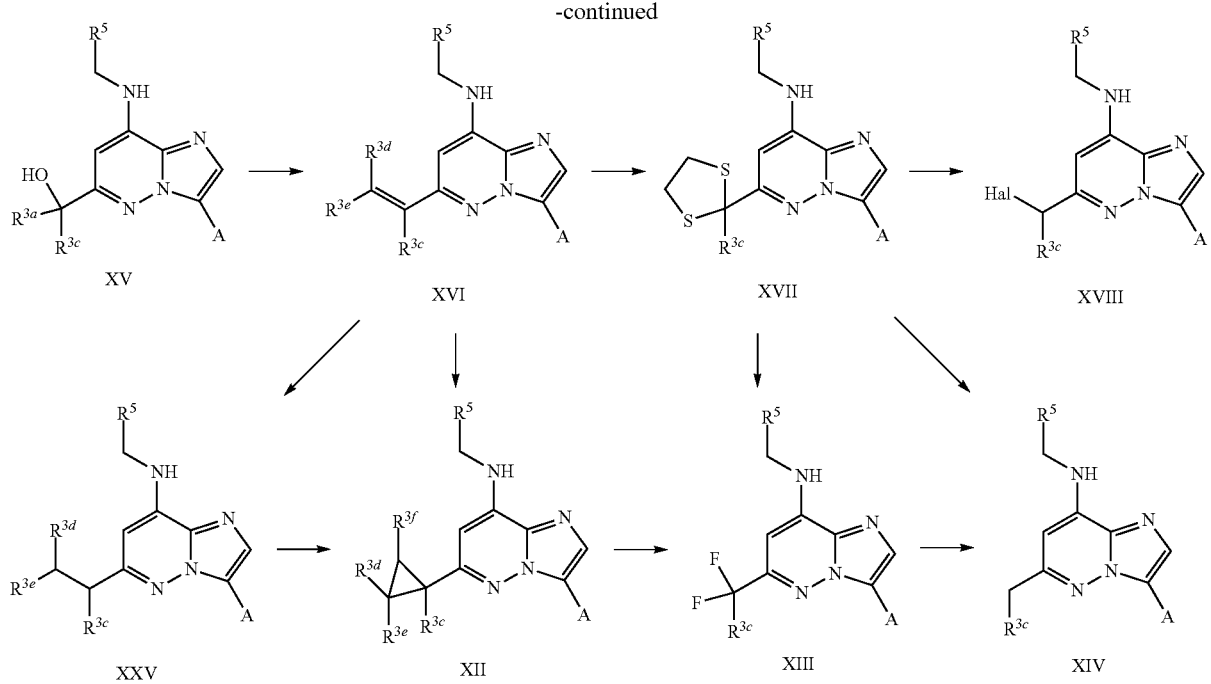

Briefly, a suitably 6-substituted imidazopyridazine intermediate of general formula IV is converted to the corresponding carboxylic acid or carboxylic ester of general formula XXII by reaction with carbon monoxide and water or an alcohol, for example methanol or ethanol in the presence of a suitable catalyst system, preferentially a palladium based catalyst like 1,1'-bis(diphenylphosphino)ferrocen-palladium(II)chloride dichloromethane complex, and a suitable base, like triethylamine or cesium carbonate in a suitable solvent, like THF at pressures ranging from atmospheric pressure up to 50 bar and at temperatures ranging from room temperature to the boiling point of the solvent. Examples of suitable leaving groups are halides like chlorine, bromine or iodine.

Conversion of the ester XXII to the corresponding alcohol intermediate XXIII is performed by a suitable reduction agent, like, for example, diisobutylaluminiunihydride or lithium aluminiumhydride or lithium trialkoxyaluminium hydride, in a suitable solvent like, for example, THF at reaction temperatures ranging from −78° C. to the boiling point of the solvent.

The alcohol intermediate XXIII can be selectively oxidized to aldehyde intermediate XXIV by a suitable oxidation method, like, for example, the use of TPAP/NMO or the Swern method using oxalylchloride and DMSO, in a suitable solvent like, for example, DCM at reaction temperatures ranging from −78° C. to the boiling point of the solvent.

Conversion of the aldehyde XXIV to an alcohol derivative XXI is performed by reaction with a suitable organometallic agent, like, for example, a Grignard reagent or an aryl-lithium compound, in a suitable solvent like, for example, THF at reaction temperatures ranging from −78° C. to the boiling point of the solvent. Grignard reagents may be commercially available or can be generated by various methods, for example by reaction of an organic bromide with magnesium or an organic magnesium salt like isopropylmagnesium chloride.

Conversion of the alcohol XXI to the corresponding carbonyl derivative XX is performed using a suitable oxidation method, like, for example, the Swern or TPAP/NMO method as described for the oxidation of XXIII. Alternatively, the reduction of the carbonyl compound XX to an alcohol XXI can be accomplished with suitable reduction agents, like for example, sodium borohydride, in a suitable solvent, like for example, methanol, at temperatures ranging from −40° C. to the boiling point of the solvent.

Alternatively, ester XXII can also be converted to the corresponding Weinreb amide intermediate XIX using, for example, N-methoxymethanamine hydrochloride (1:1) in presence of a suitable reagent, like for example isopropylmagnesium chloride or trimethyl aluminium in a suitable solvent like, for example, THF at reaction temperatures ranging from −78° C. to the boiling point of the solvent.

The Weinreb intermediate XIX can be transformed to the corresponding keto derivative XX using a suitable organometallic agent, like, for example, a Grignard reagent, in a suitable solvent like, for example, THF at reaction temperatures ranging from −78'C to the boiling point of the solvent.

Tertiary alcohol XV can be obtained from carbonyl compound XX using a suitable organometallic agent, like, for example, a Grignard reagent or an alkyl lithium reagent like methyl lithium, in a suitable solvent like, for example, THF at reaction temperatures ranging from −78° C. to the boiling point of the solvent.

Further conversion of alcohol XV to XI ($R^{3b}$=C-substituent) is performed by transformation of the alcohol group to a leaving group, like a tosylate, triflate, mesylate or nonaflate group and subsequent substitution of this group with a suitable reactant, like an organometallic agent. Subsequent substitution of the leaving group with a hydrogenating agent, like for example sodium hydride, yields the hydrogen substituted compound XI ($R^{3b}$=H-substituent)

Compounds XVI can be obtained from carbonyl compounds XX by a Wittig- or Wittig-Horner-type reaction using the appropriate phosphorous ylene or phosphonate in a suitable solvent like, for example, THF at reaction temperatures ranging from −78° C. to the boiling point of the solvent. Phosphorous ylenes are commercially available or can be obtained by reaction of a phosphorous ylide, for example an alkyl(triphenyl)phosphonium halide with a suitable base like for example n-butyllithium or potassium t-butanolate.

Conversion of the alkene XVI to the corresponding saturated alkyl XXV can be achieved in presence of a suitable catalyst system, like palladium or platinum in a suitable solvent, like ethanol or acetic acid at pressures ranging from atmospheric pressure up to 20 bar and at temperatures ranging from room temperature to the boiling point of the solvent.

Reaction of the alkene XVI with a sulphur ylide (Corey-Chaykovsky reaction) in a suitable solvent like, for example, DMSO, at reaction temperatures ranging from −40° C. to the boiling point of the solvent yields cyclopropyl compounds XII. Sulphur ylides may be commercially available or can be obtained by reaction of an appropriate trialkylsulfoxonium halide with a suitable base, like for example sodium hydride.

Compounds XX can be converted to bis-alkylsulfanyl or alkylenesulfanyl compounds XVII by reaction with a suitable thiol, for example ethanethiol or ethane-1,2-dithiol, optionally in the presence of a suitable solvent and a suitable acid, like for example boron trifluoride acetic acid complex at temperatures ranging from −40° C. to the boiling point of the solvent.

For one of ordinary skill in the art it is obvious that compounds of formula XVII are not restricted to ethylene thioketals. Other alkylene thioketals are also conceivable.

Conversion of compounds XVII to compounds XIII can be achieved by reaction with a suitable fluorination reagent, like, for example tetraalkylammonium fluorides like for example tetrabuthylammonium fluotide, HF-pyridine complex, 1-Chloromethyl-4-fluoro-1,4-diazoniabicyclo[2.2.2] octane bis(tetrafluoroborate) or combinations of different fluorination reagents, in a suitable solvent, like for example DCM, at reaction temperatures ranging from −78° C. to the boiling point of the solvent.

Reduction compounds XVII to compounds XIV is performed with a suitable reducing agent like for example hydrogen in presence of a suitable catalyst like raney nickel in a suitable solvent, like ethanol at pressures ranging from atmospheric pressure up to 20 bar and at temperatures ranging from room temperature to the boiling point of the solvent, or like, for example sodium borohydride in presence of dichloronickel hexahydrate in a suitable solvent like methanol at reaction temperatures ranging from room temperature to the boiling point of the solvent.

Compounds XVIII can be obtained from compounds XXI by direct reaction with a suitable halogenation reagent, like, for example selectfluor in HF-pyridine complex in a suitable solvent, like for example DCM, at reaction temperatures ranging from −78° C. to the boiling point of the solvent. Alternatively, the hydroxy group in XXI can be converted to a leaving group, like, for example a tosylate, triflate, mesylate or nonaflate group which subsequently can be substituted with a suitable nucleophile like a halogenation reagent, as for example cesium fluoride or sodium bromide or sodium chloride to yield compounds XVIII.

Further, the compounds in Schemes 1 and 2 of the present invention can be converted to any salt as described herein, by any method which is known to the person skilled in the art. Similarly, any salt of a compound of formula I of the present invention can be converted into the free compound, by any method which is known to the person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH2 silica gel in combination with a suitable chromatographic system such as a Flashmaster II (Separtis) or an Isolera system (Biotage) and eluents such as, for example, gradients of hexane/EtOAc or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluents such as, for example, gradients of water and acetonitrile which may contain additives such as trifluoroacetic acid, formic acid or aqueous ammonia.

Examples

Analytical UPLC-MS was performed as follows:

Method A: System: UPLC Acquity (Waters) with PDA Detector und Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: % A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z General:

All reactions were run under an atmosphere of argon in degassed solvents unless stated otherwise.

Comparative Example 1

N-Cyclopropyl-4-{6-(3-fluoro-4-methoxybenzyl)-8-[(3,3,3-trifluoropropyl)amino]imidazo[1,2-b]pyridazin-3-yl}-2-methylbenzamide

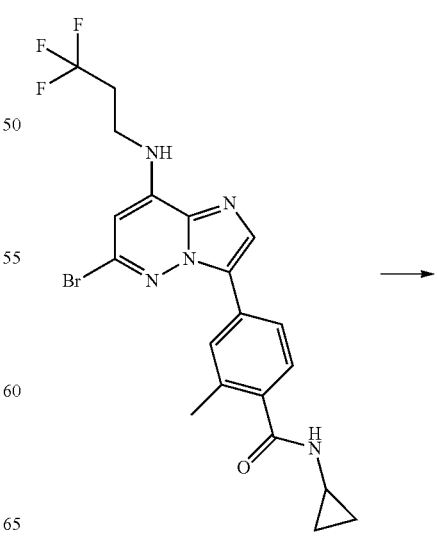

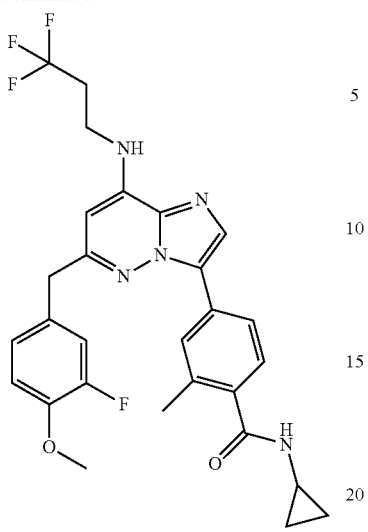

A mixture comprising 300 mg (622 μmol) 4-{6-bromo-8-[(3,3,3-trifluoropropyl)amino]imidazo[1,2-b]pyridazin-3-yl}-N-cyclopropyl-2-methylbenzamide which was prepared according to comparative example 1a, 2.0 mL tetrahydrofuran, 8.29 mL bromo(3-fluoro-4-methoxybenzyl)magnesium (0.75 M in tetrahydrofuran) was stirred at 23° C. overnight. Stirring was continued at 50° C. for 5 hours, the mixture poured into a saturated aqueous ammonium chloride solution. Water was added and the mixture extracted with ethyl acetate. The organic layer was washed with brine and dried over sodium sulfate. After filtration and removal of the solvent, the residue was purified by chromatography to give 261 mg (77%) of the title compound.

$^1$H-NMR (DMSO-d$_6$): δ=0.50 (2H), 0.65 (2H), 2.32 (3H), 2.56-2.72 (2H), 2.80 (1H), 3.53 (2H), 3.76 (3H), 3.96 (2H), 6.20 (1H), 7.04-7.12 (2H), 7.20 (1H), 7.30 (1H), 7.46 (1H), 7.92-7.98 (3H), 8.27 (1H) ppm.

Comparative Example 1a

4-{6-Bromo-8-[(3,3,3-trifluoropropyl)amino]imidazo[1,2-b]pyridazin-3-yl}-N-cyclopropyl-2-methylbenzamide

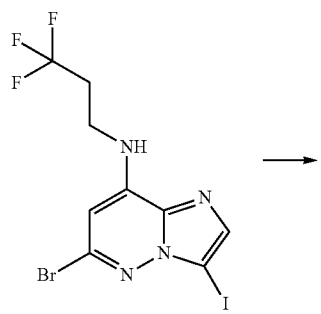 →

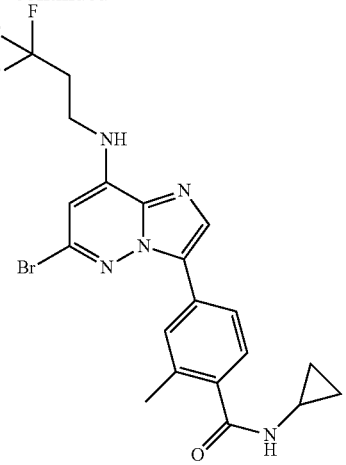

A mixture comprising 1.00 g (2.3 mmol) 6-bromo-3-iodo-N-(3,3,3-trifluoropropyl)imidazo[1,2-b]pyridazin-8-amine which was prepared according to comparative example 1b, 976 mg N-cyclopropyl-2-methyl-4-(4,4,5,5-tetramethyl-1,3,2-dioxaborolan-2-yl)benzamide which was prepared according to comparative example 1f, 564 mg (1,1,-bis(diphenylphosphino)ferrocene)-dichloropalladium (II), 3.45 mL aqueous 2M cesium carbonate solution and 15 mL tetrahydrofuran was stirred at 45° C. for 12 hours. Water was added and the mixture was extracted with ethyl acetate and methanol. The organic layer was washed with brine and dried over sodium sulfate. After filtration and removal of the solvent the residue was purified by chromatography to give 580 mg (52%) of the title compound.

Comparative Example 1b

6-Bromo-3-iodo-N-(3,3,3-trifluoropropyl)imidazo[1,2-b]pyridazin-8-amine

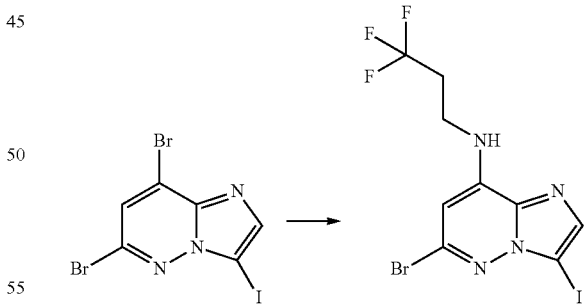

To a solution of 2.30 g (5.71 mmol) 6,8-dibromo-3-iodoimidazo[1,2-b]pyridazine which was prepared according to comparative example 1c in 40 mL N,N-dimethylformamide were added 2.0 g 3,3,3-trifluoropropan-1-amine and the mixture was stirred at 40° C. overnight. Water was added and the mixture was extracted with dichloromethane and methanol. The organic phase was washed with water and dried over sodium sulfate. After filtration and removal of solvent the residue was purified by chromatography to give 2.0 g (81%) of the title compound.

Comparative Example 1c 6,8-Dibromo-3-iodoimidazo[1,2-b]pyridazine

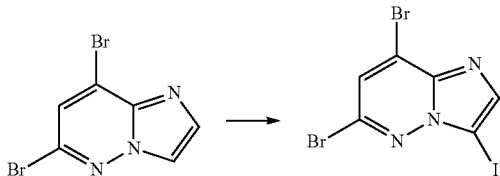 [SMILES: Brc1cc(Br)c2nccn2n1 ; Brc1cc(Br)c2ncc(I)n2n1]

A mixture comprising 3.64 g (10.5 mmol) 6,8-dibromoimidazo[1,2-b]pyridazine which was prepared according to comparative example 1d, 2.8 g N-iodosuccinimide, 72.6 mL N,N-dimethylformamide was heated at 60° C. for 3 hours. 1.4 g N-iodosuccinimide were added and heating was continued for additional 4 hours. Most of the solvent was removed, water was added and the mixture was extracted with dichloromethane. The organic phase was washed with water, sodium thiosulfate solution and dried over sodium sulfate. After filtration and removal of solvent the residue was purified by chromatography to give 3.64 g (86%) of the title compound.

Comparative Example 1d 6,8-Dibromoimidazo[1,2-b]pyridazine

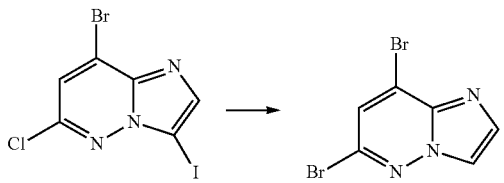 [SMILES: Clc1cc(Br)c2ncc(I)n2n1 ; Brc1cc(Br)c2nccn2n1]

A mixture of 5.0 (14.0 mmol) 8-bromo-6-chloro-3-iodoimidazo[1,2-b]pyridazine which was prepared according to comparative example 1e, 30 mL of hydrogen bromide solution (33% in acetic acid) was stirred at 120° C. for 1 hour under microwave irradiation. The mixture was poured into water and extracted with dichloromethane. The organic phase was washed with sodium thiosulfate and sodium hydrogencarbonate solution and dried over sodium sulfate. After filtration and removal of solvent the residue was purified by chromatography to give 3.0 g (78%) of the title compound.

Comparative Example 1e

8-Bromo-6-chloro-3-iodoimidazo[1,2-b]pyridazine

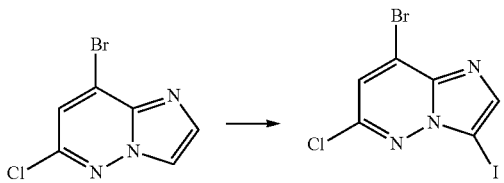 [SMILES: Clc1cc(Br)c2nccn2n1 ; Clc1cc(Br)c2ncc(I)n2n1]

A mixture comprising 100 g (430 mmol) 8-bromo-6-chloroimidazo[1,2-b]pyridazine which was prepared according to a procedure described in US2007/78136 (WO200738314), 145 g N-iodosuccinimide, 5 percent per weight conc. hydrochloric acid and 1 L trichloromethane was heated at reflux for 6 hours. 20 g N-iodosuccinimide were added and heating was continued for additional 3 hours. The precipitate was removed and the filtrate was washed with 1N sodium hydroxide solution, brine and dried over sodium sulfate. After filtration and removal of solvent diisopropyl ether was added and the residue was stirred at 23° C. overnight. The precipitate was filtered off and dried to give 66.6 g (43%) of the title compound.

Comparative Example 1f

N-Cyclopropyl-2-methyl-4-(4,4,5,5-tetramethyl-1,3,2-dioxaborolan-2-yl)benzamide

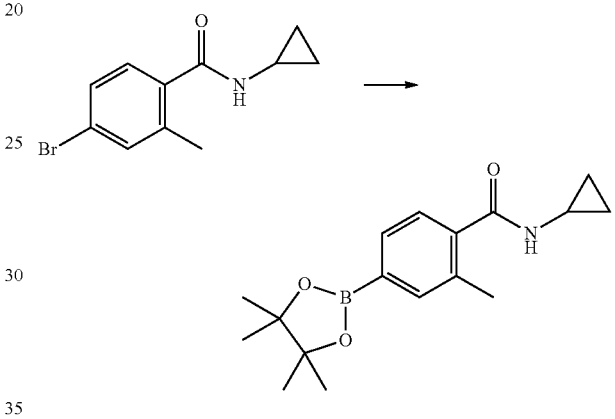

To a solution of 260 g (1.02 mol) 4-bromo-N-cyclopropyl-2-methylbenzamide which was prepared according to comparative example 1 g in 2 L dioxane at 23° C. were added 390 g bis-(pinacolato)-diboron, 19.5 g 2-dicyclohexylphosphino-2',4',6'-triisopropylbiphenyl, 150 g potassium acetate and 9.37 g tris-(dibenzylidenaceton)-dipalladium(0) and the mixture was refluxed for 6 h. After cooling to 23° C., water and ethyl acetate were added and the mixture stirred for 15 min. The organic phase was washed with water, dried over sodium sulfate, filtered and evaporated. The residue was purified by chromatography to give 308 g (56%) of the title compound.

Comparative Example 1g

4-Bromo-N-cyclopropyl-2-methylbenzamide

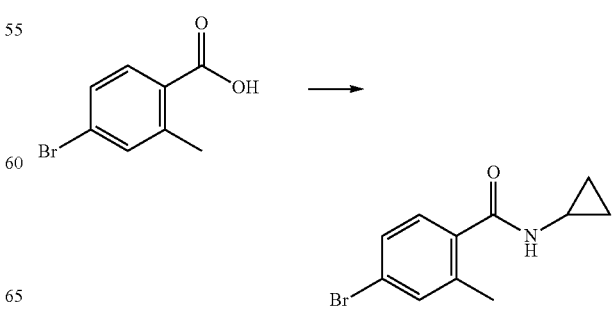

To a stirred solution of 300 g (1.4 mol) 4-bromo-2-methylbenzoic acid in 8.4 L dichloromethane at 23° C. were added 79.6 g cyclopropanamine and 320.9 g EDC. After stirring overnight, the solution was washed with water and the aqueous phase was extracted with dichloromethane. The combined organic phases were dried over sodium sulfate, filtered and evaporated. The remaining solid was triturated with diisopropyl ether, filtered, washed and dried in vacuo to yield 260 g (73%) of the title compound.

Comparative Example 2

N-Cyclopropyl-4-{6-(3-fluoro-2-hydroxybenzyl)-8-[(3,3,3-trifluoropropyl)amino]imidazo[1,2-b]pyridazin-3-yl}-2-methylbenzamide

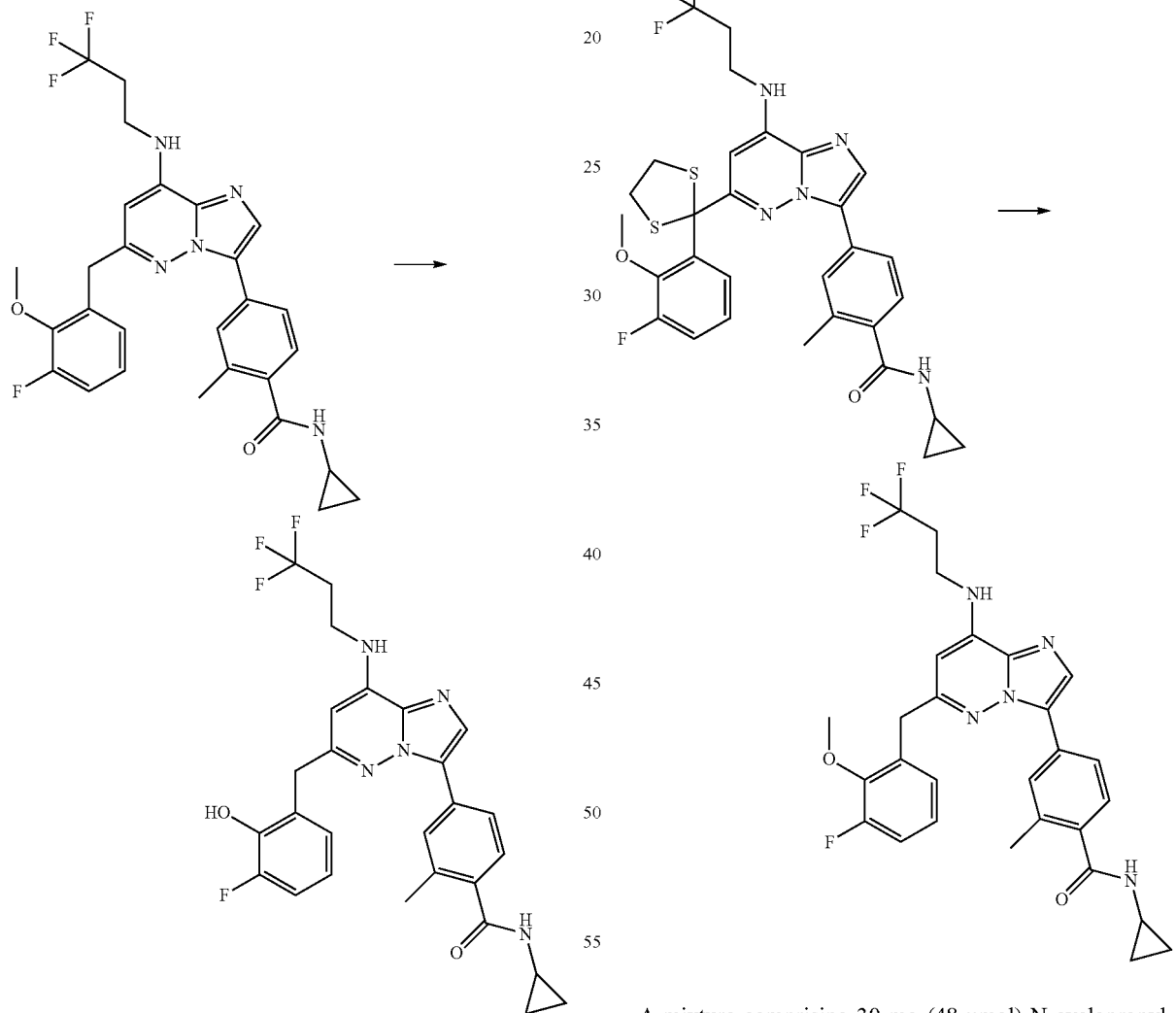

To a solution of 14.2 mg (26 μmol) N-cyclopropyl-4-{6-(3-fluoro-2-methoxybenzyl)-8-[(3,3,3-trifluoropropyl)amino]imidazo[1,2-b]pyridazin-3-yl}-2-methylbenzamide which was prepared according to comparative example 2a in 1 mL dichloromethane were added 131 μL of a 1M boron tribromide solution in dichloromethane and the mixture was stirred at 23° C. for 1 hour. Methanol was added and solvents were removed. The residue was purified by chromatography to give 4.9 mg (32%) of the title compound. UPLC-MS: RT=1.20 min; m/z (ES+) 528.5 [MH$^+$]; required MW=527.5.

$^1$H-NMR (DMSO-d$_6$): δ=0.49 (2H), 0.65 (2H), 2.29 (3H), 2.56-2.70 (2H), 2.80 (1H), 3.52 (2H), 4.04 (2H), 6.15 (1H), 6.74 (1H), 6.96-7.06 (2H), 7.26 (1H), 7.41 (1H), 7.88-7.96 (3H), 8.23 (1H), 8.70 (1H) ppm.

Comparative Example 2a

N-Cyclopropyl-4-{6-(3-fluoro-2-methoxybenzyl)-8-[(3,3,3-trifluoropropyl)amino]imidazo[1,2-b]pyridazin-3-yl}-2-methylbenzamide

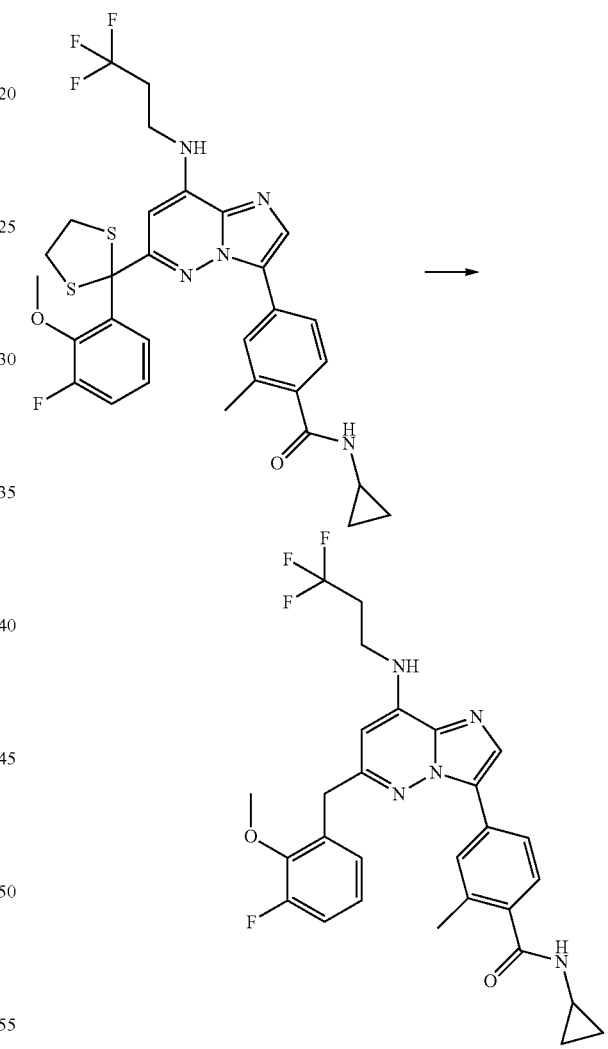

A mixture comprising 30 mg (48 μmol) N-cyclopropyl-4-{6-[2-(3-fluoro-2-methoxyphenyl)-1,3-dithiolan-2-yl]-8-[(3,3,3-trifluoropropyl)amino]imidazo[1,2-b]pyridazin-3-yl}-2-methylbenzamide which was prepared according to comparative example 2b, 800 μL methanol, 200 μL tetrahydrofuran, 18.8 mg dichloronickel hexahydrate and 15.0 mg sodium borohydride was stirred at 23° C. for 2 hours. After filtration water was added and the mixture extracted with ethyl acetate. The organic layer was washed with water and dried over sodium sulfate. After filtration and removal of the solvent, 24.2 mg (93%) of the title compound were obtained that was used without further purification. UPLC-MS: RT=1.30 min; m/z (ES+) 542.6 [MH+]; required MW=541.6.

Comparative Example 2b

N-Cyclopropyl-4-{6-[2-(3-fluoro-2-methoxyphenyl)-1,3-dithiolan-2-yl]-8-[(3,3,3-trifluoropropyl)amino]imidazo[1,2-b]pyridazin-3-yl}-2-methylbenzamide 1H-NMR (DMSO-d6): δ=0.44-0.51 (2H), 0.59-0.68 (2H), 2.58-2.72 (3H), 2.77 (1H), 3.13 (2H), 3.32-3.40 (2H), 3.42 (3H), 3.50-3.69 (4H), 6.71 (1H), 7.06 (1H), 7.17 (1H), 7.23-7.33 (1H), 7.53-7.60 (2H), 7.69 (1H), 7.83 (1H), 8.00 (1H), 8.19 (1H) ppm.

Comparative Example 2c

N-Cyclopropyl-4-{6-(3-fluoro-2-methoxybenzoyl)-8-[(3,3,3-trifluoropropyl)amino]imidazo[1,2-b]pyridazin-3-yl}-2-methylbenzamide

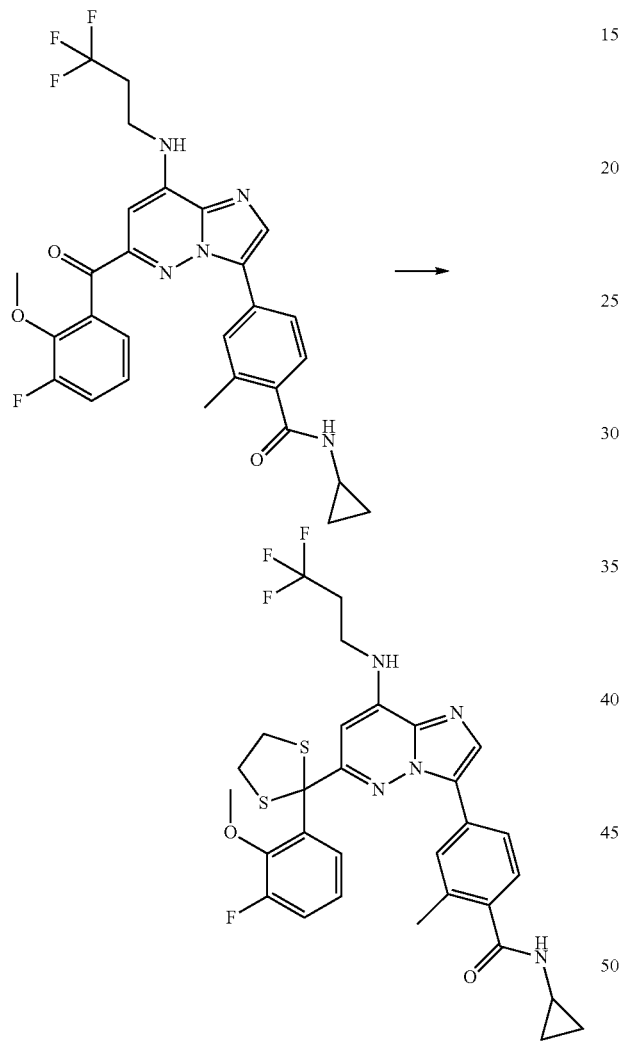

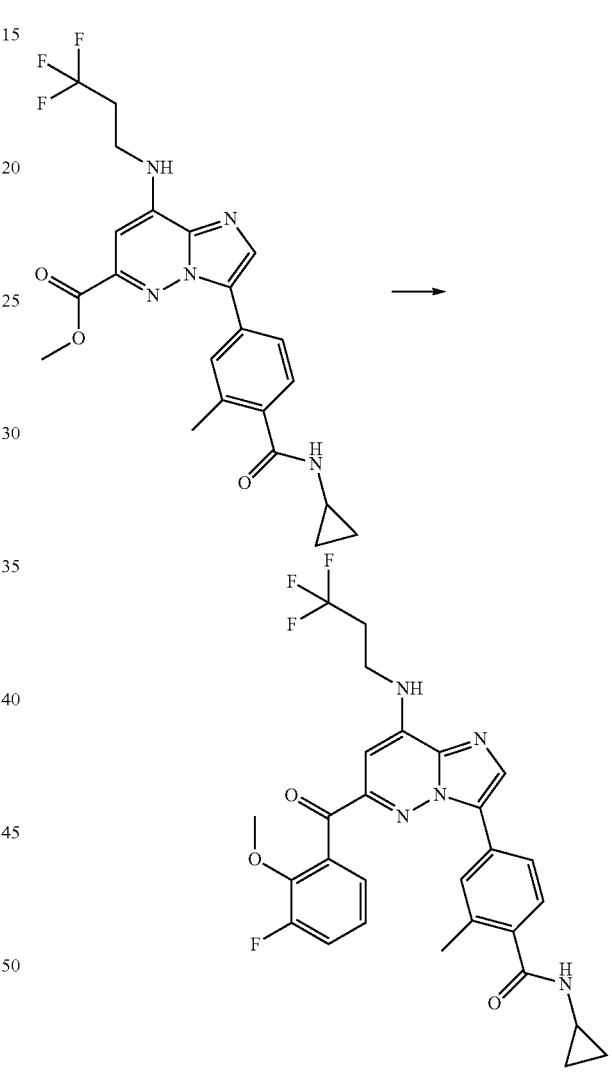

A mixture comprising 150 mg (270 μmol) N-cyclopropyl-4-{6-(3-fluoro-2-methoxybenzoyl)-8-[(3,3,3-trifluoropropyl)amino]imidazo[1,2-b]pyridazin-3-yl}-2-methylbenzamide which was prepared according to comparative example 2c, 340 μL ethane-1,2-dithiol and 37.5 μL boron trifluoride acetic acid complex was heated at 60° C. for 16 hours. Ethyl acetate was added and the mixture washed with saturated sodium hydrogen carbonate, sodium hydroxide solution (1M) and brine. The organic layer was dried over sodium sulfate. After filtration and removal of the solvent, the residue was purified by chromatography to give 63.0 mg (37%) of the title compound. UPLC-MS: RT=1.37 min; m/z (ES+) 632.7 [MH+]; required MW=631.7.

A mixture comprising 460 mg (997 mmol) methyl 3-[4-(cyclopropylcarbamoyl)-3-methylphenyl]-8-[(3,3,3-trifluoropropyl)amino]imidazo[1,2-b]pyridazine-6-carboxylate which was prepared according to comparative example 2d, 10 mL tetrahydrofuran and 126 mg N-methoxymethanamine hydrochloride was cooled to −5° C. 35.9 mL bromo(3-fluoro-2-methoxyphenyl)magnesium solution in tetrahydrofuran (0.5 M) were added, the mixture stirred at 23° C. overnight and poored into cold hydrochloric acid. Ethyl acetate was added and the mixture washed with brine. The organic layer was dried over sodium sulfate. After filtration and removal of the solvent, the residue was purified by chromatography to give 306 mg (55%) of the title compound. UPLC-MS: RT=1.30 min; m/z (ES+) 556.5 [MH+]; required MW=555.5.

$^1$H-NMR (DMSO-d$_6$): δ=0.44-0.51 (2H), 0.59-0.70 (2H), 2.10 (3H), 2.64-2.83 (3H), 3.62 (3H), 3.72 (2H), 6.79 (1H), 7.00-7.06 (1H), 7.14 (1H), 7.26 (1H), 7.50 (1H), 7.54 (1H), 7.71 (1H), 7.82 (1H), 7.94 (1H), 8.22 (1H) ppm.

Comparative Example 2d

Methyl 3-[4-(cyclopropylcarbamoyl)-3-methylphenyl]-8-[(3,3,3-trifluoropropyl)amino]imidazo[1,2-b]pyridazine-6-carboxylate

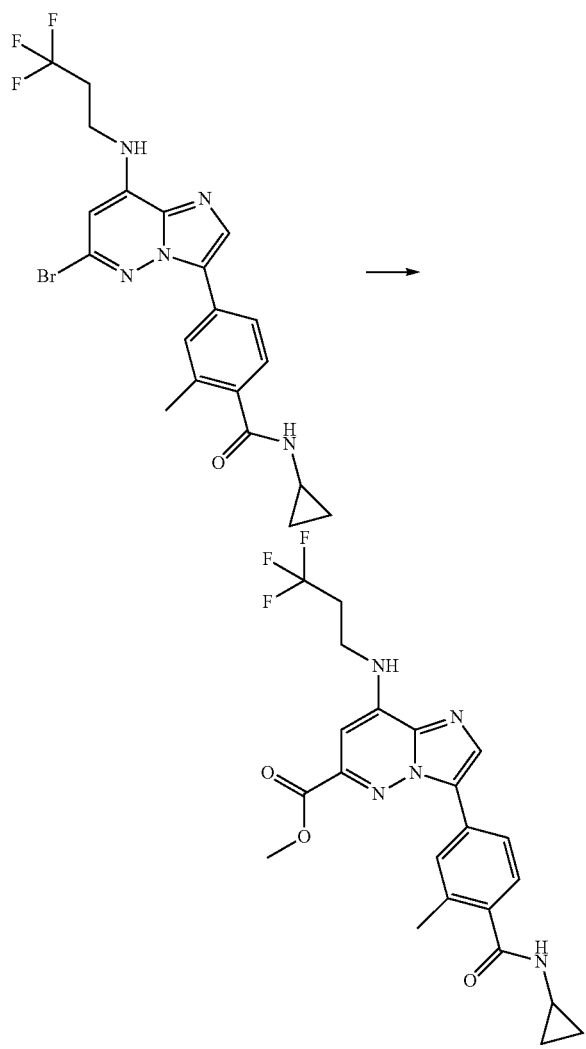

A mixture comprising 5.0 g (10.37 mmol) 4-{6-bromo-8-[(3,3,3-trifluoropropyl)amino]imidazo[1,2-b]pyridazin-3-yl}-N-cyclopropyl-2-methylbenzamide which was prepared according to comparative example 1a, 100 mL methanol, 10 mL tetrahydrofuran, 1.7 g (1,1,-bis(diphenylphosphino)ferrocene)-dichloropalladium (II), 1.6 mL triethylamine was reacted under an atmosphere of carbon monoxide at 100° C., 9-12 bar for 24 hours. After removal of the solvents, the residue was purified by chromatography to give 3.32 g (63%) of the title compound. UPLC-MS: RT=1.11 min; m/z (ES+) 462.5 [MH+]; required MW=461.5.

Comparative Example 3

N-Cyclopropyl-4-{6-(3-fluorobenzyl)-8-[(3,3,3-trifluoropropyl)amino]imidazo[1,2-b]pyridazin-3-yl}-2-methylbenzamide

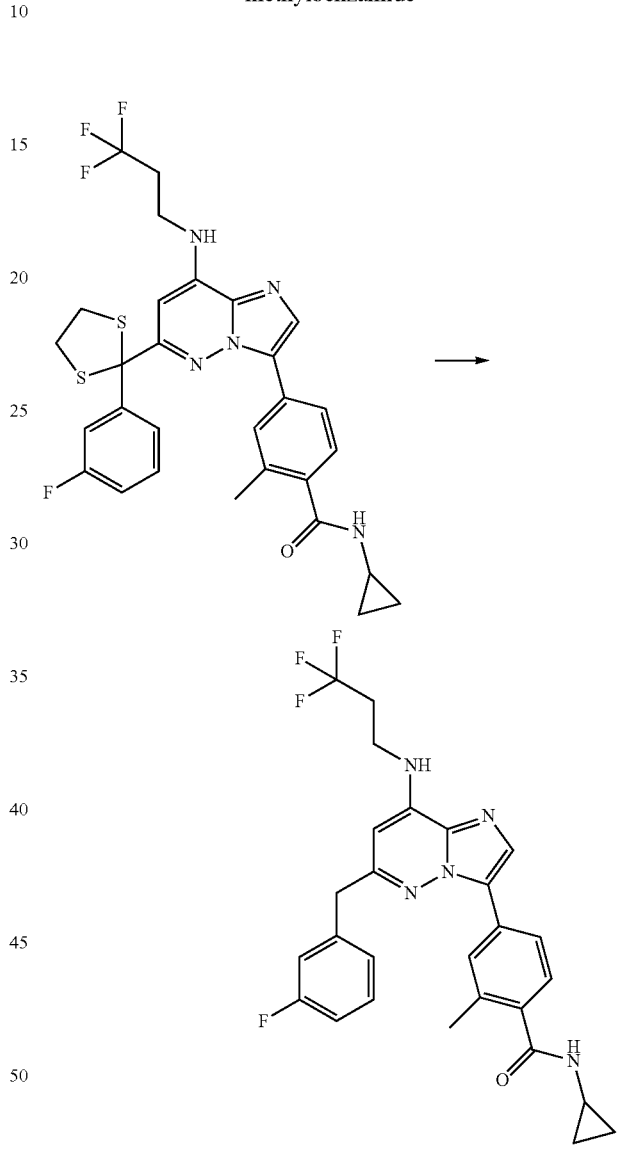

45 mg (75 μmol) N-cyclopropyl-4-{6-[2-(3-fluorophenyl)-1,3-dithiolan-2-yl]-8-[(3,3,3-trifluoropropyl)amino]imidazo[1,2-b]pyridazin-3-yl}-2-methylbenzamide which was prepared according to comparative example 3a were transformed in analogy to comparative example 2a to give after working up and purification 16.3 mg (42%) of the title compound. UPLC-MS: RT=1.30 min; m/z (ES+) 556.5 [MH+]; required MW=555.5.

$^1$H-NMR (DMSO-d$_6$): δ=0.50 (2H), 0.65 (2H), 2.32 (3H), 2.56-2.72 (2H), 2.80 (1H), 3.54 (2H), 4.05 (2H), 6.22 (1H), 7.03 (1H), 7.15-7.23 (2H), 7.26-7.38 (2H), 7.46 (1H), 7.91-7.99 (3H), 8.24 (1H) ppm.

Comparative Example 3a

N-Cyclopropyl-4-{6-[2-(3-fluorophenyl)-1,3-dithiolan-2-yl]-8-[(3,3,3-trifluoropropyl)amino]imidazo[1,2-b]pyridazin-3-yl}-2-methylbenzamide

Comparative Example 3b

N-Cyclopropyl-4-{6-(3-fluorobenzoyl)-8-[(3,3,3-trifluoropropyl)amino]imidazo[1,2-b]pyridazin-3-yl}-2-methylbenzamide

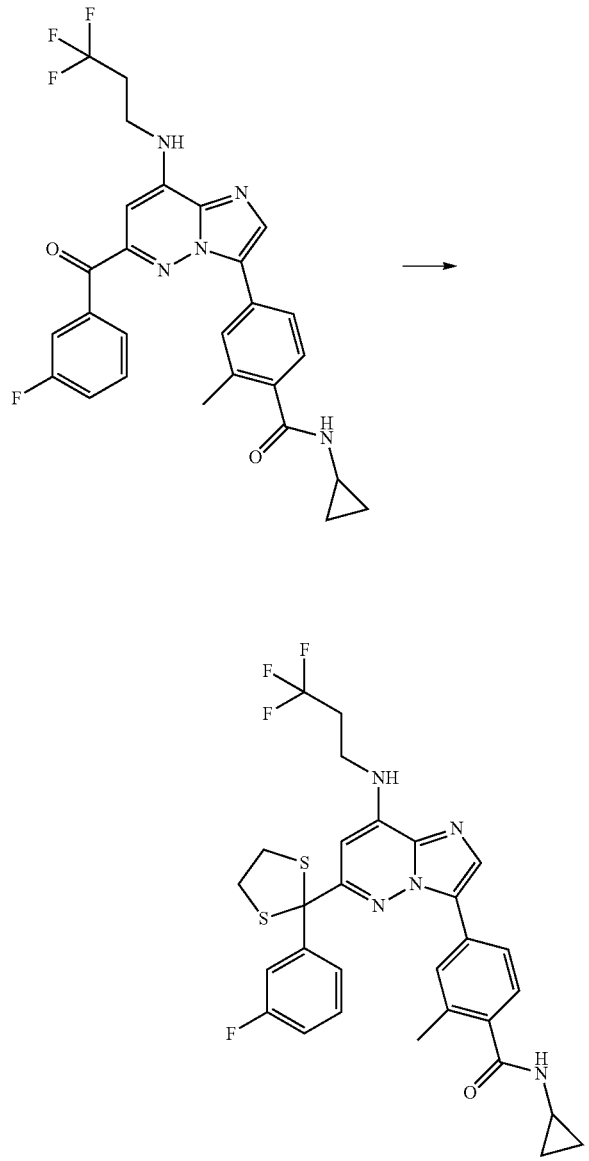 [SMILES: Cc1cc(-c2cnc3c(NCCC(F)(F)F)cc(C4(c5cc(F)ccc5F)SCCS4)nn23)ccc1C(=O)NC1CC1 ; Cc1cc(-c2cnc3c(NCCC(F)(F)F)cc(C(F)(F)c4cc(F)ccc4F)nn23)ccc1C(=O)NC1CC1]

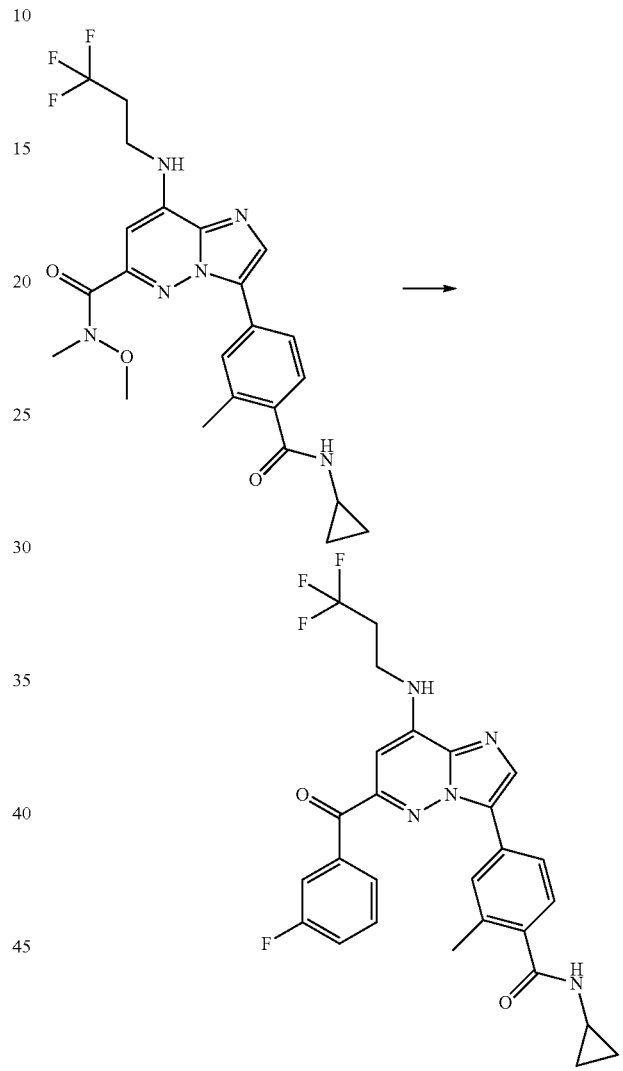

80 mg (152 μmol) N-cyclopropyl-4-{6-(3-fluorobenzoyl)-8-[(3,3,3-trifluoropropyl)amino]imidazo[1,2-b]pyridazin-3-yl}-2-methylbenzamide which was prepared according to comparative example 3b were transformed in analogy to comparative example 2b to give after working up and purification 45 mg (49%) of the title compound. UPLC-MS: RT=1.39 min; m/z (ES+) 602.7 [MH$^+$]; required MW=601.7.

$^1$H-NMR (DMSO-d$_6$): δ=0.46-0.53 (2H), 0.61-0.68 (2H), 2.30 (3H), 2.52-2.65 (2H), 2.76-2.85 (1H), 3.32-3.41 (2H), 3.48-3.62 (4H), 6.26 (1H), 7.06-7.13 (1H), 7.26 (1H), 7.34 (1H), 7.39-7.43 (1H), 7.48 (1H), 7.63 (1H), 7.91 (1H), 8.05 (2H), 8.25 (1H) ppm.

To a solution of 400 mg (0.816 mmol) 3-[4-(cyclopropylcarbamoyl)-3-methylphenyl]-N-methoxy-N-methyl-8-[(3,3,3-trifluoropropyl)amino]imidazo[1,2-b]pyridazine-6-carboxamide which was prepared according to comparative example 3c in 30 mL THF were added 12.23 mL (15 eq) bromo(3-fluorophenyl)magnesium (1M solution in THF) at −20° C. After further 30 min. stirring at this temperature, the solution is added dropwise to 50 mL ice-cold 0.5 M HCl solution to give after working up and purification 334 mg (78%) of the title compound. UPLC-MS: RT=1.32 min; m/z (ES+) 526.5 [MH$^+$]; required MW=525.5.

$^1$H-NMR (DMSO-d$_6$): δ=0.44-0.52 (2H), 0.59-0.69 (2H), 2.20 (3H), 2.62-2.84 (3H), 3.70 (2H), 6.74 (1H), 7.10 (1H), 7.24 (1H), 7.51-7.66 (2H), 7.79-7.96 (4H), 8.15 (1H), 8.23 (1H) ppm.

Comparative Example 3c

3-[4-(cyclopropylcarbamoyl)-3-methylphenyl]-N-methoxy-N-methyl-8-[(3,3,3-trifluoropropyl)amino]imidazo[1,2-b]pyridazine-6-carboxamide

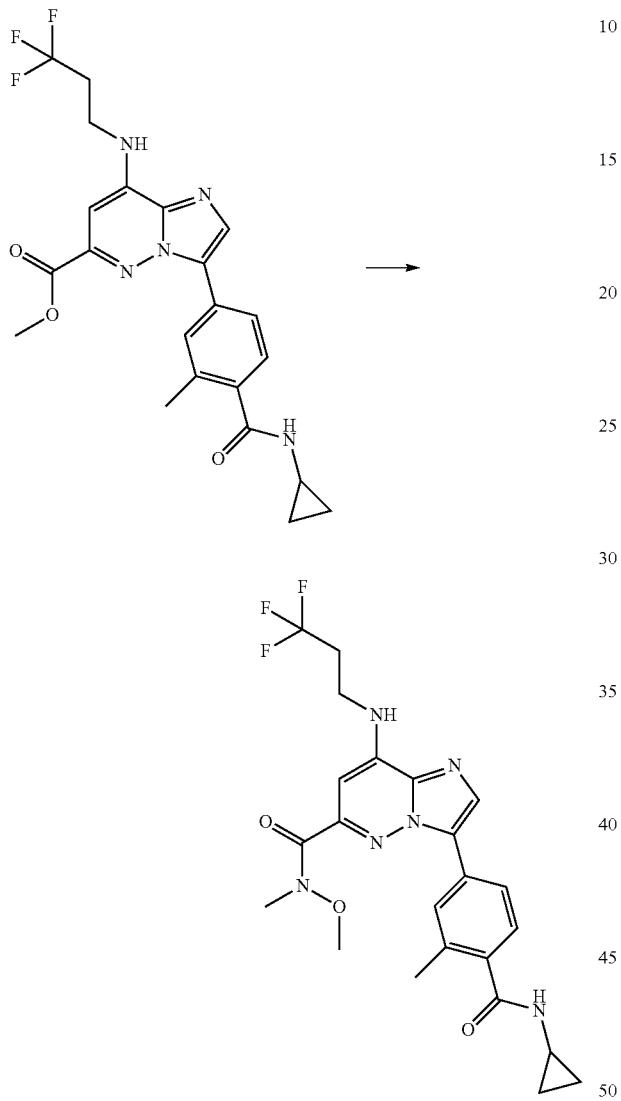

To a suspension of 6.62 g (14.34 mmol) methyl 3-[4-(cyclopropylcarbamoyl)-3-methylphenyl]-8-[(3,3,3-trifluoropropyl)amino]imidazo[1,2-b]pyridazine-6-carboxylate which was prepared according to comparative example 2d and 2.10 g (21.52 mmol) N-methoxymethanamine hydrochloride (1:1) in 30 mL THF were dropwise added 33 mL lithium chloride-chloro(propan-2-yl)magnesium (1:1) (3 eq, 1.3M solution in THF) at −20° C. After 2 h stirring at this temperature, further 55 mL (5 eq) mL lithium chloride-chloro(propan-2-yl)magnesium (1:1) solution were added. After 40 min the reaction is quenched by addition of 20% ammonia chloride solution to give after working up and purification 3.8 g (55%) of the title compound. UPLC-MS: RT=1.05 min; m/z (ES+) 491.5 [MH+]; required MW=490.5.

$^1$H-NMR (DMSO-d$_6$): δ=0.44-0.53 (2H), 0.60-0.69 (2H), 2.35 (3H), 2.57-2.73 (2H), 2.81 (1H), 3.54-3.69 (5H), 6.36 (1H), 7.36 (1H), 7.81 (1H), 7.90 (1H), 7.95 (1H), 8.04 (1H), 8.28 (1H) ppm. comparative

Comparative Example 4

N-cyclopropyl-4-{6-(3-methoxybenzyl)-8-[(3,3,3-trifluoropropyl)amino]imidazo[1,2-b]pyridazin-3-yl}-2-methylbenzamide

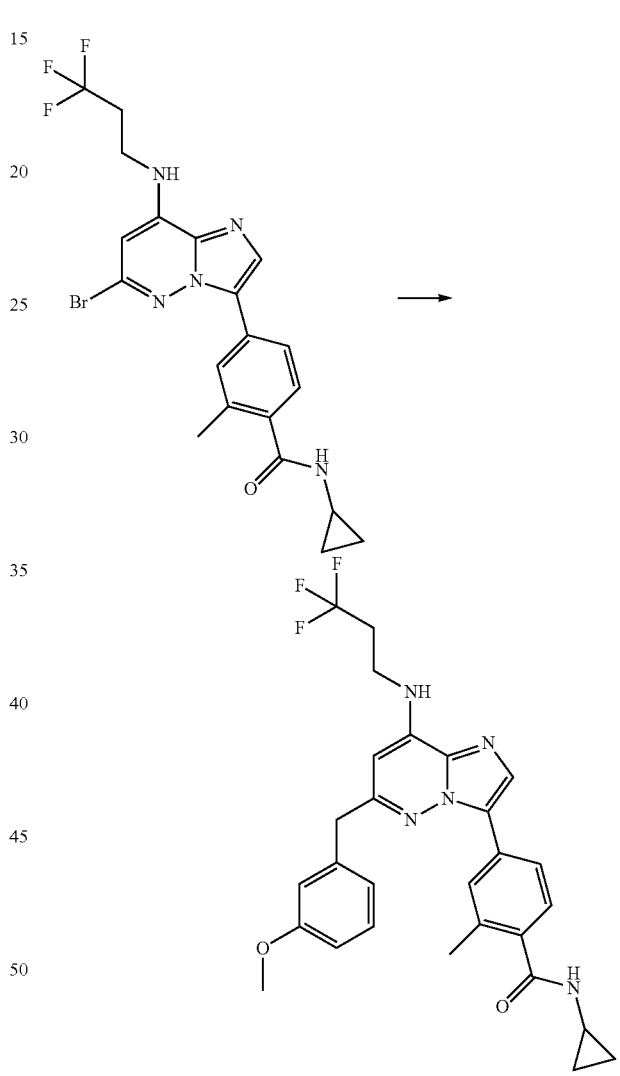

100 mg (207 μmol) 4-{6-bromo-8-[(3,3,3-trifluoropropyl)amino]imidazo[1,2-b]pyridazin-3-yl}-N-cyclopropyl-2-methylbenzamide which was prepared according to comparative example 1a were transformed in analogy to comparative example 1 using bromo(3-methoxybenzyl)magnesium to give after working up and purification 28.7 mg (25%) of the title compound.

$^1$H-NMR (DMSO-d$_6$): δ=0.50 (2H), 0.65 (2H), 2.33 (3H), 2.56-2.72 (2H), 2.80 (1H), 3.53 (2H), 3.69 (3H), 3.99 (2H), 6.28 (1H), 6.77 (1H), 6.87-6.97 (2H), 7.20 (1H), 7.32 (1H), 7.54 (1H), 7.93-8.05 (3H), 8.28 (1H) ppm.

Comparative Example 5

N-Cyclopropyl-4-{6-(4-methoxybenzyl)-8-[(3,3,3-trifluoropropyl)amino]imidazo[1,2-b]pyridazin-3-yl}-2-methylbenzamide

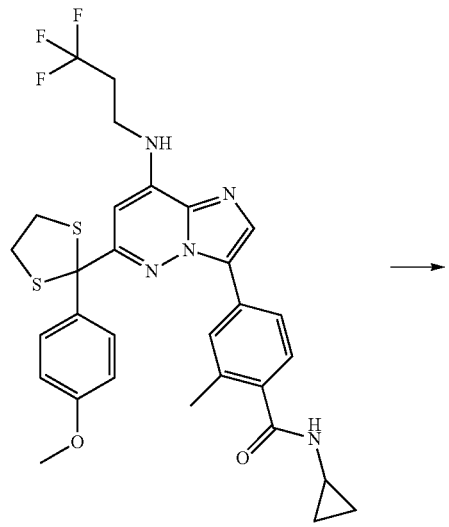

→

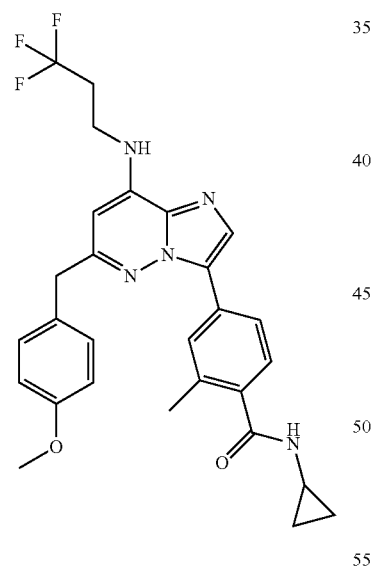

30 mg (49 μmol) N-cyclopropyl-4-{6-[2-(4-methoxyphenyl)-1,3-dithiolan-2-yl]-8-[(3,3,3-trifluoropropyl)amino]imidazo[1,2-b]pyridazin-3-yl}-2-methylbenzamide which was prepared according to comparative example 5a were transformed in analogy to comparative example 2a to give after working up and purification 7.9 mg (29%) of the title compound.

$^1$H-NMR (DMSO-d$_6$): δ=0.50 (2H), 0.65 (2H), 2.33 (3H), 2.55-2.71 (2H), 2.80 (1H), 3.52 (2H), 3.68 (3H), 3.94 (2H), 6.16 (1H), 6.85 (2H), 7.25 (2H), 7.31 (1H), 7.43 (1H), 7.91-8.01 (3H), 8.27 (1H) ppm.

Comparative Example 5a

N-Cyclopropyl-4-{6-[2-(4-methoxyphenyl)-1,3-dithiolan-2-yl]-8-[(3,3,3-trifluoropropyl)amino]imidazo[1,2-b]pyridazin-3-yl}-2-methylbenzamide

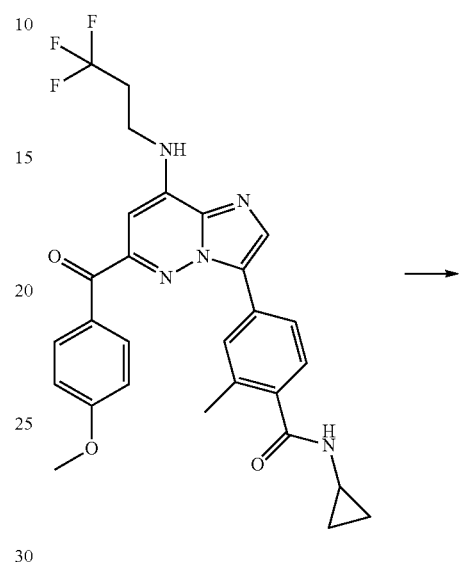

→

100 mg (186 μmol) N-cyclopropyl-4-{6-(4-methoxybenzoyl)-8-[(3,3,3-trifluoropropyl)amino]imidazo[1,2-b]pyridazin-3-yl}-2-methylbenzamide which was prepared according to example 9 were transformed in analogy to comparative example 2b to give after working up and purification 60.2 mg (53%) of the title compound.

Example 1

N-Cyclopropyl-4-{6-[1-(3-fluoro-4-methoxyphenyl)ethenyl]-8-[(3,3,3-trifluoropropyl)amino]imidazo[1,2-b]pyridazin-3-yl}-2-methylbenzamide

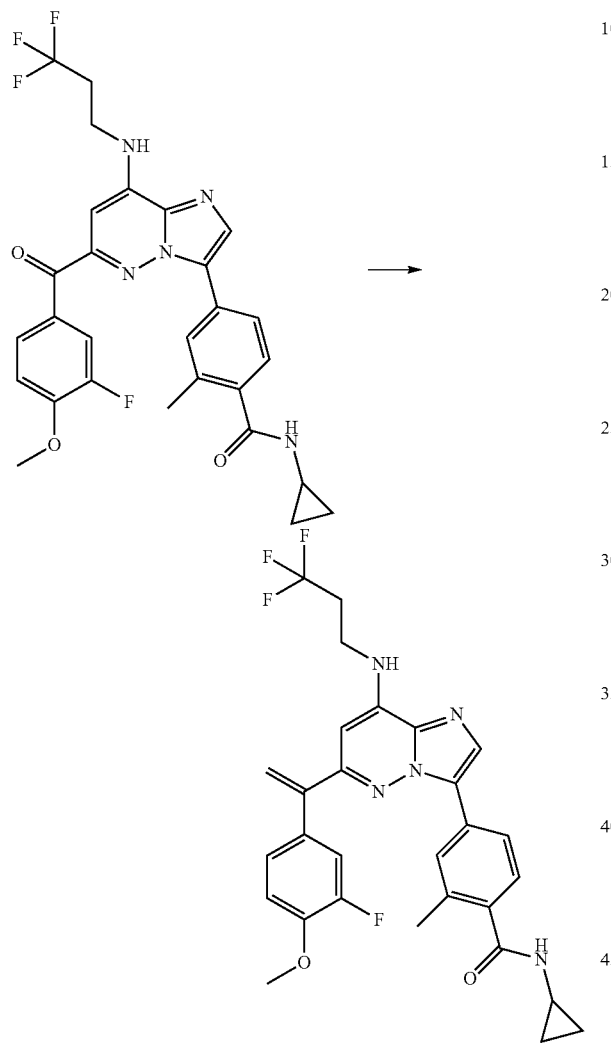

To a suspension of 386 mg methyl(triphenyl)phosphonium bromide in 6.8 mL tetrahydrofuran at −78° C. were added 421 µL n-butyllithium (2.5M in hexane). After the mixture was stirred at 0° C. for 0.5 hours a solution of 150 mg (270 µmol) N-cyclopropyl-4-{6-(3-fluoro-4-methoxybenzoyl)-8-[(3,3,3-trifluoropropyl)amino]imidazo[1,2-b]pyridazin-3-yl}-2-methylbenzamide which was prepared according to intermediate example 1a in 3.2 mL tetrahydrofuran was added and stirring was continued overnight. Water was added and the mixture was extracted with ethyl acetate. The organic layer was washed with saturated ammonium chloride solution and dried over sodium sulfate. After filtration and removal of the solvent the residue was purified by chromatography to give 127 mg (81%) of the title compound.

¹H-NMR (DMSO-$d_6$): δ=0.48 (2H), 0.64 (2H), 2.17 (3H), 2.61-2.73 (2H), 2.78 (1H), 3.61 (2H), 3.84 (3H), 5.73 (1H), 5.93 (1H), 6.36 (1H), 7.13-7.23 (3H), 7.30 (1H), 7.54 (1H), 7.82 (1H), 7.88 (1H), 8.01 (1H), 8.21 (1H) ppm.

Intermediate Example 1a

N-Cyclopropyl-4-{6-(3-fluoro-4-methoxybenzoyl)-8-[(3,3,3-trifluoropropyl)amino]imidazo[1,2-b]pyridazin-3-yl}-2-methylbenzamide

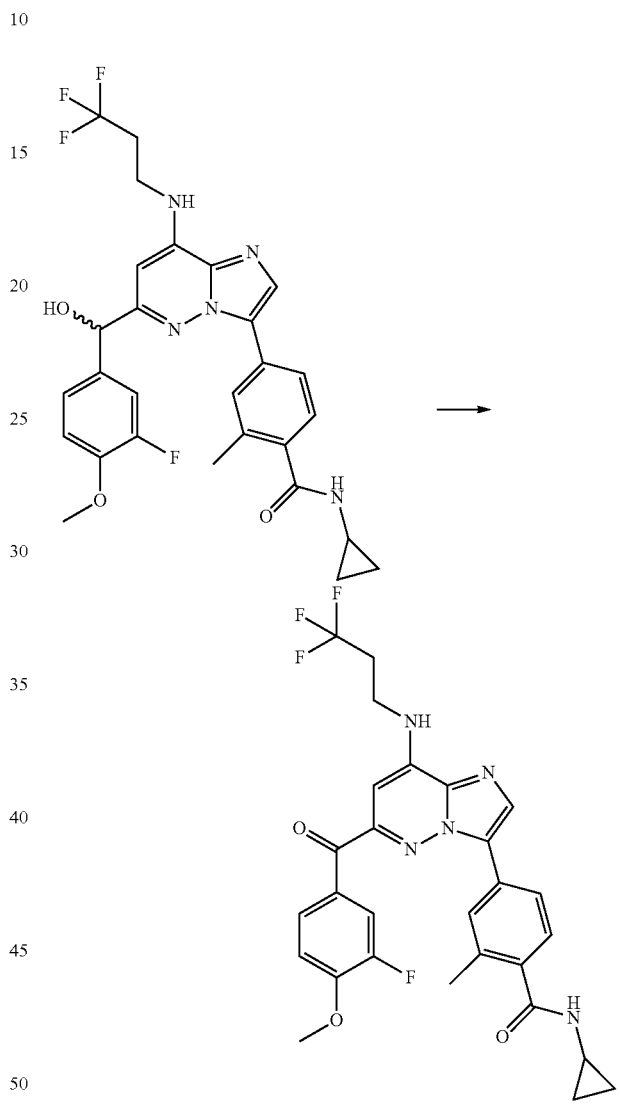

To a solution of 82 µL ethanedioyl dichloride in 2.5 mL dichloromethane were added at −78° C. 133 µL dimethyl sulfoxide followed by a solution of 262 mg (470 µmol) (RS)—N-cyclopropyl-4-{6-[(3-fluoro-4-methoxyphenyl)(hydroxy)methyl]-8-[(3,3,3-trifluoropropyl)amino]imidazo[1,2-b]pyridazin-3-yl}-2-methylbenzamide which was prepared according to intermediate example 1b in 2.5 mL dichloromethane and 0.6 mL dimethyl sulfoxide. After 1 hour, 393 µL triethylamine were added and the mixture was stirred at 23° C. for 20 minutes. Water was added and the mixture was extracted dichloromethane and methanol (9:1). The organic layer was washed with water and dried over sodium sulfate. After filtration and removal of the solvent the residue was purified by chromatography to give 210 mg (80%) of the title compound.

Intermediate Example 1b (RS)—N-Cyclopropyl-4-{6-[(3-fluoro-4-methoxyphenyl)(hydroxy)methyl]-8-[(3,3,3-trifluoropropyl)amino]imidazo[1,2-b]pyridazin-3-yl}-2-methylbenzamide

Intermediate Example 1c

N-Cyclopropyl-4-{6-formyl-8-[(3,3,3-trifluoropropyl)amino]imidazo[1,2-b]pyridazin-3-yl}-2-methylbenzamide

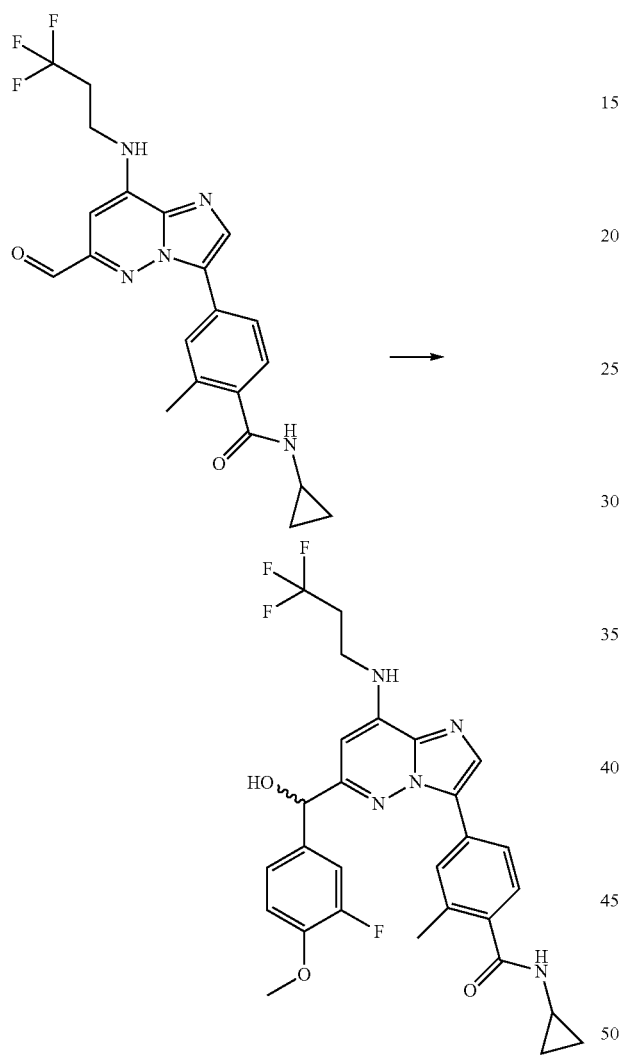

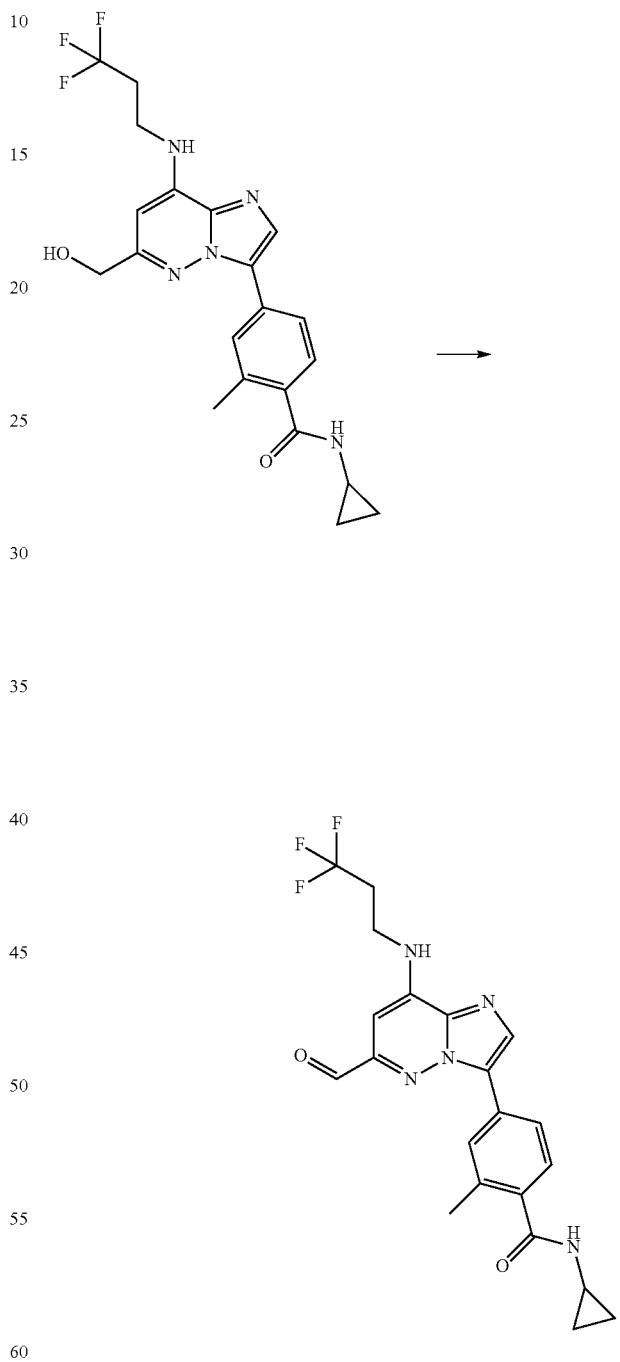

To a solution of 500 mg (1.16 mmol) N-cyclopropyl-4-{6-formyl-8-[(3,3,3-trifluoropropyl)amino]imidazo[1,2-b]pyridazin-3-yl}-2-methylbenzamide which was prepared according to intermediate example 1c in 20 mL tetrahydrofuran were added at 0° C. a solution of bromo(3-fluoro-4-methoxyphenyl)magnesium freshly prepared from 598 µL 4-bromo-2-fluoro-1-methoxybenzene, 113 mg magnesium and 5 mL tetrahydrofuran. After 1 hour the mixture was poured into a saturated aqueous ammonium chloride solution. Water was added and the mixture extracted with ethyl acetate. The organic layer was washed with brine and dried over sodium sulfate. After filtration and removal of the solvent, the residue was purified by chromatography to give 319 mg (46%) of the title compound.

1.60 g (3.69 mmol) N-cyclopropyl-4-{6-(hydroxymethyl)-8-[(3,3,3-trifluoropropyl)amino]imidazo[1,2-b]pyridazin-3-yl}-2-methylbenzamide which was prepared according to intermediate example 1d were transformed in analogy to intermediate example 1a to give after working up and purification 1.50 g (94%) of the title compound.

Intermediate Example 1d

N-Cyclopropyl-4-{6-(hydroxymethyl)-8-[(3,3,3-trifluoropropyl)amino]imidazo[1,2-b]pyridazin-3-yl}-2-methylbenzamide

Example 2

N-Cyclopropyl-4-{6-[difluoro(3-fluoro-4-methoxyphenyl)methyl]-8-[(3,3,3-trifluoropropyl)amino]imidazo[1,2-b]pyridazin-3-yl}-2-methylbenzamide

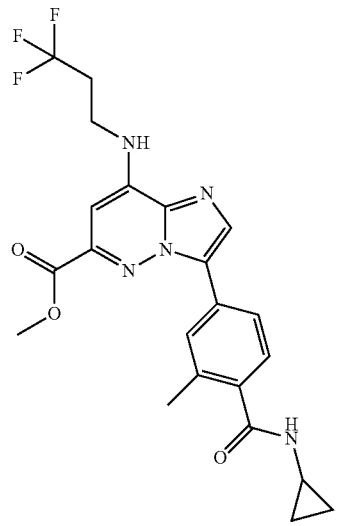

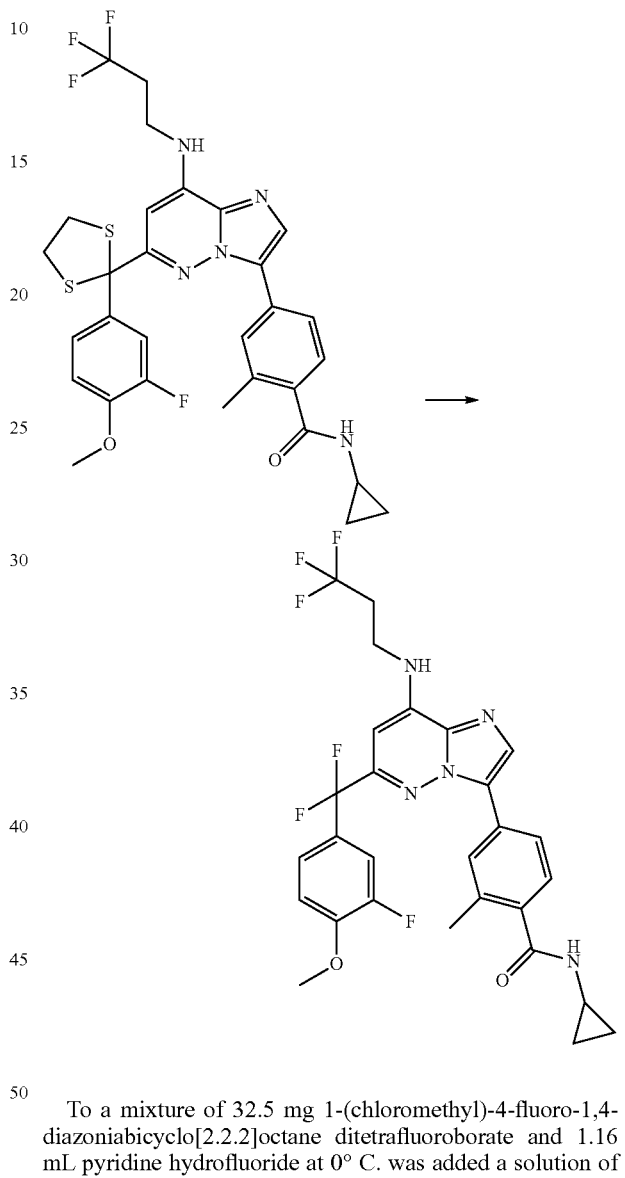

To a solution of 2.17 g (4.70 mmol) methyl 3-[4-(cyclopropylcarbamoyl)-3-methylphenyl]-8-[(3,3,3-trifluoropropyl)amino]imidazo[1,2-b]pyridazine-6-carboxylate which was prepared according to comparative example 2d in 220 mL tetrahydrofuran at 0° C. were added 23.5 mL diisobutylaluminiumhydrid solution (1M in tetrahydrofuran). After 1 hour the mixture was poured into a saturated aqueous ammonium chloride solution. Water was added and the mixture extracted with ethyl acetate and methanol (9:1). The organic layer was washed with brine and dried over sodium sulfate. After filtration and removal of the solvent, the residue was purified by chromatography to give 1.56 g (73%) of the title compound.

To a mixture of 32.5 mg 1-(chloromethyl)-4-fluoro-1,4-diazoniabicyclo[2.2.2]octane ditetrafluoroborate and 1.16 mL pyridine hydrofluoride at 0° C. was added a solution of 29 mg (46 µmol) N-cyclopropyl-4-{6-[2-(3-fluoro-4-methoxyphenyl)-1,3-dithiolan-2-yl]-8-[(3,3,3-trifluoropropyl)amino]imidazo[1,2-b]pyridazin-3-yl}-2-methylbenzamide which was prepared according to intermediate example 2a in 0.5 mL dichloromethane. The mixture was stirred at 23° C. overnight and poured into water. The organic layer was washed with water and brine and dried over sodium sulfate. After filtration and removal of the solvent, the residue was purified by chromatography to give 14.6 mg (52%) of the title compound.

$^1$H-NMR (DMSO-$d_6$): δ=0.49 (2H), 0.65 (2H), 2.23 (3H), 2.61-2.84 (3H), 3.68 (2H), 3.86 (3H), 6.58 (1H), 7.24 (1H), 7.31 (1H), 7.42 (1H), 7.50 (1H), 7.72-7.81 (2H), 7.97 (1H), 8.09 (1H), 8.27 (1H) ppm.

Intermediate Example 2a

N-Cyclopropyl-4-{6-[2-(3-fluoro-4-methoxyphenyl)-1,3-dithiolan-2-yl]-8-[(3,3,3-trifluoropropyl)amino]imidazo[1,2-b]pyridazin-3-yl}-2-methylbenzamide

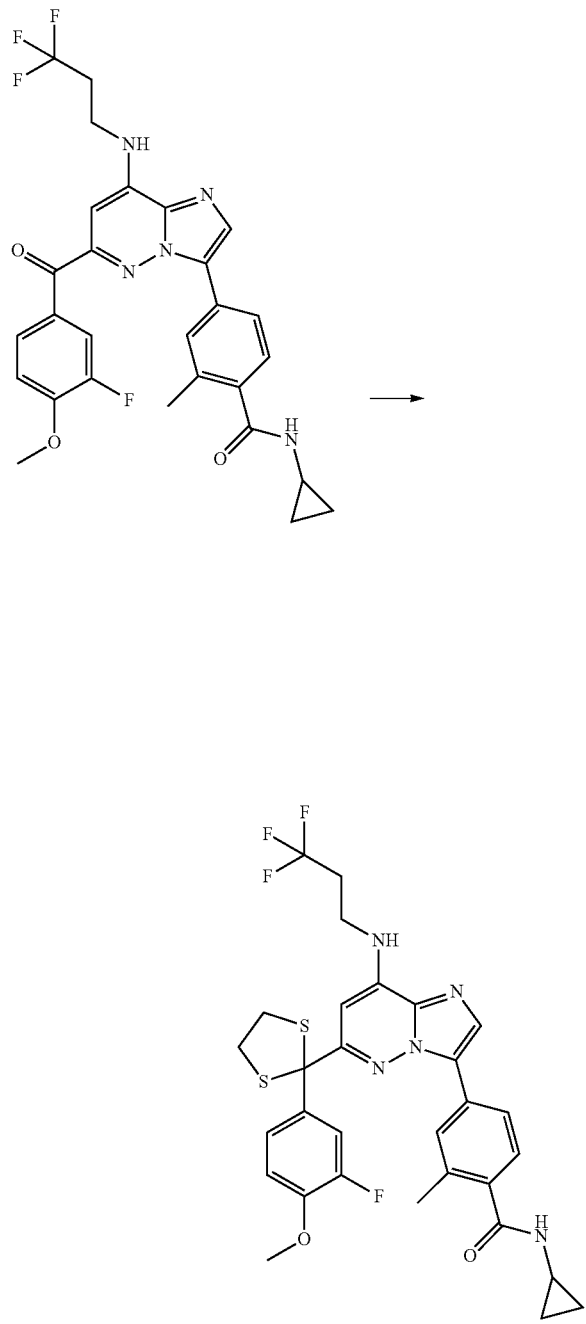

50 mg (90 µmol) N-cyclopropyl-4-{6-(3-fluoro-4-methoxybenzoyl)-8-[(3,3,3-trifluoropropyl)amino]imidazo[1,2-b]pyridazin-3-yl}-2-methylbenzamide which was prepared according to intermediate example 1a were transformed in analogy to comparative example 2b to give after working up and purification 29 mg (51%) of the title compound.

Example 3

(RS)—N-Cyclopropyl-4-{6-[(3-fluoro-2-hydroxyphenyl)(hydroxy)methyl]-8-[(3,3,3-trifluoropropyl)amino]imidazo[1,2-b]pyridazin-3-yl}-2-methylbenzamide

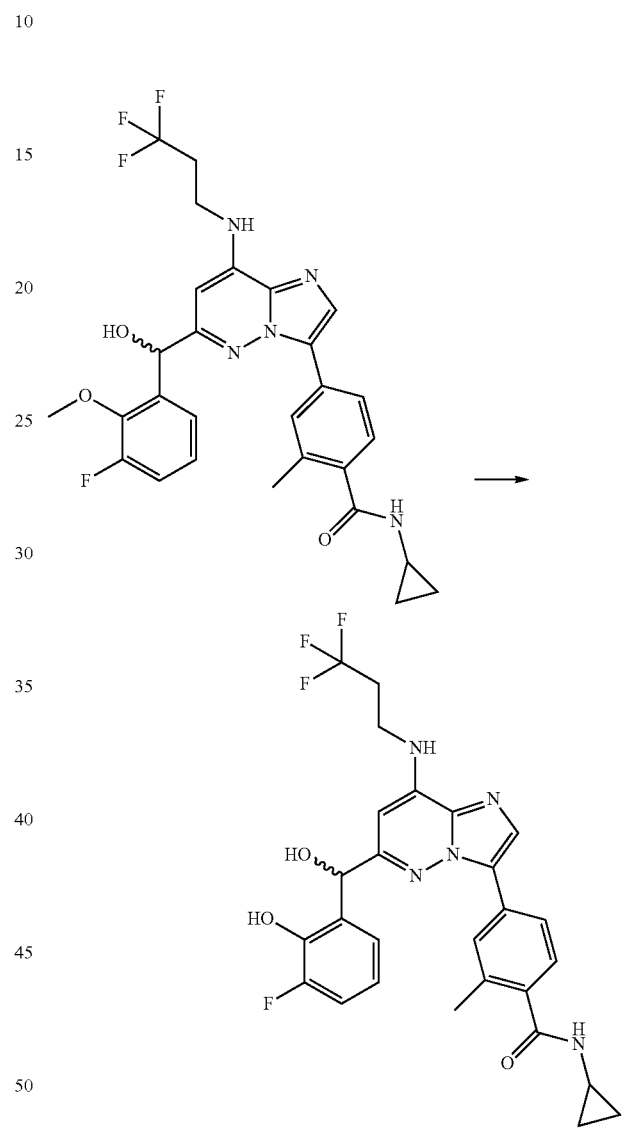

A mixture of 25.0 mg (45 µmol) (RS)—N-cyclopropyl-4-{6-[(3-fluoro-2-methoxyphenyl)(hydroxy)methyl]-8-[(3,3,3-trifluoropropyl)amino]imidazo[1,2-b]pyridazin-3-yl}-2-methylbenzamide which was prepared according to intermediate example 3a, 25.1 mg sodium methanethiolate and 900 µL dimethyl sulfoxide was heated under microwave irradiation for 5 minutes at 130° C. Hydrochloric acid was added and the solvent removed. The residue was purified by chromatography to give 8.2 mg (32%) of the title compound.

$^1$H-NMR (DMSO-d$_6$): δ=0.50 (2H), 0.65 (2H), 2.29 (3H), 2.56-2.72 (2H), 2.79 (1H), 3.57 (2H), 6.00 (1H), 6.33 (1H), 6.33 (1H), 6.79 (1H), 7.03 (1H), 7.24 (1H), 7.27 (1H), 7.44 (1H), 7.86-7.92 (2H), 8.96 (1H), 8.24 (1H) ppm.

Intermediate Example 3a (RS)—N-Cyclopropyl-4-{6-[(3-fluoro-2-methoxy-phenyl)(hydroxy)methyl]-8-[(3,3,3-trifluoropropyl)amino]imidazo[1,2-b]pyridazin-3-yl}-2-methylbenzamide

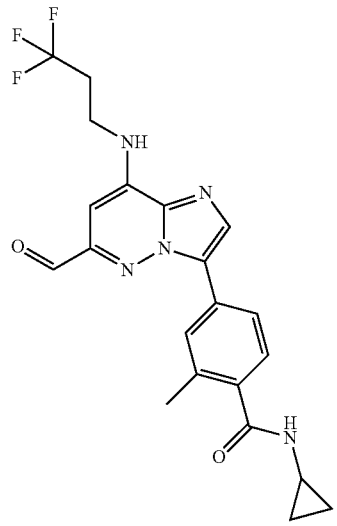

500 mg (1.16 mmol) N-cyclopropyl-4-{6-formyl-8-[(3,3,3-trifluoropropyl)amino]imidazo[1,2-b]pyridazin-3-yl}-2-methylbenzamide which was prepared according to intermediate example 1c were transformed in analogy to intermediate example 1b using bromo(3-fluoro-2-methoxyphenyl)magnesium to give after working up and purification 519 mg (80%) of the title compound.

Example 4

(RS)—N-Cyclopropyl-4-{6-[1-(3-fluoro-2-hydroxy-phenyl)-1-hydroxyethyl]-8-[(3,3,3-trifluoropropyl)amino]imidazo[1,2-b]pyridazin-3-yl}-2-methylbenzamide

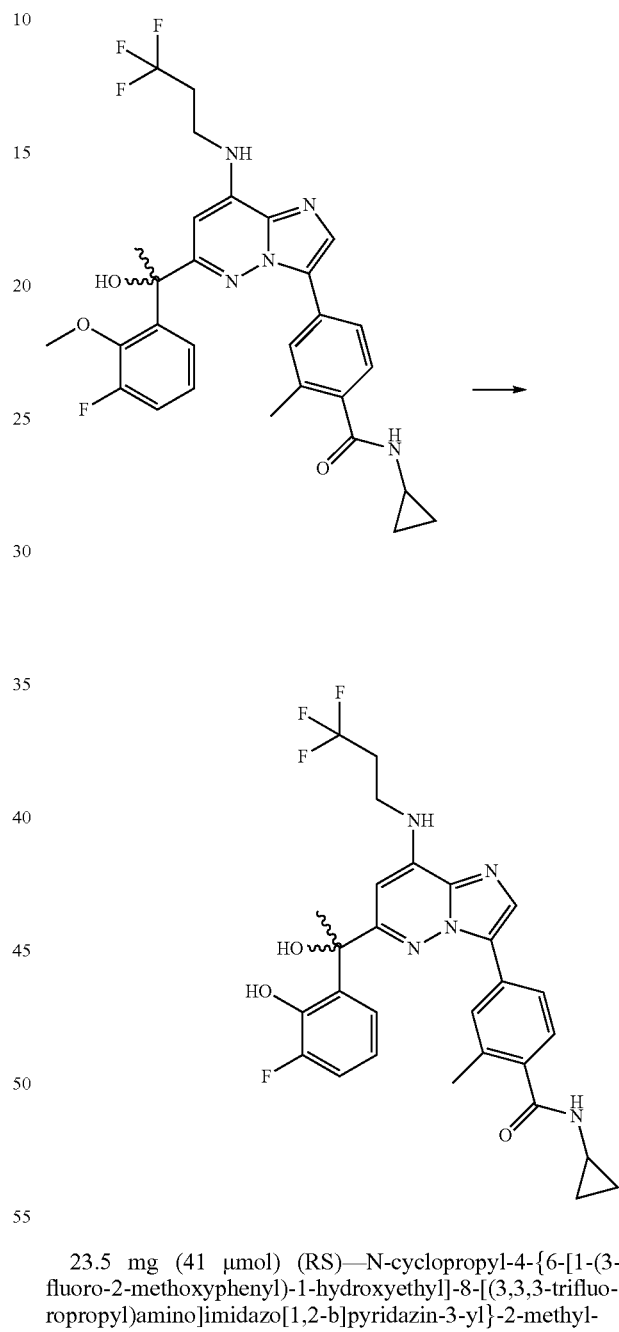

23.5 mg (41 µmol) (RS)—N-cyclopropyl-4-{6-[1-(3-fluoro-2-methoxyphenyl)-1-hydroxyethyl]-8-[(3,3,3-trifluoropropyl)amino]imidazo[1,2-b]pyridazin-3-yl}-2-methylbenzamide which was prepared according to intermediate example 4a were transformed in analogy to example 3 to give after working up and purification 9.5 mg (39%) of the title compound.

$^1$H-NMR (DMSO-d$_6$): δ=0.50 (2H), 0.65 (2H), 1.91 (3H), 2.32 (3H), 2.52-2.65 (2H), 2.80 (1H), 3.49 (2H), 6.22 (1H), 6.69 (1H), 7.00 (1H), 7.18 (1H), 7.28 (1H), 7.35 (1H), 7.93 (1H), 7.96-8.02 (2H), 8.25 (1H), 8.59 (1H) ppm.

Intermediate Example 4a (RS)—N-Cyclopropyl-4-{6-[1-(3-fluoro-2-methoxyphenyl)-1-hydroxyethyl]-8-[(3,3,3-trifluoropropyl)amino]imidazo[1,2-b]pyridazin-3-yl}-2-methylbenzamide

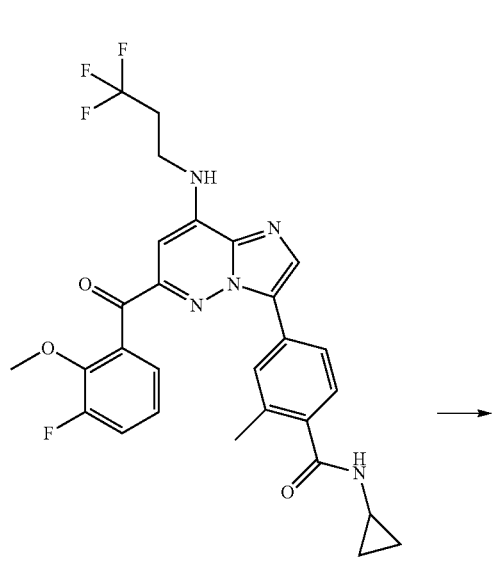

To a solution of 50 mg (90 μmol) N-cyclopropyl-4-{6-(3-fluoro-2-methoxybenzoyl)-8-[(3,3,3-trifluoropropyl)amino]imidazo[1,2-b]pyridazin-3-yl}-2-methylbenzamide which was prepared according to intermediate example 4b in 2.5 mL tetrahydrofuran at −78° C. were added 225 μL methyllithium (2.5M in diethyl ether). The mixture was stirred at −50° C. for 30 minutes, poured into water and extracted with ethyl acetate. The organic layer was washed with saturated aqueous ammonium chloride solution and dried over sodium sulfate. After filtration and removal of the solvent, the residue was purified by chromatography to give 29 mg (56%) of the title compound.

Intermediate Example 4b

N-Cyclopropyl-4-{6-(3-fluoro-2-methoxybenzoyl)-8-[(3,3,3-trifluoropropyl)amino]imidazo[1,2-b]pyridazin-3-yl}-2-methylbenzamide

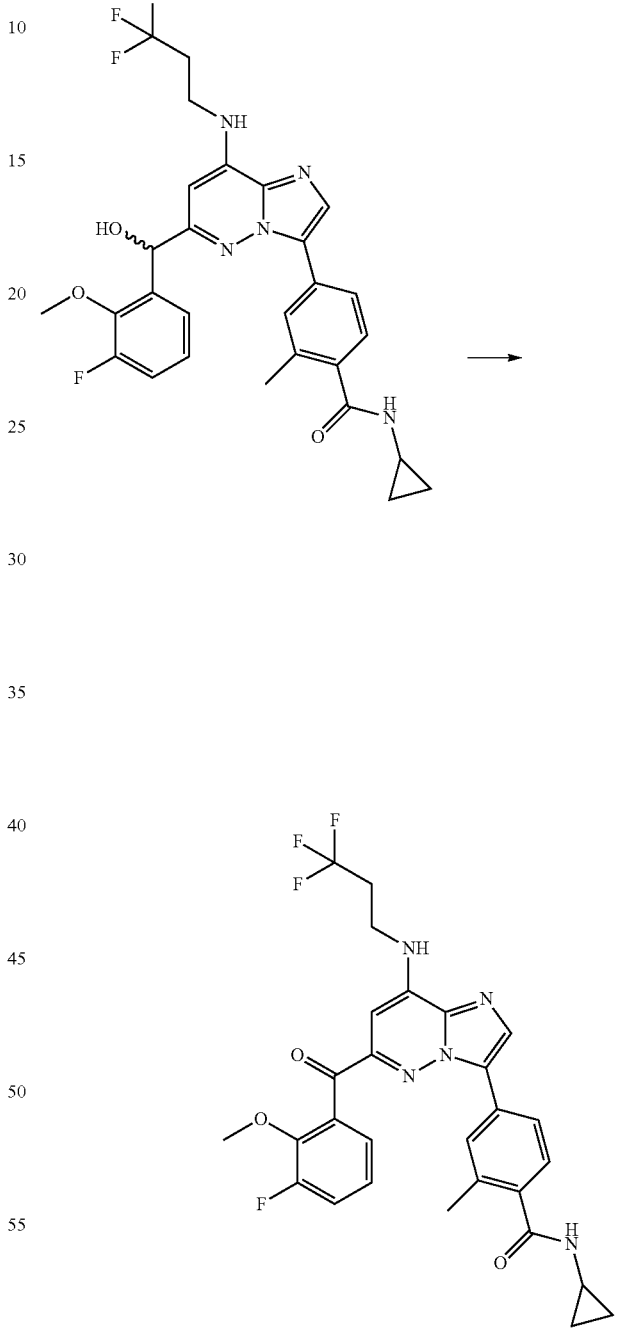

442 mg (793 μmol) (RS)—N-cyclopropyl-4-{6-[(3-fluoro-2-methoxyphenyl)(hydroxy)methyl]-8-[(3,3,3-trifluoropropyl)amino]imidazo[1,2-b]pyridazin-3-yl}-2-methylbenzamide which was prepared according to intermediate example 3a were transformed in analogy to intermediate example 1a to give after working up and purification 317 mg (72%) of the title compound.

Example 5

(RS)—N-Cyclopropyl-4-{6-[fluoro(3-fluorophenyl)methyl]-8-[(3,3,3-trifluoropropyl)amino]imidazo[1,2-b]pyridazin-3-yl}-2-methylbenzamide

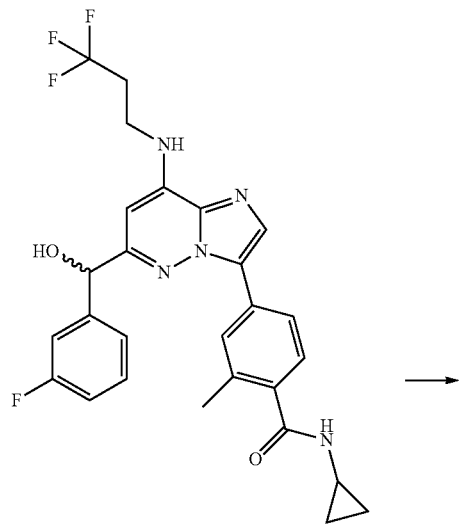

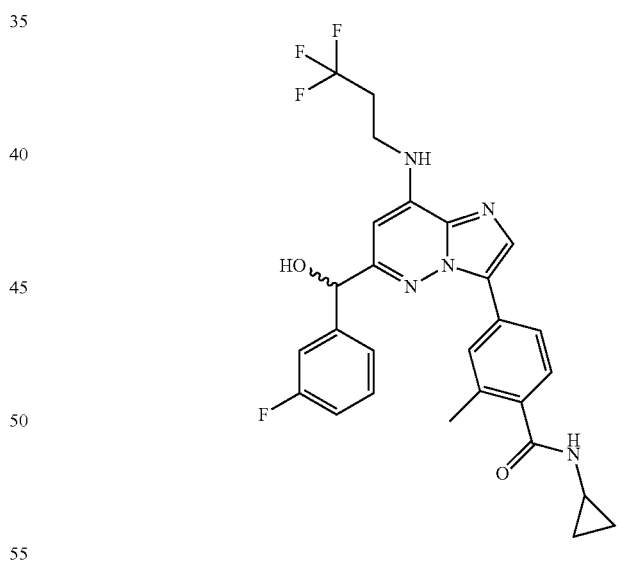

50 mg (95 μmol) (RS)—N-cyclopropyl-4-{6-[(3-fluorophenyl)(hydroxy)methyl]-8-[(3,3,3-trifluoropropyl)amino]imidazo[1,2-b]pyridazin-3-yl}-2-methylbenzamide which was prepared according to intermediate example 5a were transformed in analogy to example 2 to give after working up and purification 4.3 mg (7%) of the title compound.

$^1$H-NMR (DMSO-d$_6$): δ=0.50 (2H), 0.65 (2H), 2.31 (3H), 2.50 (1H), 2.61-2.74 (2H), 2.80 (1H), 3.63 (2H), 6.41 (1H), 6.68 (1H), 7.22 (1H), 7.29 (1H), 7.33-7.39 (1H), 7.46 (1H), 7.75 (1H), 7.87-7.90 (2H), 8.02 (1H), 8.26 (1H) ppm.

Intermediate Example 5a (RS)—N-Cyclopropyl-4-{6-[(3-fluorophenyl)(hydroxy)methyl]-8-[(3,3,3-trifluoropropyl)amino]imidazo[1,2-b]pyridazin-3-yl}-2-methylbenzamide

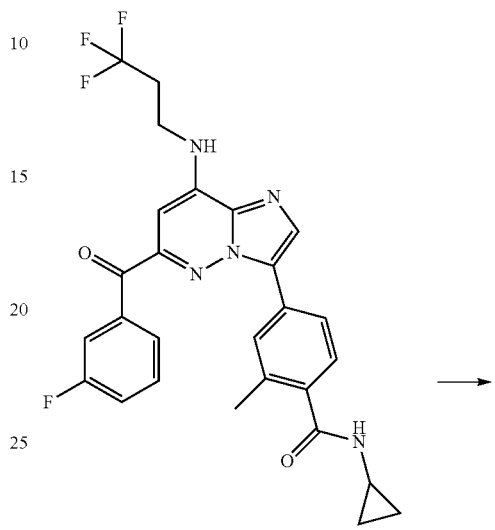

To a solution of 210 mg (400 μmol) N-cyclopropyl-4-{6-(3-fluorobenzoyl)-8-[(3,3,3-trifluoropropyl)amino]imidazo[1,2-b]pyridazin-3-yl}-2-methylbenzamide which was prepared according to comparative example 3b in 5 mL dichloromethane were added at 3° C. 151 mg sodium borohydride and stirring was continued for 1 hour and at 23° C. for 1 hour. Water was added and the organic layer was washed with water and dried over sodium sulfate. After filtration and removal of the solvent, 209 mg (96%) of the title compound were obtained that was used without further purification.

85

Example 6

N-Cyclopropyl-4-{6-[difluoro(3-fluorophenyl)methyl]-8-[(3,3,3-trifluoropropyl)amino]imidazo[1,2-b]pyridazin-3-yl}-2-methylbenzamide

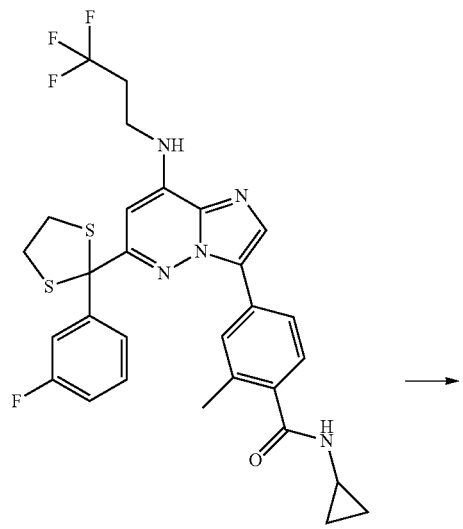

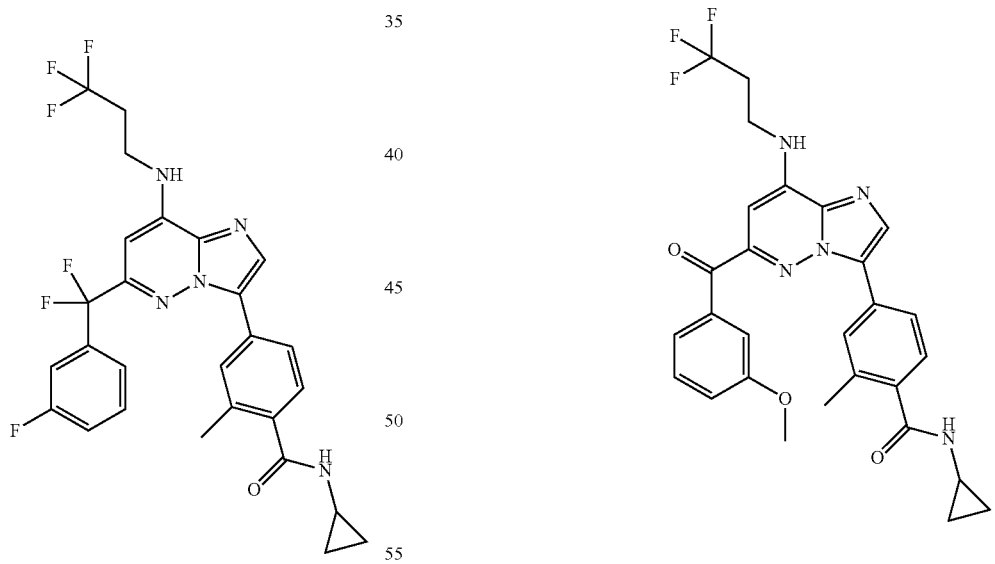

28 mg (46 μmol) N-cyclopropyl-4-{6-[2-(3-fluorophenyl)-1,3-dithiolan-2-yl]-8-[(3,3,3-trifluoropropyl)amino]imidazo[1,2-b]pyridazin-3-yl}-2-methylbenzamide which was prepared according to comparative example 3a were transformed in analogy to example 2 to give after working up and purification 7.9 mg (31%) of the title compound.

$^1$H-NMR (DMSO-$d_6$): δ=0.49 (2H), 0.65 (2H), 2.24 (3H), 2.61-2.84 (3H), 3.70 (2H), 6.61 (1H), 7.23 (1H), 7.41 (1H), 7.46-7.53 (2H), 7.57 (1H), 7.74 (1H), 7.75 (1H), 7.97 (1H), 8.09 (1H), 8.24 (1H) ppm.

86

Example 7

N-Cyclopropyl-4-{6-(3-methoxybenzoyl)-8-[(3,3,3-trifluoropropyl)amino]imidazo[1,2-b]pyridazin-3-yl}-2-methylbenzamide

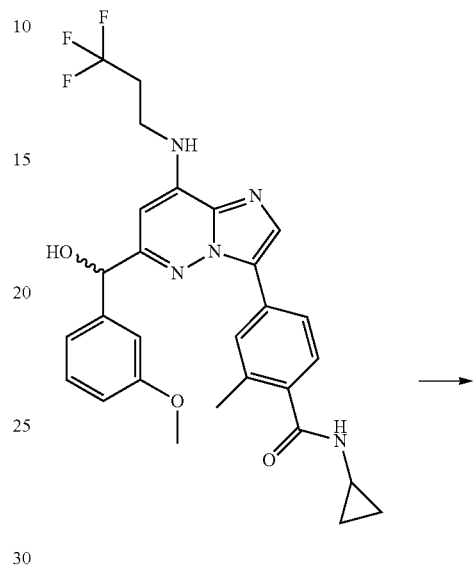

52 mg (96 μmol) (RS)—N-cyclopropyl-4-{6-[hydroxy(3-methoxyphenyl)methyl]-8-[(3,3,3-trifluoropropyl)amino]imidazo[1,2-b]pyridazin-3-yl}-2-methylbenzamide which was prepared according to intermediate example 7a were transformed in analogy to intermediate example 1a to give after working up and purification 34 mg (62%) of the title compound.

$^1$H-NMR (DMSO-$d_6$): δ=0.47 (2H), 0.64 (2H), 2.19 (3H), 2.62-2.82 (3H), 3.69 (2H), 3.76 (3H), 6.71 (1H), 7.23 (1H), 7.27 (1H), 7.48 (1H), 7.54 (1H), 7.61 (1H), 7.84 (1H), 7.89 (1H), 7.96 (1H), 8.15 (1H), 8.22 (1H) ppm.

Intermediate Example 7a (RS)—N-cyclopropyl-4-{6-[hydroxy(3-methoxyphenyl)methyl]-8-[(3,3,3-trifluoropropyl)amino]imidazo[1,2-b]pyridazin-3-yl}-2-methylbenzamide

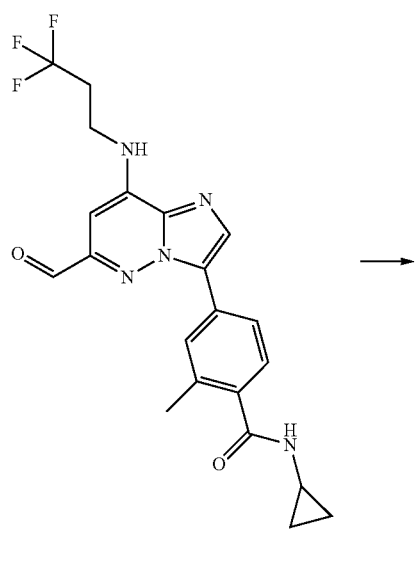

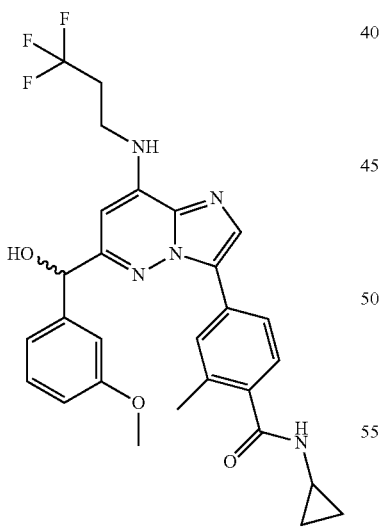

110 mg (255 µmol) N-cyclopropyl-4-{6-formyl-8-[(3,3,3-trifluoropropyl)amino]imidazo[1,2-b]pyridazin-3-yl}-2-methylbenzamide which was prepared according to intermediate example 1c were transformed in analogy to intermediate example 1b using bromo(3-methoxyphenyl)magnesium to give after working up and purification 79 mg (55%) of the title compound.

Example 8

N-Cyclopropyl-4-{6-[1-(3-methoxyphenyl)vinyl]-8-[(3,3,3-trifluoropropyl)amino]imidazo[1,2-b]pyridazin-3-yl}-2-methylbenzamide

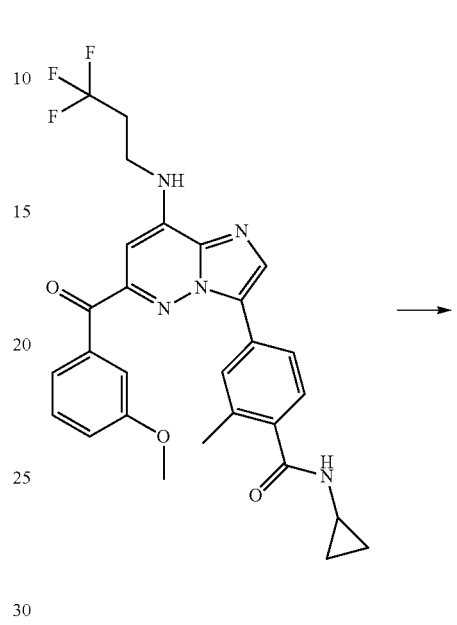

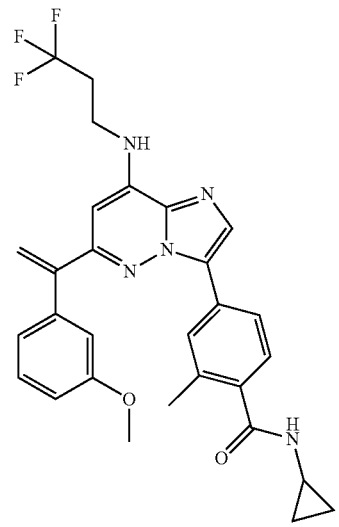

175 mg (326 µmol) N-cyclopropyl-4-{6-(3-methoxybenzoyl)-8-[(3,3,3-trifluoropropyl)amino]imidazo[1,2-b]pyridazin-3-yl}-2-methylbenzamide which was prepared according to example 7 were transformed in analogy to example 1 to give after working up and purification 96.3 mg (55%) of the title compound.

$^1$H-NMR (DMSO-$d_6$): δ=0.48 (2H), 0.64 (2H), 2.18 (3H), 2.60-2.72 (2H), 2.78 (1H), 3.60 (2H), 3.71 (3H), 5.75 (1H), 5.98 (1H), 6.34 (1H), 6.92-6.99 (3H), 7.21 (1H), 7.29 (1H), 7.53 (1H), 7.84 (1H), 7.89 (1H), 8.01 (1H), 8.21 (1H) ppm.

Example 9

N-Cyclopropyl-4-{6-(4-methoxybenzoyl)-8-[(3,3,3-trifluoropropyl)amino]imidazo[1,2-b]pyridazin-3-yl}-2-methylbenzamide

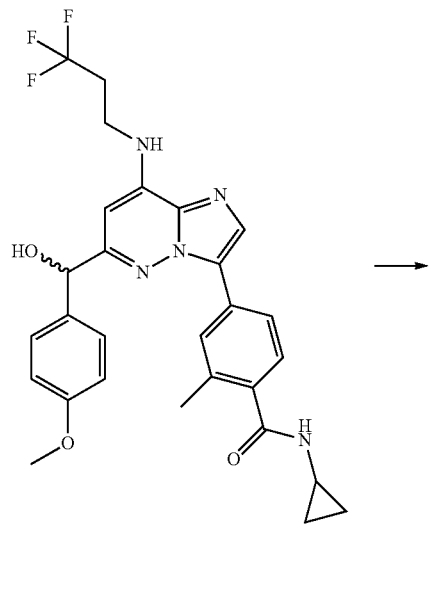

→

Intermediate Example 9a (RS)—N-Cyclopropyl-4-{6-[hydroxy(4-methoxyphenyl)methyl]-8-[(3,3,3-trifluoropropyl)amino]imidazo[1,2-b]pyridazin-3-yl}-2-methylbenzamide

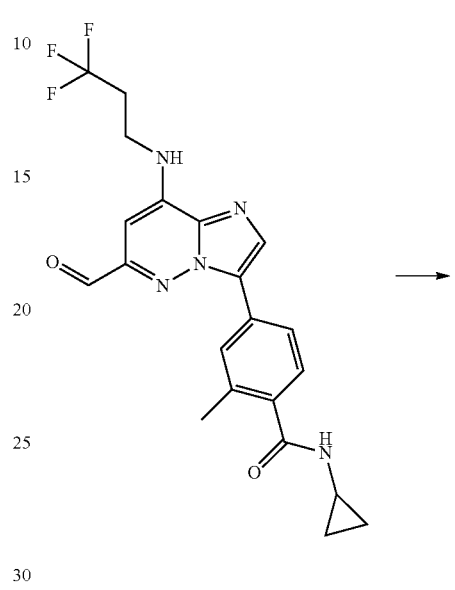

→

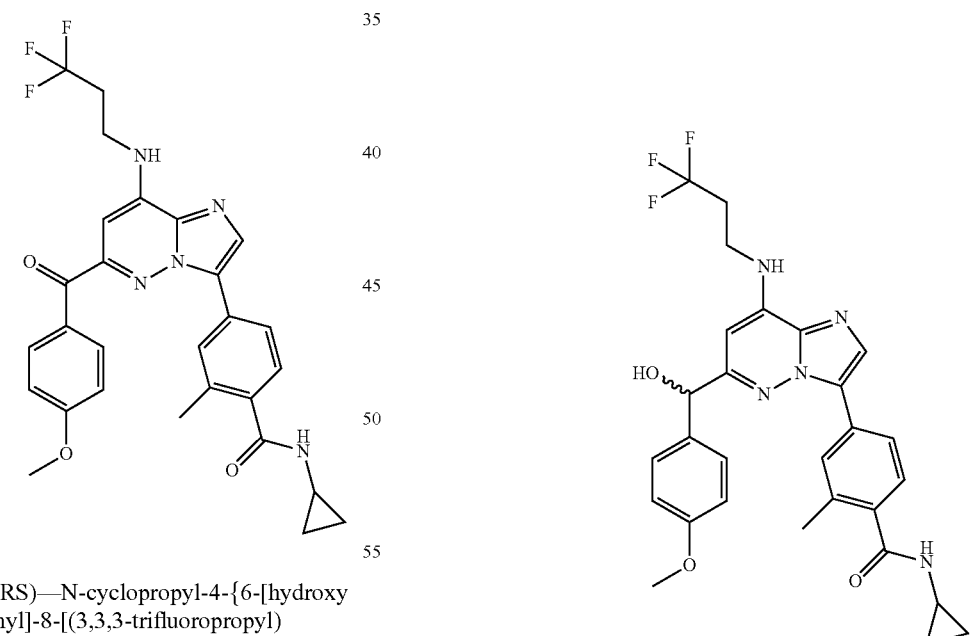

400 mg (741 µmol) (RS)—N-cyclopropyl-4-{6-[hydroxy(4-methoxyphenyl)methyl]-8-[(3,3,3-trifluoropropyl)amino]imidazo[1,2-b]pyridazin-3-yl}-2-methylbenzamide which was prepared according to intermediate example 9a were transformed in analogy to intermediate example 1a to give after working up and purification 264 mg (66%) of the title compound.

$^1$H-NMR (DMSO-d$_6$): δ=0.51 (2H), 0.66 (2H), 2.34 (3H), 2.56-2.72 (2H), 2.81 (1H), 3.56 (2H), 3.68 (3H), 6.31 (1H), 6.86 (2H), 7.33 (1H), 7.38 (2H), 7.49 (1H), 7.93-8.02 (3H), 8.29 (1H) ppm.

500 mg (1.16 mmol) N-cyclopropyl-4-{6-formyl-8-[(3,3,3-trifluoropropyl)amino]imidazo[1,2-b]pyridazin-3-yl}-2-methylbenzamide which was prepared according to intermediate example 1c were transformed in analogy to intermediate example 1b using bromo(4-methoxyphenyl)magnesium to give after working up and purification 501 mg (72%) of the title compound.

Example 10

N-Cyclopropyl-4-{6-[1-(4-methoxyphenyl)vinyl]-8-[(3,3,3-trifluoropropyl)amino]imidazo[1,2-b]pyridazin-3-yl}-2-methylbenzamide

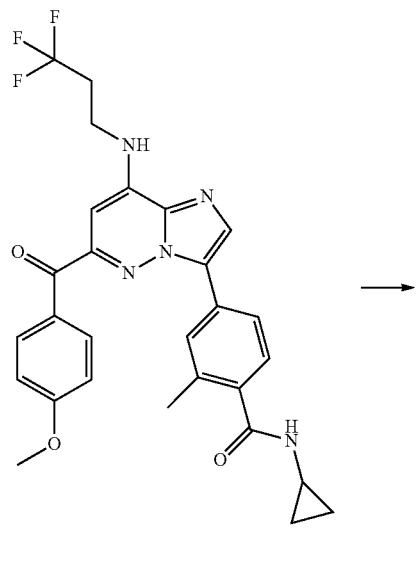

73 mg (136 µmol) N-cyclopropyl-4-{6-(4-methoxybenzoyl)-8-[(3,3,3-trifluoropropyl)amino]imidazo[1,2-b]pyridazin-3-yl}-2-methylbenzamide which was prepared according to example 9 were transformed in analogy to example 1 to give after working up and purification 36.1 mg (45%) of the title compound.

$^1$H-NMR (DMSO-d$_6$): δ=0.47 (2H), 0.63 (2H), 2.17 (3H), 2.60-2.72 (2H), 2.78 (1H), 3.60 (2H), 3.76 (3H), 5.66 (1H), 5.85 (1H), 6.32 (1H), 6.93 (2H), 7.22 (1H), 7.35 (2H), 7.52 (1H), 7.84 (1H), 7.89 (1H), 8.00 (1H), 8.21 (1H) ppm.

Example 11

(RS)—N-Cyclopropyl-4-{6-[(2,5-difluorophenyl)(hydroxy)methyl]-8-[(3,3,3-trifluoropropyl)amino]imidazo[1,2-b]pyridazin-3-yl}-2-methylbenzamide

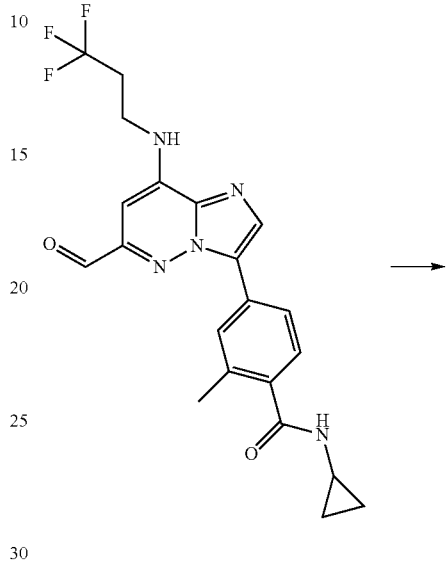

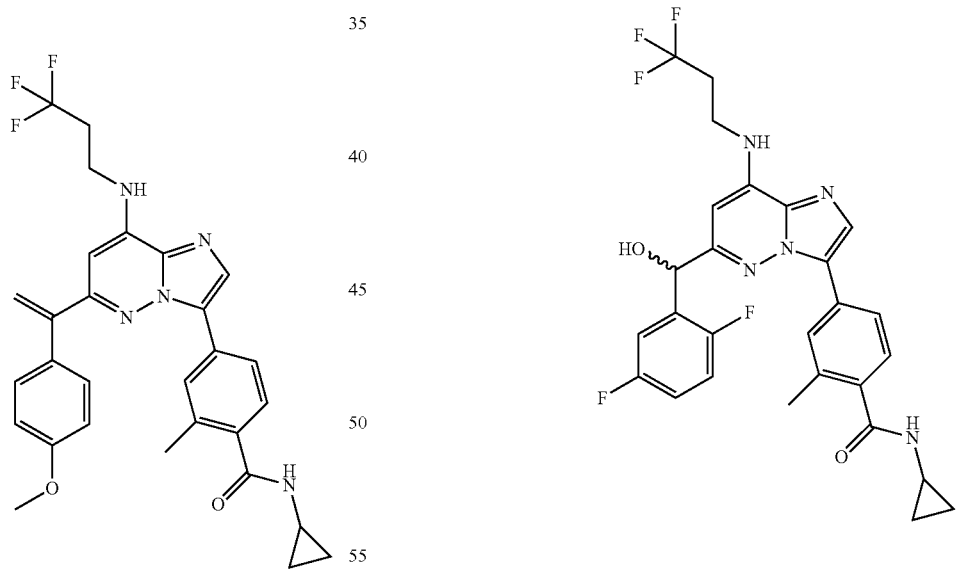

400 mg (927 µmol) N-cyclopropyl-4-{6-formyl-8-[(3,3,3-trifluoropropyl)amino]imidazo[1,2-b]pyridazin-3-yl}-2-methylbenzamide which was prepared according to intermediate example 1c were transformed in analogy to intermediate example 1b using bromo(2,5-difluorophenyl)magnesium to give after working up and purification 326 mg (64%) of the title compound.

$^1$H-NMR (DMSO-d$_6$): δ=0.49 (2H), 0.65 (2H), 2.27 (3H), 2.58-2.74 (2H), 2.79 (1H), 3.60 (2H), 5.94 (1H), 6.41 (1H), 6.54 (1H), 7.12-7.27 (3H), 7.44 (1H), 7.57 (1H), 7.82 (1H), 7.88 (1H), 7.99 (1H), 8.26 (1H) ppm.

Example 12

N-Cyclopropyl-4-{6-(2,5-difluorobenzoyl)-8-[(3,3,3-trifluoropropyl)amino]imidazo[1,2-b]pyridazin-3-yl}-2-methylbenzamide

Example 13

N-Cyclopropyl-4-{6-(3-fluoro-4-methoxybenzoyl)-8-[(3,3,3-trifluoropropyl)amino]imidazo[1,2-b]pyridazin-3-yl}-2-methylbenzamide

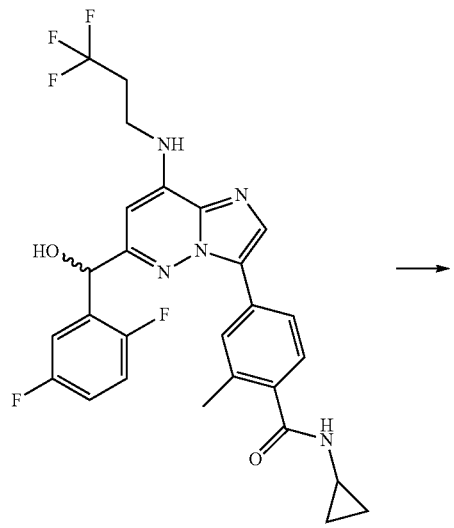
→

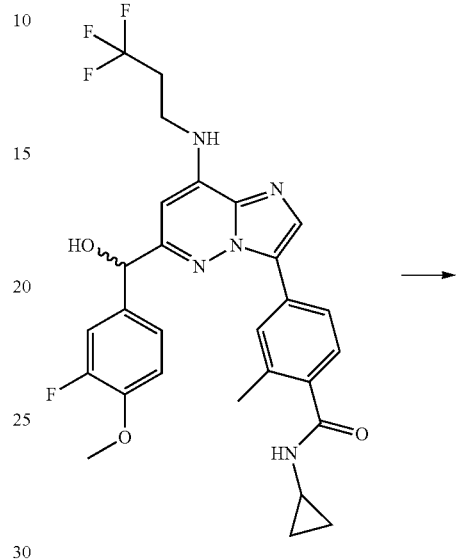
→

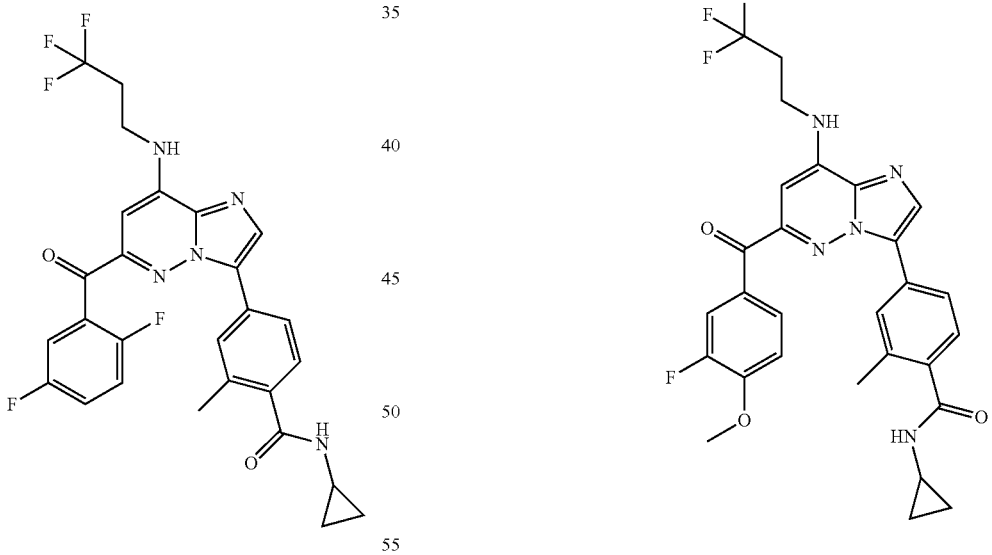

300 mg (550 µmol) (RS)—N-cyclopropyl-4-{6-[(2,5-difluorophenyl)(hydroxy)methyl]-8-[(3,3,3-trifluoropropyl)amino]imidazo[1,2-b]pyridazin-3-yl}-2-methylbenzamide which was prepared according to example 11 were transformed in analogy to intermediate example 1a to give after working up and purification 82 mg (27%) of the title compound.

$^1$H-NMR (DMSO-$d_6$): δ=0.48 (2H), 0.64 (2H), 2.14 (3H), 2.63-2.82 (3H), 3.71 (2H), 6.79 (1H), 7.18 (1H), 7.46 (1H), 7.55 (1H), 7.65 (1H), 7.73 (1H), 7.81 (1H), 7.99 (1H), 8.18 (1H), 8.23 (1H) ppm.

262 mg (470 µmol) N-cyclopropyl-4-{6-[(3-fluoro-4-methoxyphenyl)(hydroxy)methyl]-8-[(3,3,3-trifluoropropyl)amino]imidazo[1,2-b]pyridazin-3-yl}-2-methylbenzamide which was prepared according to intermediate example 1b were transformed in analogy to intermediate example 1a to give after working up and purification 210 mg (80%) of the title compound.

$^1$H-NMR (DMSO-$d_6$): δ=0.48 (2H), 0.64 (2H), 2.24 (3H), 2.64-2.75 (2H), 2.78 (1H), 3.68 (2H), 3.94 (3H), 6.67 (1H), 7.28 (1H), 7.34 (1H), 7.85 (1H), 7.89 (1H), 7.93-7.99 (3H), 8.13 (1H), 8.24 (1H) ppm.

Example 14

N-Cyclopropyl-4-{6-(2,3-difluorobenzoyl)-8-[(3,3,3-trifluoropropyl)amino]imidazo[1,2-b]pyridazin-3-yl}-2-methylbenzamide

Example 14a

N-Cyclopropyl-4-{6-[(2,3-difluorophenyl)(hydroxy)methyl]-8-[(3,3,3-trifluoropropyl)amino]imidazo[1,2-b]pyridazin-3-yl}-2-methylbenzamide

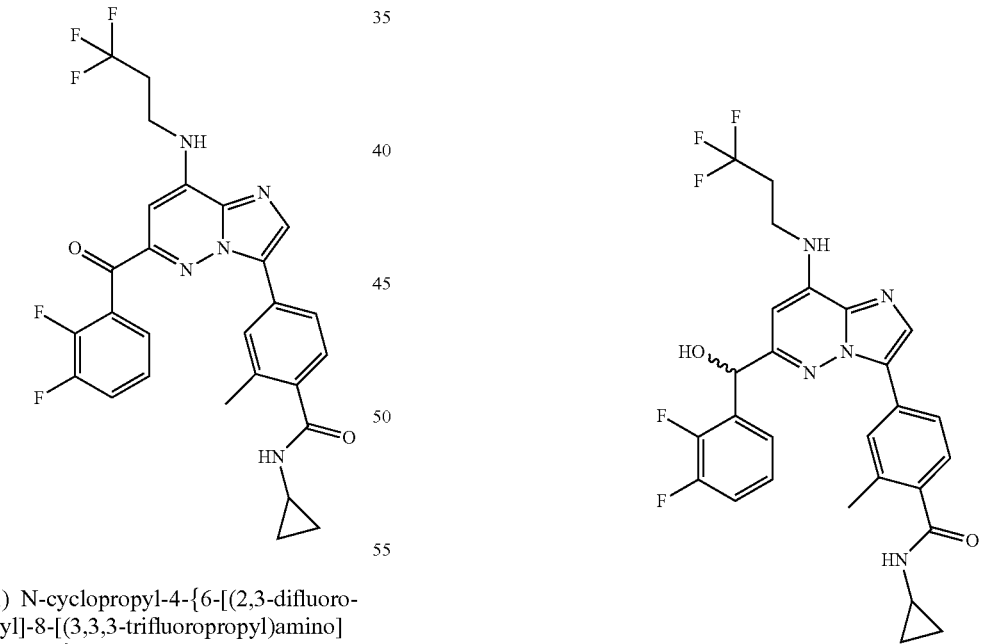

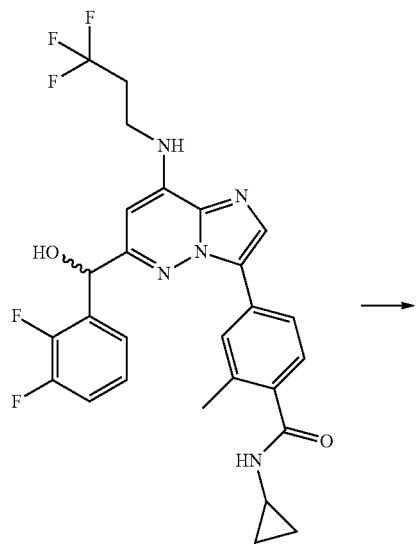

296 mg (543 μmol) N-cyclopropyl-4-{6-[(2,3-difluorophenyl)(hydroxy)methyl]-8-[(3,3,3-trifluoropropyl)amino]imidazo[1,2-b]pyridazin-3-yl}-2-methylbenzamide which was prepared according to intermediate example 14a were transformed in analogy to intermediate example 1a to give after working up and purification 165 mg (56%) of the title compound.

$^1$H-NMR (DMSO-d$_6$): δ=0.47 (2H), 0.64 (2H), 2.13 (3H), 2.63-2.82 (3H), 3.71 (2H), 6.80 (1H), 7.17 (1H), 7.40 (1H), 7.55 (1H), 7.68-7.84 (3H), 8.04 (1H), 8.19 (1H), 8.26 (1H) ppm.

400 mg (927 μmol) N-cyclopropyl-4-{6-formyl-8-[(3,3,3-trifluoropropyl)amino]imidazo[1,2-b]pyridazin-3-yl}-2-methylbenzamide which was prepared according to intermediate example 1c were transformed in analogy to intermediate example 1b using bromo(2,3-difluorophenyl)magnesium to give after working up and purification 326 mg (64%) of the title compound.

Example 15

N-Cyclopropyl-4-{6-[1-(2,3-difluorophenyl)vinyl]-8-[(3,3,3-trifluoropropyl)amino]imidazo[1,2-b]pyridazin-3-yl}-2-methylbenzamide

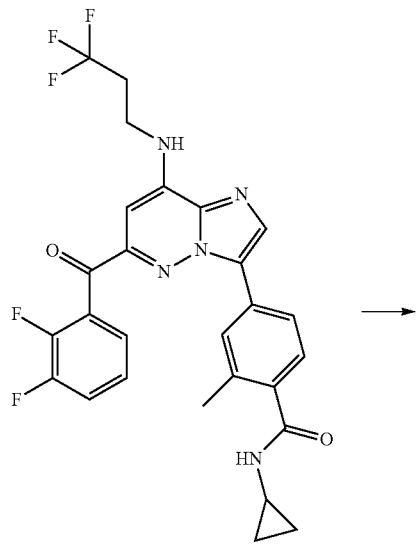

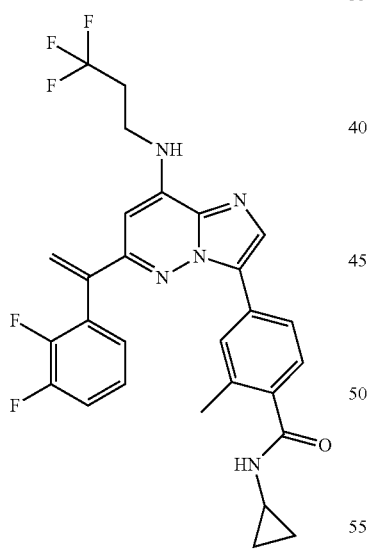

75 mg (138 μmol) N-Cyclopropyl-4-{6-(2,3-difluorobenzoyl)-8-[(3,3,3-trifluoropropyl)amino]imidazo[1,2-b]pyridazin-3-yl}-2-methylbenzamide which was prepared according to example 14 were transformed in analogy to example 1 to give after working up and purification 67.2 mg (83%) of the title compound.

$^1$H-NMR (DMSO-$d_6$): δ=0.50 (2H), 0.66 (2H), 2.14 (3H), 2.68-2.83 (3H), 3.69 (2H), 5.81 (1H), 6.47 (1H), 6.65 (1H), 7.14 (1H), 7.22-7.32 (2H), 7.51 (1H), 7.58 (1H), 7.69 (1H), 7.75 (1H), 8.03 (1H), 8.24 (1H) ppm.

Example 16

N-Cyclopropyl-4-{6-[difluoro(4-methoxyphenyl)methyl]-8-[(3,3,3-trifluoropropyl)amino]imidazo[1,2-b]pyridazin-3-yl}-2-methylbenzamide

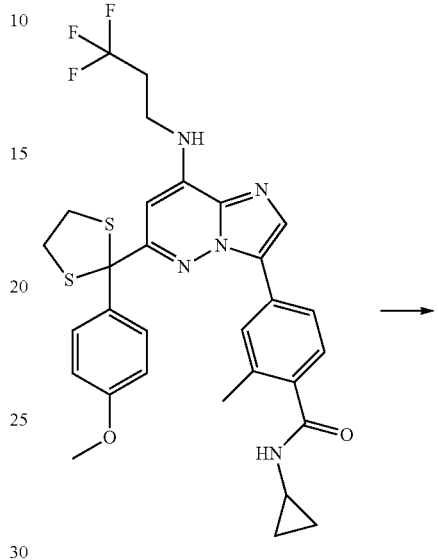

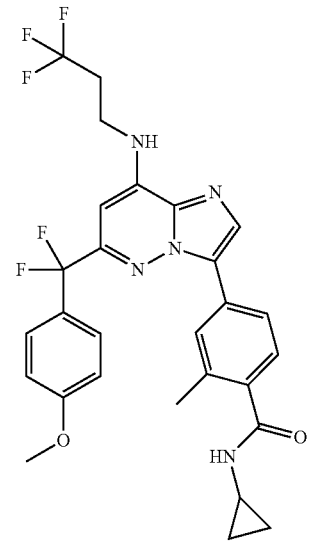

30 mg (49 μmol) N-cyclopropyl-4-{6-[2-(4-methoxyphenyl)-1,3-dithiolan-2-yl]-8-[(3,3,3-trifluoropropyl)amino]imidazo[1,2-b]pyridazin-3-yl}-2-methylbenzamide which was prepared according to comparative example 5a were transformed in analogy to example 2 to give after working up and purification 6.0 mg (21%) of the title compound.

$^1$H-NMR (DMSO-$d_6$): δ=0.49 (2H), 0.65 (2H), 2.23 (3H), 2.61-2.84 (3H), 3.67 (2H), 3.77 (3H), 6.55 (1H), 7.04 (2H), 7.24 (1H), 7.55 (2H), 7.78 (2H), 7.94 (1H), 8.09 (1H), 8.26 (1H) ppm.

Example 17

N-Cyclopropyl-4-{6-[1-(2,3-difluorophenyl)cyclopropyl]-8-[(3,3,3-trifluoropropyl)amino]imidazo[1,2-b]pyridazin-3-yl}-2-methylbenzamide

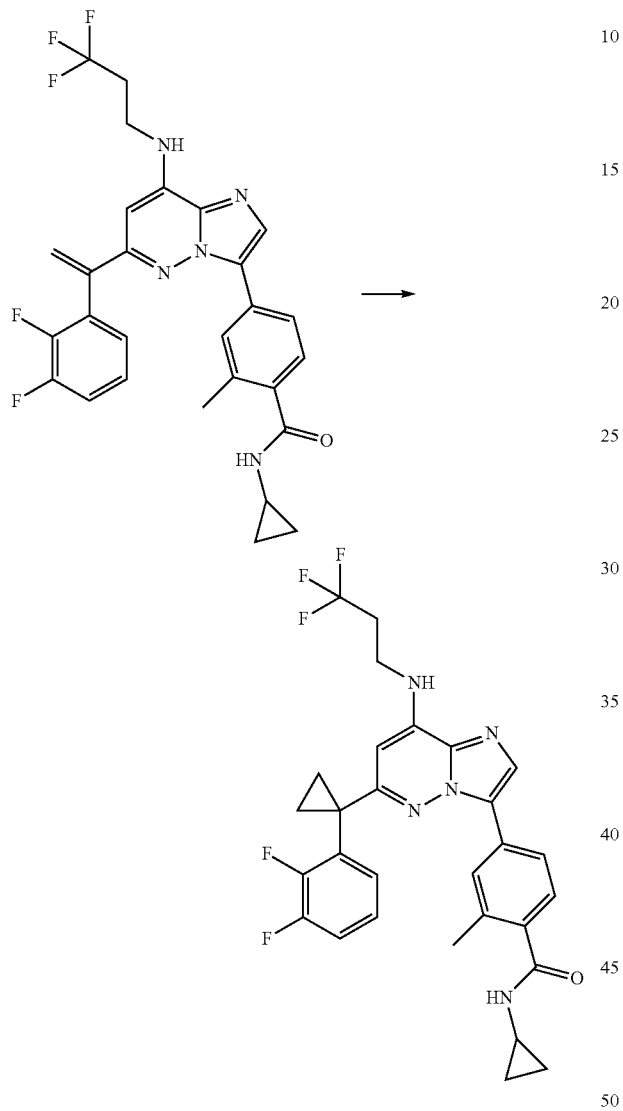

A mixture comprising 68.3 mg [iodo(dimethyl)oxidolambda$^6$-sulfanyl]methane, 12.3 mg sodium hidride (60%) and 0.82 mL dimethyl sulfoxide was stirred at 60° C. for 1.5 hours. A solution of 21 mg (39 μmol) N-cyclopropyl-4-{6-[1-(2,3-difluorophenyl)vinyl]-8-[(3,3,3-trifluoropropyl)amino]imidazo[1,2-b]pyridazin-3-yl}-2-methylbenzamide which was prepared according to example 15 in 0.43 mL dimethyl sulfoxide was added and stirring continued at 130° C. under microwave irradiation for 1.5 hours. Water was added and the mixture extracted with ethyl acetate. The organic layer was washed with brine and dried over sodium sulfate. After filtration and removal of the solvent the residue was purified by chromatography to give 9.8 mg (41%) of the title compound.

$^1$H-NMR (DMSO-d$_6$): δ=0.49 (2H), 0.65 (2H), 1.36 (2H), 1.65 (2H), 2.24 (3H), 2.50-2.67 (2H), 2.80 (1H), 3.52 (2H), 5.73 (1H), 7.16 (1H), 7.22 (1H), 7.30 (1H), 7.34-7.49 (2H), 7.74 (1H), 7.79 (1H), 7.96 (1H), 8.26 (1H) ppm.

Example 18

N-Cyclopropyl-4-{6-[(2,3-difluorophenyl)(difluoro)methyl]-8-[(3,3,3-trifluoropropyl)amino]imidazo[1,2-b]pyridazin-3-yl}-2-methylbenzamide

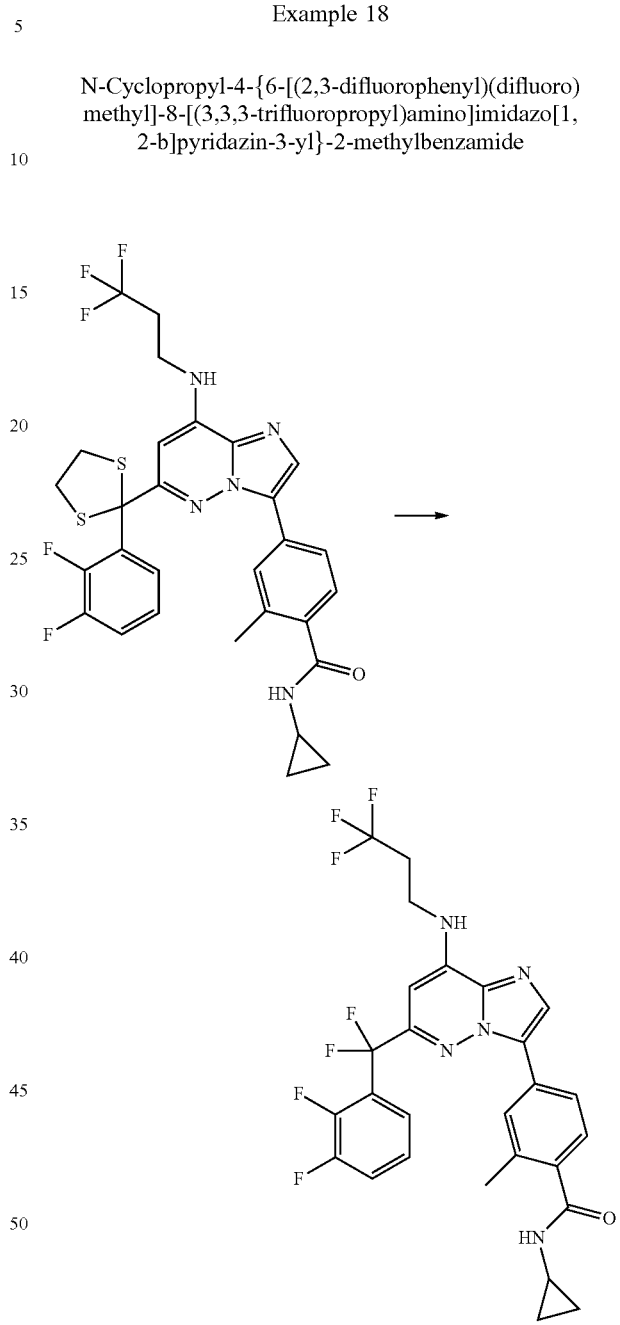

21 mg (34 μmol) N-cyclopropyl-4-{6-[2-(2,3-difluorophenyl)-1,3-dithiolan-2-yl]-8-[(3,3,3-trifluoropropyl)amino]imidazo[1,2-b]pyridazin-3-yl}-2-methylbenzamide which was prepared according to intermediate example 18a were transformed in analogy to example 2 to give after working up and purification 7.8 mg (41%) of the title compound.

$^1$H-NMR (DMSO-d$_6$): δ=0.48 (2H), 0.64 (2H), 2.15 (3H), 2.62-2.82 (3H), 3.71 (2H), 6.66 (1H), 7.14 (1H), 7.43 (1H), 7.56 (1H), 7.61 (1H), 7.65 (1H), 7.75 (1H), 8.07 (1H), 8.11 (1H), 8.26 (1H) ppm.

Example 18a

N-Cyclopropyl-4-{6-[2-(2,3-difluorophenyl)-1,3-dithiolan-2-yl]-8-[(3,3,3-trifluoropropyl)amino]imidazo[1,2-b]pyridazin-3-yl}-2-methylbenzamide

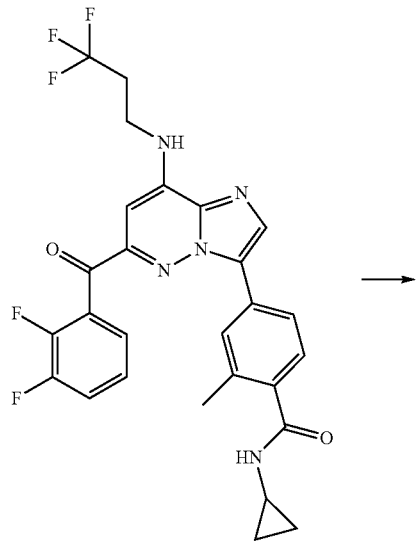

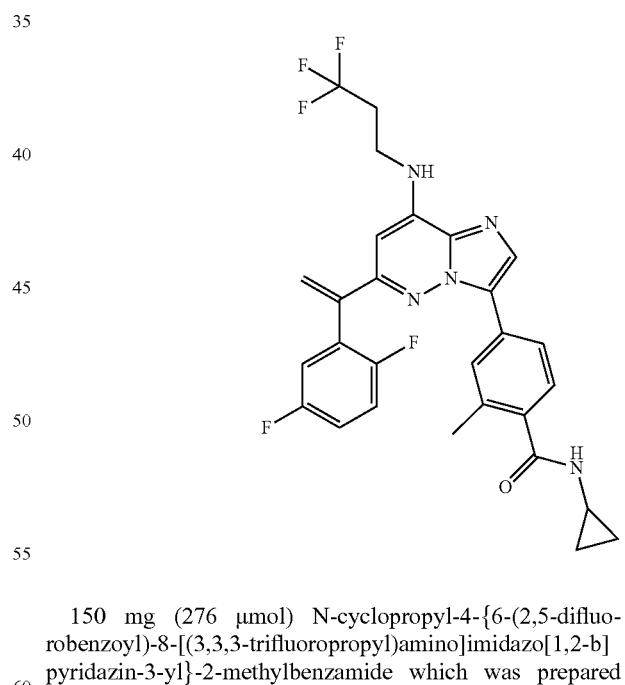

50 mg (92 µmol) N-cyclopropyl-4-{6-(2,3-difluorobenzoyl)-8-[(3,3,3-trifluoropropyl)amino]imidazo[1,2-b]pyridazin-3-yl}-2-methylbenzamide which was prepared according to example 14 were transformed in analogy to comparative example 2b to give after working up and purification 23.6 mg (41%) of the title compound.

Example 19

N-Cyclopropyl-4-{6-[1-(2,5-difluorophenyl)vinyl]-8-[(3,3,3-trifluoropropyl)amino]imidazo[1,2-b]pyridazin-3-yl}-2-methylbenzamide

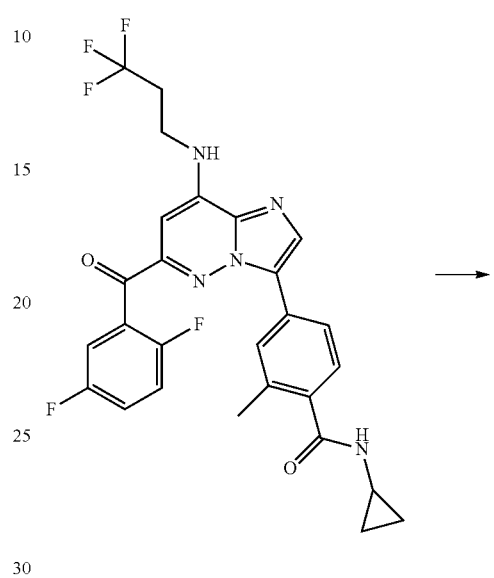

150 mg (276 µmol) N-cyclopropyl-4-{6-(2,5-difluorobenzoyl)-8-[(3,3,3-trifluoropropyl)amino]imidazo[1,2-b]pyridazin-3-yl}-2-methylbenzamide which was prepared according to example 12 were transformed in analogy to example 1 to give after working up and purification 96.2 mg (61%) of the title compound.

$^1$H-NMR (DMSO-$d_6$): δ=0.47 (2H), 0.64 (2H), 2.12 (3H), 2.62-2.81 (3H), 3.66 (2H), 5.78 (1H), 6.42 (1H), 6.61 (1H), 7.12 (1H), 7.23-7.35 (3H), 7.56 (1H), 7.67 (1H), 7.75 (1H), 8.01 (1H), 8.23 (1H) ppm.

103
Example 20

N-Cyclopropyl-4-{6-[1-(2,5-difluorophenyl)cyclopropyl]-8-[(3,3,3-trifluoropropyl)amino]imidazo[1,2-b]pyridazin-3-yl}-2-methylbenzamide

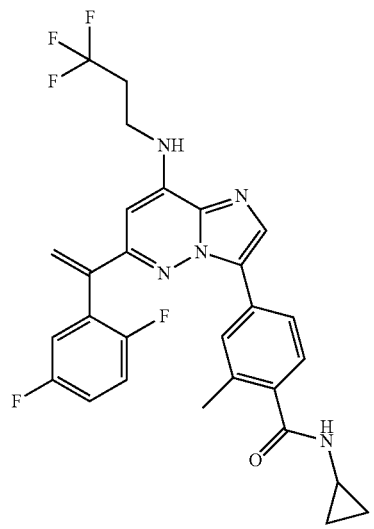

30 mg (55 μmol) N-cyclopropyl-4-{6-[1-(2,5-difluorophenyl)vinyl]-8-[(3,3,3-trifluoropropyl)amino]imidazo[1,2-b]pyridazin-3-yl}-2-methylbenzamide which was prepared according to example 19 were transformed in analogy to example 17 to give after working up and purification 9.9 mg (31%) of the title compound.

$^1$H-NMR (DMSO-$d_6$): δ=0.50 (2H), 0.65 (2H), 1.36 (2H), 1.63 (2H), 2.26 (3H), 2.52-2.64 (2H), 2.80 (1H), 3.52 (2H), 5.75 (1H), 7.16-7.26 (3H), 7.35 (1H), 7.40 (1H) 7.75 (1H), 7.81 (1H), 7.95 (1H), 8.23 (1H) ppm.

104
Example 21

N-Cyclopropyl-4-{6-[(2,5-difluorophenyl)(difluoro)methyl]-8-[(3,3,3-trifluoropropyl)amino]imidazo[1,2-b]pyridazin-3-yl}-2-methylbenzamide

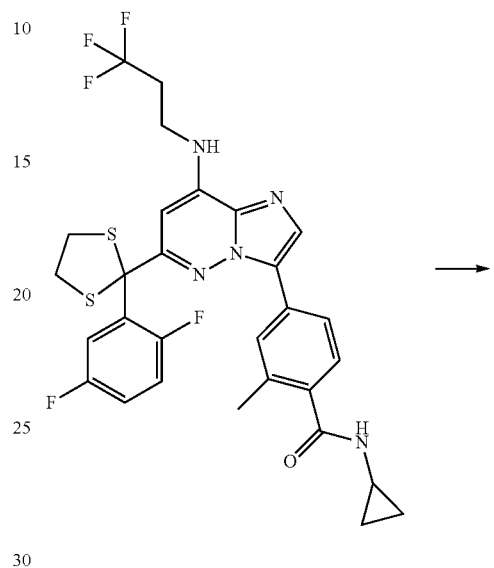

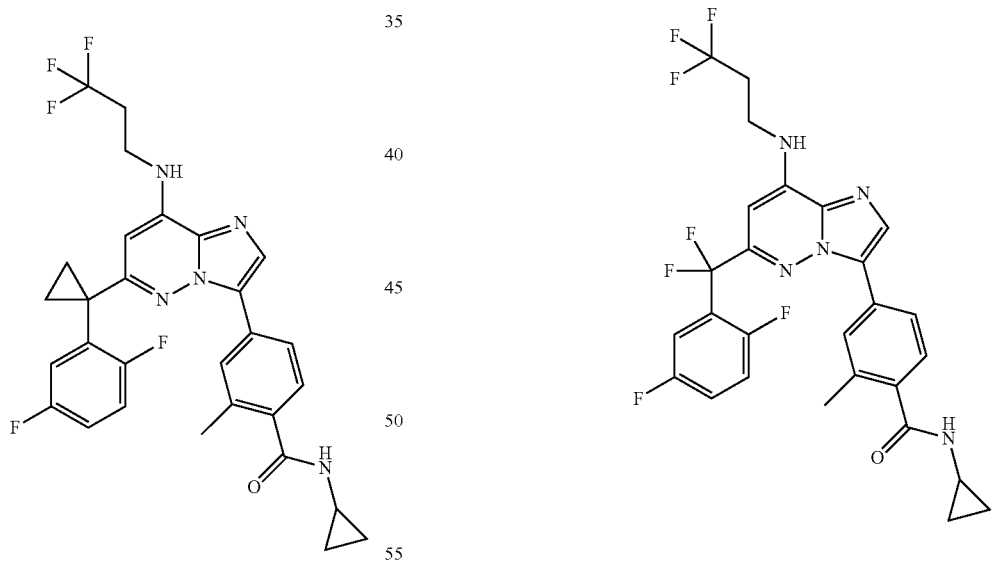

48 mg (77 μmol) N-cyclopropyl-4-{6-[2-(2,5-difluorophenyl)-1,3-dithiolan-2-yl]-8-[(3,3,3-trifluoropropyl)amino]imidazo[1,2-b]pyridazin-3-yl}-2-methylbenzamide which was prepared according to intermediate example 21a were transformed in analogy to comparative example 2b to give after working up and purification 17.3 mg (38%) of the title compound.

$^1$H-NMR (DMSO-$d_6$): δ=0.48 (2H), 0.65 (2H), 2.16 (3H), 2.64-2.82 (3H), 3.71 (2H), 6.65 (1H), 7.16 (1H), 7.46 (1H), 7.56 (1H), 7.60-7.65 (2H), 7.67 (1H), 8.03 (1H), 8.11 (1H), 8.23 (1H) ppm.

Example 21a

N-Cyclopropyl-4-{6-[2-(2,5-difluorophenyl)-1,3-dithiolan-2-yl]-8-[(3,3,3-trifluoropropyl)amino]imidazo[1,2-b]pyridazin-3-yl}-2-methylbenzamide

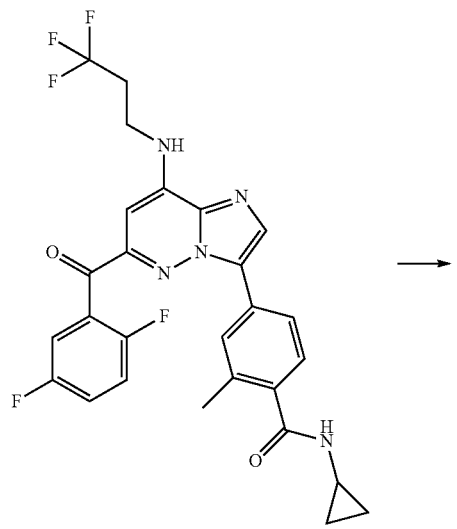

100 mg (184 μmol) N-cyclopropyl-4-{6-(2,5-difluorobenzoyl)-8-[(3,3,3-trifluoropropyl)amino]imidazo[1,2-b]pyridazin-3-yl}-2-methylbenzamide which was prepared according to example 12 were transformed in analogy to comparative example 2b to give after working up and purification 54 mg (47%) of the title compound.

Example 22

N-cyclopropyl-4-{6-[1-(5-fluoro-2-hydroxyphenyl)ethenyl]-8-[(3,3,3-trifluoropropyl)amino]imidazo[1,2-b]pyridazin-3-yl}-2-methylbenzamide

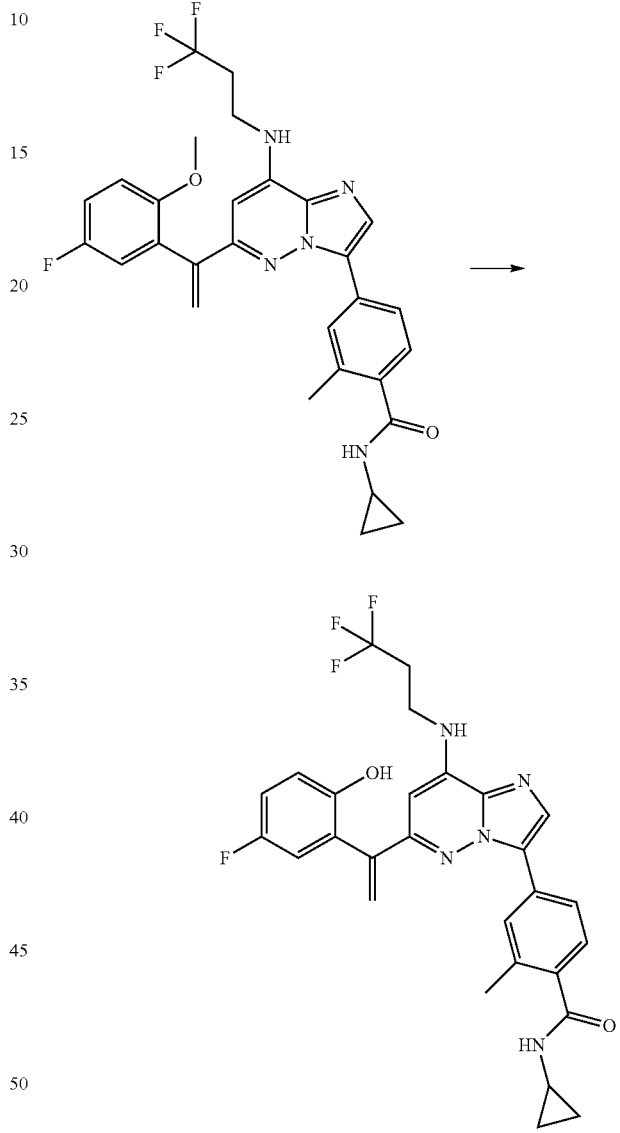

A mixture of 27.0 mg (49 μmol) N-cyclopropyl-4-{6-[1-(5-fluoro-2-methoxyphenyl)ethenyl]-8-[(3,3,3-trifluoropropyl)amino]imidazo[1,2-b]pyridazin-3-yl}-2-methylbenzamide which was prepared according to intermediate example 22a, 85.5 mg tribromoborane and 2000 μL DCM was stirred under ice cooling for 30 min and gave, after working-up and purification, 5.7 mg (22%) of the title compound.

$^1$H-NMR (DMSO-$d_6$): δ=0.44-0.52 (2H), 0.64 (2H), 2.15 (3H), 2.59-2.73 (2H), 2.78 (1H), 3.61 (2H), 5.59 (1H), 6.17 (1H), 6.41 (1H), 6.79 (1H), 7.00 (2H), 7.15 (1H), 7.41 (1H), 7.71-7.78 (1H), 7.84 (1H), 7.98 (1H), 8.20 (1H), 9.21 (1H) ppm.

Intermediate Example 22a

N-cyclopropyl-4-{6-[1-(5-fluoro-2-methoxyphenyl)ethenyl]-8-[(3,3,3-trifluoropropyl)amino]imidazo[1,2-b]pyridazin-3-yl}-2-methylbenzamide

Intermediate Example 22b

N-cyclopropyl-4-{6-(5-fluoro-2-methoxybenzoyl)-8-[(3,3,3-trifluoropropyl)amino]imidazo[1,2-b]pyridazin-3-yl}-2-methylbenzamide

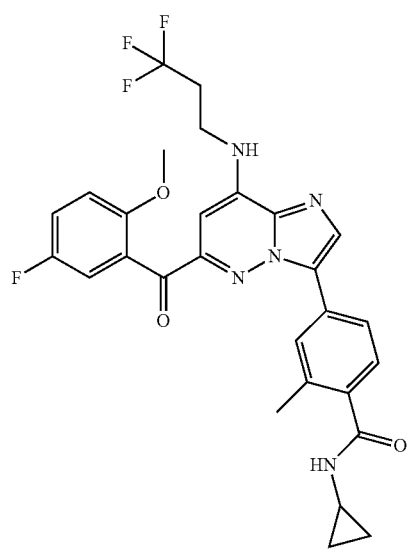
→

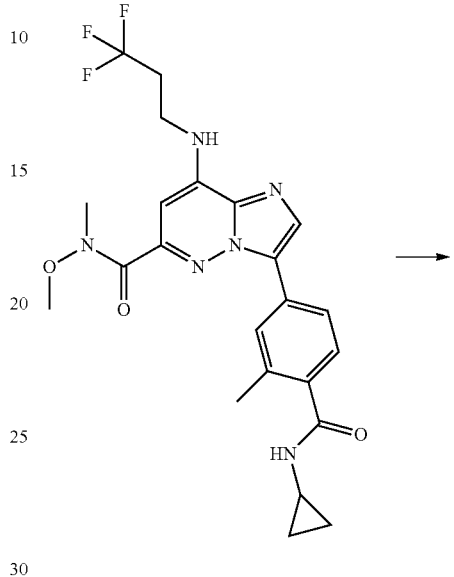
→

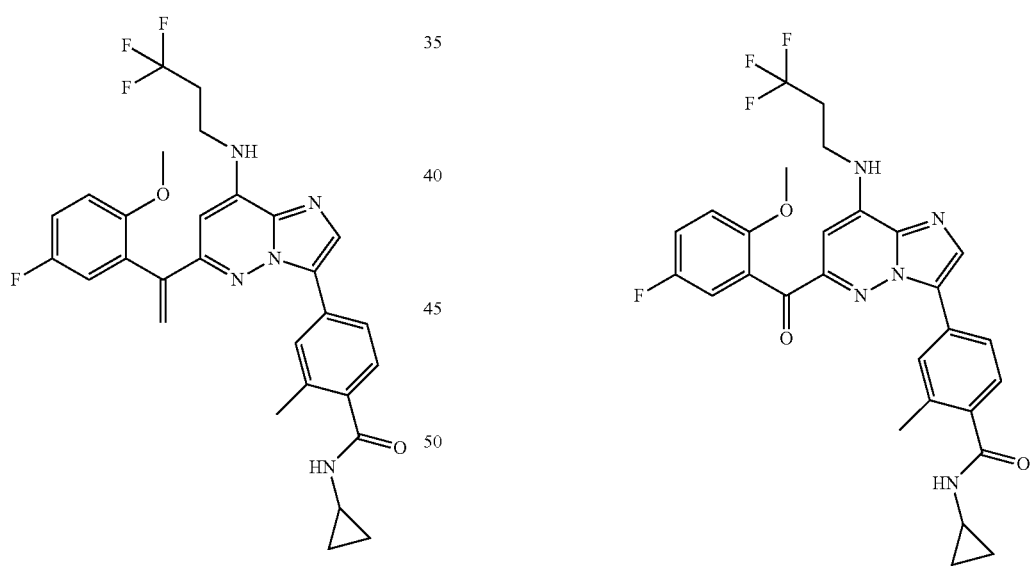

1740 mg (1.16 mmol) N-cyclopropyl-4-{6-(5-fluoro-2-methoxybenzoyl)-8-[(3,3,3-trifluoropropyl)amino]imidazo[1,2-b]pyridazin-3-yl}-2-methylbenzamide which was prepared according to intermediate example 22b were transformed in analogy to example 1 to give after working up 1270 mg (73%) of the title compound.

$^1$H-NMR (DMSO-d$_6$): δ=0.43-0.52 (2H), 0.59-0.69 (2H), 2.14 (3H), 2.57-2.73 (2H), 2.73-2.84 (1H), 3.50 (3H), 3.56-3.67 (2H), 5.59 (1H), 6.25 (1H), 6.45 (1H), 6.98-7.16 (3H), 7.19 (1H), 7.46 (1H), 7.71 (1H), 7.78 (1H), 8.00 (1H), 8.23 (1H) ppm.

2000 mg (4.078 mmol) 3-[4-(cyclopropylcarbamoyl)-3-methylphenyl]-N-methoxy-N-methyl-8-[(3,3,3-trifluoropropyl)amino]imidazo[1,2-b]pyridazine-6-carboxamide which was prepared according to comparative example 3c were transformed in analogy to comparative example 3b using bromo(5-fluoro-2-methoxyphenyl)magnesium to give after working up 1740 mg (77%) of the title compound.

$^1$H-NMR (DMSO-d$_6$): δ=0.43-0.51 (2H), 0.60-0.69 (2H), 2.13 (3H), 2.62-2.83 (4H), 3.60 (3H), 3.70 (2H), 6.75 (1H), 7.15 (1H), 7.21 (1H), 7.33-7.46 (2H), 7.72 (1H), 7.80 (1H), 7.92 (1H), 8.18 (1H), 8.25 (1H) ppm.

Example 23

N-cyclopropyl-4-{6-[1-(5-fluoro-2-hydroxyphenyl)cyclopropyl]-8-[(3,3,3-trifluoropropyl)amino]imidazo[1,2-b]pyridazin-3-yl}-2-methylbenzamide

Intermediate Example 23a 4-(6-{1-[2-(benzyloxy)-5-fluorophenyl]cyclopropyl}-8-[(3,3,3-trifluoropropyl)amino]imidazo[1,2-b]pyridazin-3-yl)-N-cyclopropyl-2-methylbenzamide

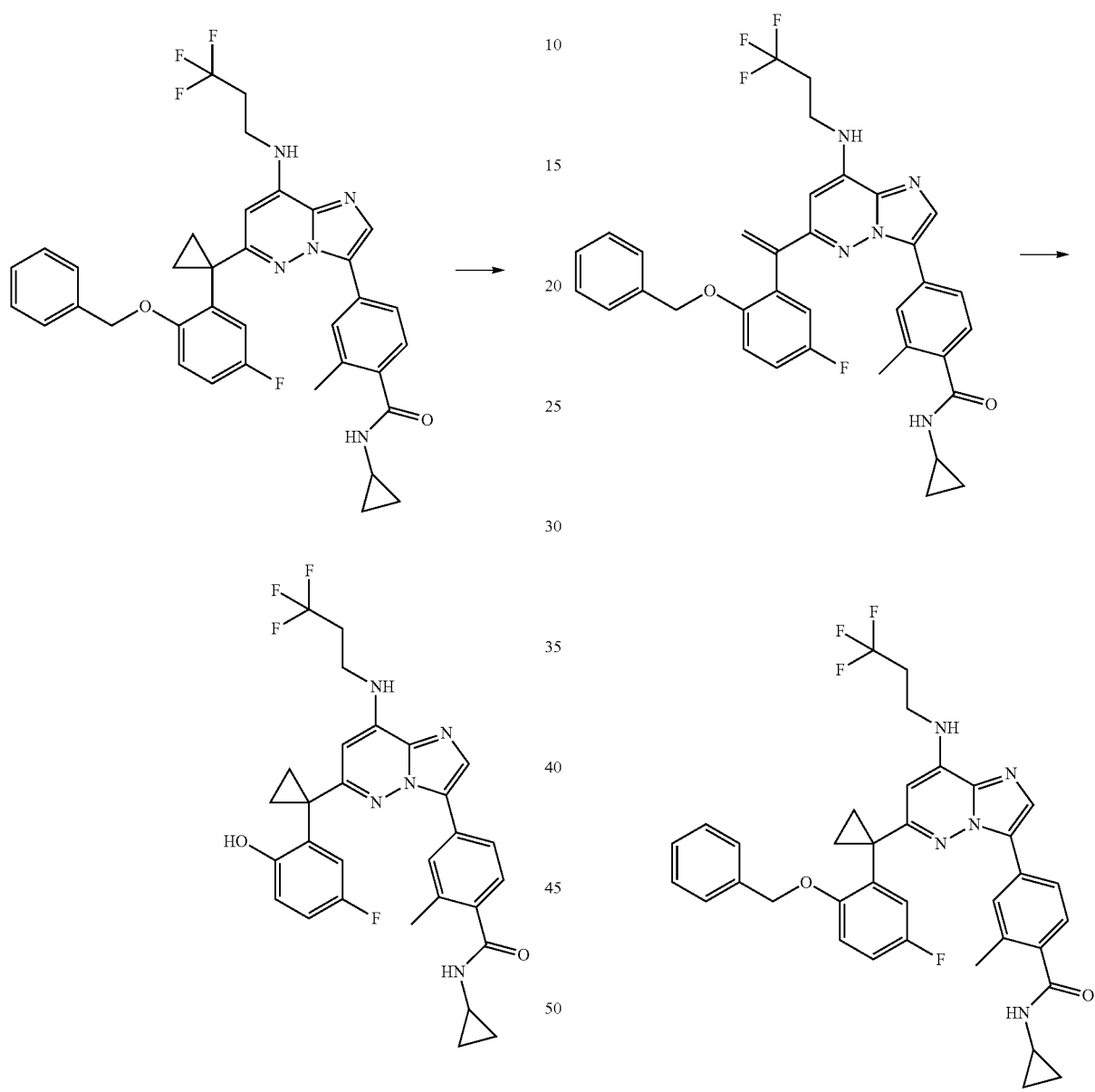

A mixture of 584 mg (907 μmol) 4-(6-{1-[2-(benzyloxy)-5-fluorophenyl]cyclopropyl}-8-[(3,3,3-trifluoropropyl)amino]imidazo[1,2-b]pyridazin-3-yl)-N-cyclopropyl-2-methylbenzamide which was prepared according to intermediate example 23a and 50 mg Pd/C in 50 mL ethanol7HOAC 8:2 was stirred at rt under a hydrogen atmosphere at 1 atm for 8 days and gave, after working-up 68 mg (14%) of the title compound.

$^1$H-NMR (DMSO-$d_6$): δ=0.47-0.58 (2H), 0.63-0.72 (2H), 1.21-1.29 (2H), 1.55-1.63 (2H), 2.51-2.65 (3H), 2.82 (1H), 3.46 (2H), 5.75 (1H), 6.81 (1H), 6.93-7.03 (1H), 7.11 (1H), 7.27 (1H), 7.37 (1H), 7.85-8.01 (3H), 8.30 (1H), 9.33 (1H) ppm.

2060 mg crude (3.27 mmol) 4-(6-{1-[2-(benzyloxy)-5-fluorophenyl]ethenyl}-8-[(3,3,3-trifluoropropyl)amino]imidazo[1,2-b]pyridazin-3-yl)-N-cyclopropyl-2-methylbenzamide which was prepared according to intermediate example 23b were transformed in analogy to example 17 to give after working up and purification 692 mg (33%) of the title compound.

$^1$H-NMR (DMSO-$d_6$): δ=0.49-0.57 (2H), 0.64-0.73 (2H), 1.26-1.33 (2H), 1.58-1.66 (2H), 2.31 (3H), 2.42-2.55 (2H), 2.83 (1H), 3.41 (2H), 4.98 (2H), 5.72 (1H), 6.97-7.04 (2H), 7.05-7.11 (4H), 7.14 (1H), 7.25-7.30 (2H), 7.32 (1H), 7.83-7.88 (1H), 7.92 (1H), 7.96 (1H), 8.26 (1H) ppm.

Intermediate Example 23b 4-(6-{1-[2-(benzyloxy)-5-fluorophenyl]but-3-en-1-yl}-8-[(3,3,3-trifluoropropyl)amino]imidazo[1,2-b]pyridazin-3-yl)-N-cyclopropyl-2-methylbenzamide

Intermediate Example 23c

4-{6-[2-(benzyloxy)-5-fluorobenzoyl]-8-[(3,3,3-trifluoropropyl)amino]imidazo[1,2-b]pyridazin-3-yl}-N-cyclopropyl-2-methylbenzamide

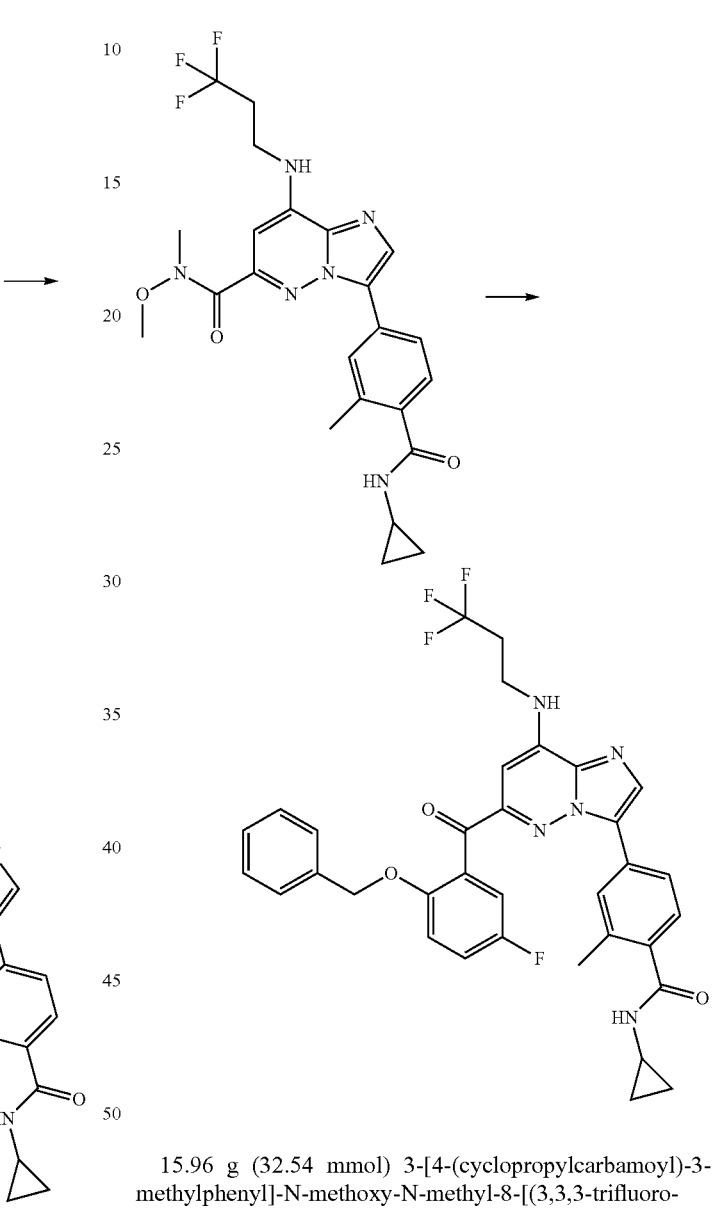

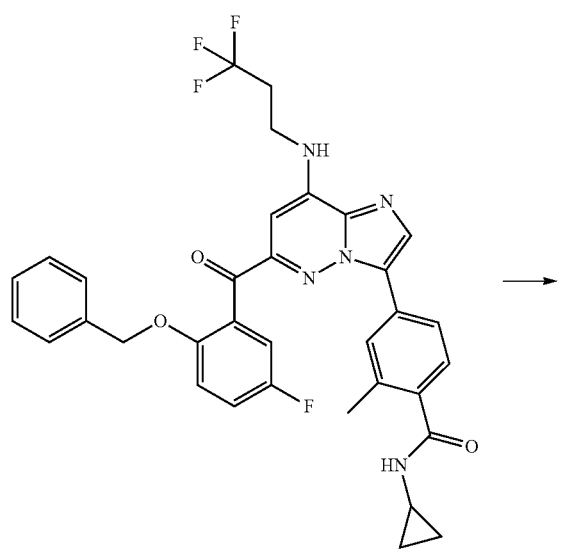

14.06 g (22.26 mmol) 4-{6-[2-(benzyloxy)-5-fluorobenzoyl]-8-[(3,3,3-trifluoropropyl)amino]imidazo[1,2-b]pyridazin-3-yl}-N-cyclopropyl-2-methylbenzamide which was prepared according to intermediate example 23c were transformed in analogy to example 1 to give after working up 21.83 g (150%) of the crude title compound which was used without further purification in the next step.

$^1$H-NMR (DMSO-$d_6$): δ=0.46-0.54 (2H), 0.62-0.70 (2H), 2.14 (3H), 2.52-2.68 (2H), 2.74-2.87 (1H), 3.59 (2H), 4.84 (2H), 5.65 (1H), 6.16 (1H), 6.39 (1H), 6.77 (2H), 6.93 (2H), 7.02-7.29 (5H), 7.43 (1H), 7.74 (1H), 7.82 (1H), 8.03 (1H), 8.21 (1H) ppm.

15.96 g (32.54 mmol) 3-[4-(cyclopropylcarbamoyl)-3-methylphenyl]-N-methoxy-N-methyl-8-[(3,3,3-trifluoropropyl)amino]imidazo[1,2-b]pyridazine-6-carboxamide which was prepared according to comparative example 3c in 300 mL THF were transformed in analogy to comparative example 3b using a freshly prepared solution of [2-(benzyloxy)-5-fluorophenyl](bromo)magnesium (231 mmol in 200 mL THF) to give after working up 13.26 g (64.5%) of the title compound.

$^1$H-NMR (DMSO-$d_6$): δ=0.47-0.56 (2H), 0.62-0.71 (2H), 2.12 (3H), 2.67 (2H), 2.80 (1H), 3.68 (2H), 4.96 (2H), 6.68 (1H), 6.83 (2H), 6.97 (2H), 7.07 (1H), 7.18 (1H), 7.32 (1H), 7.40-7.50 (2H), 7.73 (1H), 7.81 (1H), 7.88 (1H), 8.20 (1H), 8.24 (1H) ppm.

Intermediate Example 23d

[2-(benzyloxy)-5-fluorophenyl](bromo)magnesium

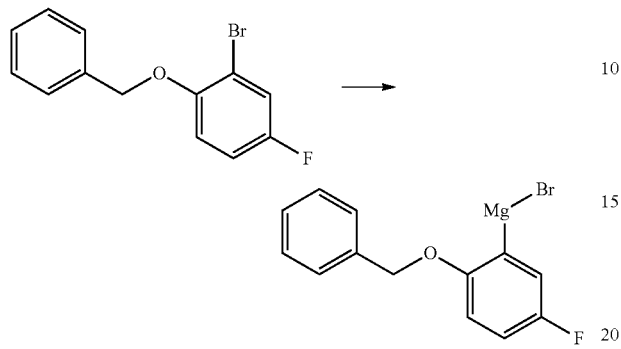

To stirred suspension of 5.62 g (231 mmol) magnesium in 100 mL THF were added at rt under an argon atmosphere one crystal of iodine and dropwise 40 mL of a solution of 64.95 g (231 mmol) 1-(benzyloxy)-2-bromo-4-fluorobenzene in 100 mL THF. The mixture was heated to 60° C. until decolorization and the remaining solution of 1-(benzyloxy)-2-bromo-4-fluorobenzene was added dropwise while keeping the temperature at 50° C.

After cooling to rt, the Grignard solution was directly used for intermediate example 23c.

Example 24

N-cyclopropyl-4-{6-[1-(3-fluorophenyl)ethenyl]-8-[(3,3,3-trifluoropropyl)amino]imidazo[1,2-b]pyridazin-3-yl}-2-methylbenzamide

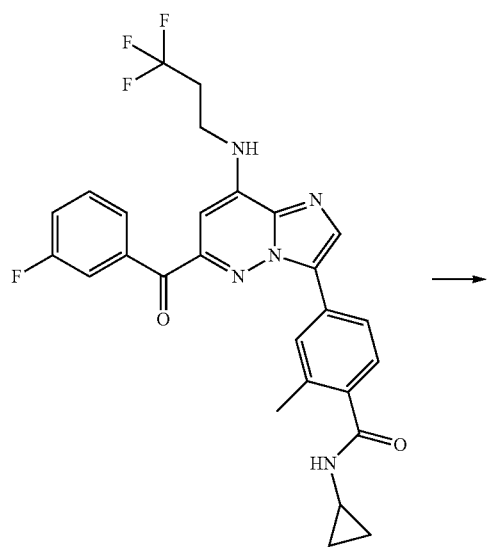

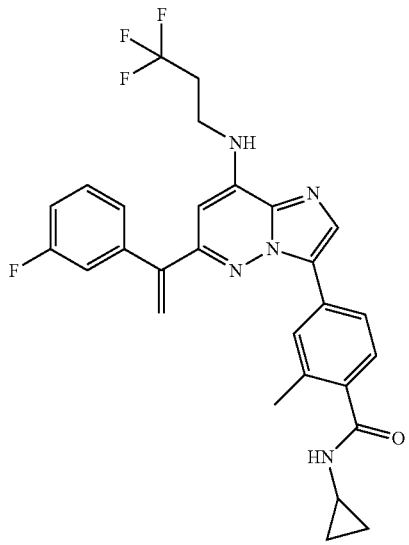 [SMILES: C=C(c1cccc(F)c1)c1cc(NCCC(F)(F)F)c2ncc(-c3ccc(C(=O)NC4CC4)c(C)c3)n2n1]

80.0 mg (152 µmol) N-cyclopropyl-4-{6-(3-fluorobenzoyl)-8-[(3,3,3-trifluoropropyl)amino]imidazo[1,2-b]pyridazin-3-yl}-2-methylbenzamide which was prepared according to comparative example 3b were transformed in analogy to example 1 to give after working up and purification 27 mg (33.7%) of the title compound.

$^1$H-NMR (DMSO-d$_6$): δ=0.44-0.51 (2H), 0.60-0.66 (2H), 2.16 (3H), 2.59-2.72 (2H), 2.77 (1H), 3.62 (2H), 5.81 (1H), 6.06 (1H), 6.41 (1H), 7.15-7.23 (2H), 7.23-7.30 (2H), 7.38-7.47 (1H), 7.55 (1H), 7.77-7.83 (1H), 7.85 (1H), 8.01 (1H), 8.20 (1H) ppm.

Example 25

N-cyclopropyl-4-{6-[1-(3-fluorophenyl)cyclopropyl]-8-[(3,3,3-trifluoropropyl)amino]imidazo[1,2-b]pyridazin-3-yl}-2-methylbenzamide

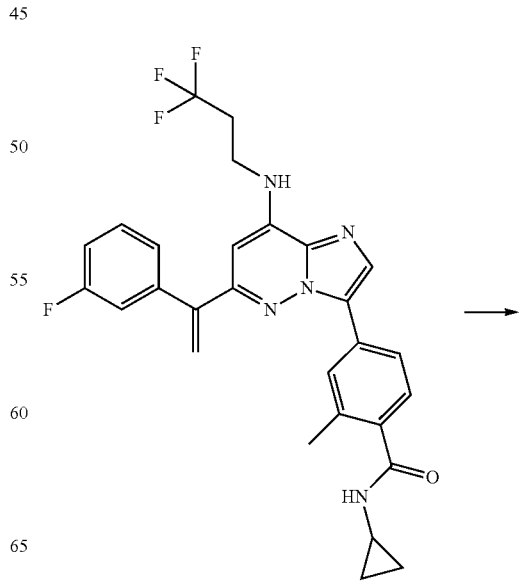

-continued

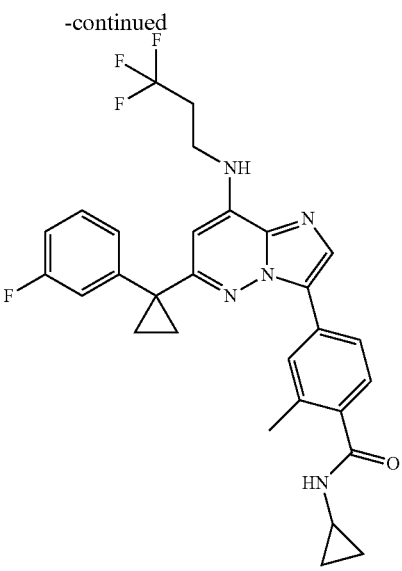

27.0 mg (52 µmol) N-cyclopropyl-4-{6-[1-(3-fluorophenyl)ethenyl]-8-[(3,3,3-trifluoropropyl)amino]imidazo[1,2-b]pyridazin-3-yl}-2-methylbenzamide which was prepared according to example 23 were transformed in analogy to example 1 to give after working up and purification 9 mg (32%) of the title compound.

$^1$H-NMR (DMSO-d$_6$): δ=0.47-0.53 (2H), 0.61-0.69 (2H), 1.32-1.38 (2H), 1.54-1.59 (2H), 2.32 (3H), 2.57 (2H), 2.80 (1H), 3.51 (2H), 5.99 (1H), 7.03-7.11 (1H), 7.14-7.23 (2H), 7.27-7.40 (2H), 7.51 (1H), 7.84-7.91 (2H), 8.08 (1H), 8.26 (1H) ppm.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science a Technology 1998, 52(5), 238-311; Strickley, R. G "Parenteral Formulations of Small Molecule Therapeutics Marketed in the United States (1999)—Part-1" PDA Journal of Pharmaceutical Science Et Technology 1999, 53(6), 324-349; and Nema, S. et al., "Excipients and Their Use in Injectable Products" PDA Journal of Pharmaceutical Science Et Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised Powder for IV Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisonnerase inhibitors, biological response modifiers, or anti-hormones.

The additional pharmaceutical agent can be 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, ertotinib, estradiot, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofuran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Preferably, the additional pharmaceutical agent is selected from: afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib (BAY 43-9006), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, and zoledronic acid or combinations thereof.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, epothilone, an epothilone derivative, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-linked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

The compounds of the invention may also be combined with biological therapeutic agents, such as antibodies (e.g. avastin, rituxan, erbitux, herceptin), or recombinant proteins.

The compounds of the invention may also be in combination with antiangiogenesis agents, such as, for example, with avastin, axitinib, DAST, recentin, sorafenib or sunitinib. Combinations with inhibitors of proteasomes or mTOR inhibitors, or anti-hormones or steroidal metabolic enzyme inhibitors are also possible.

Generally, the use of cytotoxic and/or cytostatic agents in combination with a compound or composition of the present invention will serve to:
(1) yield better efficacy in reducing the growth of a tumour or even eliminate the tumour as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumour progression, and/or
(8) yield efficacy and tolerability results at least as good as those of the agents used atone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula I, or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula I described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers. Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assay: Proliferation Assay

Cultivated tumour cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (816F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (C-terminus in amide form, purchased from Biosynthan GmbH, Berlin) was used.

For the assay 50 nL of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM $MgCl_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jügesheim, Germany].

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

TABLE 1

| Example | Mps-1 $IC_{50}$ [nM] |
|---|---|
| 1 | 0.4 |
| 2 | 0.6 |
| 3 | 0.2 |
| 4 | 0.3 |
| 5 | 0.7 |
| 6 | 0.7 |
| 7 | 0.5 |
| 8 | 0.8 |
| 9 | 1.2 |
| 10 | 0.5 |
| 11 | 0.3 |
| 12 | 0.6 |
| 13 | 0.4 |
| 14 | 0.6 |
| 15 | 0.4 |
| 16 | 0.6 |
| 17 | 0.7 |
| 18 | 1.5 |
| 19 | 0.6 |
| 20 | 0.8 |
| 21 | 0.5 |
| 22 | 0.4 |
| 23 | 0.4 |
| 24 | 0.3 |
| 25 | 0.9 |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumour cell line HeLa (ATCC CCL-2) were plated at a density of 2500 cells/well in a 384-well microtiter plate in 20 µl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. After 24 h incubation, cells were arrested at G2M phase of the cell cycle progression. Test compounds solubilised in dimethyl sulfoxide (DMSO) were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 µl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 µl/well HOECHST 33342 dye solution (5 µg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0×10^6$ vital cells/ml. The test compound was added to a final concentration of 1 µM. During incubation, the hepatocyte suspensions were continuously shaken and aliquots were taken at 2, 8, 16, 30, 45 and 90 min, to which equal volumes of cold methanol were immediately added.

Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated. The following parameter values were used: Liver blood flow—4.2 L/h/kg rat; specific liver weight—32 g/kg rat body weight; liver cells in vivo—$1.1×10^8$ cells/g liver, liver cells in vitro—$0.5×10^6$ ml.

Tables 2, 3, 4, 5 and 6 compare the in vitro metabolic stability in rat hepatocytes expressed as hepatic in vivo blood clearance (CL) and the maximal oral bioavailability ($F_{max}$) for three sets of compounds.

Each set comprises a comparative compound bearing a —$CH_2$—$R^{3c}$— group for $R^3$ that is compared with two compounds bearing a —$C(R^{3a})(R^{3b})$—$R^{3c}$— group.

The remaining substitution pattern in each set is conserved to allow an assessment of the influence of $R^{3a}$ and $R^{3b}$ on the hepatic in vivo blood clearance and the maximal oral bioavailability.

The set of compounds given in Table 2 clearly indicates an improved hepatic in vivo blood clearance and an improved maximal oral bioavailability if both $R^{3a}$ and $R^{3b}$ do not represent a hydrogen atom.

TABLE 2

| Example | Comparative Example 1 | Example 1 | Example 2 | Example 13 |
|---|---|---|---|---|
| $F_{max}$ [%] | 29 | 39 | 64 | 75 |
| CL [L/h/kg] | 3.0 | 2.6 | 1.5 | 1.1 |

The set of compounds given in Table 3 clearly indicates an improved hepatic in vivo blood clearance and an improved maximal oral bioavailability if at least one of $R^{3a}$ and $R^{3b}$ does not represent a hydrogen atom.

TABLE 3

| Example | Comparative Example 2 | Example 3 | Example 4 |
|---|---|---|---|
| $F_{max}$ [%] | 3 | 18 | 36 |
| CL [L/h/kg] | 4.1 | 3.4 | 2.7 |

The set of compounds given in Table 4 clearly indicates an improved hepatic in vivo blood clearance and an improved maximal oral bioavailability if at least one of $R^{3a}$ and $R^{3b}$ does not represent a hydrogen atom.

TABLE 4
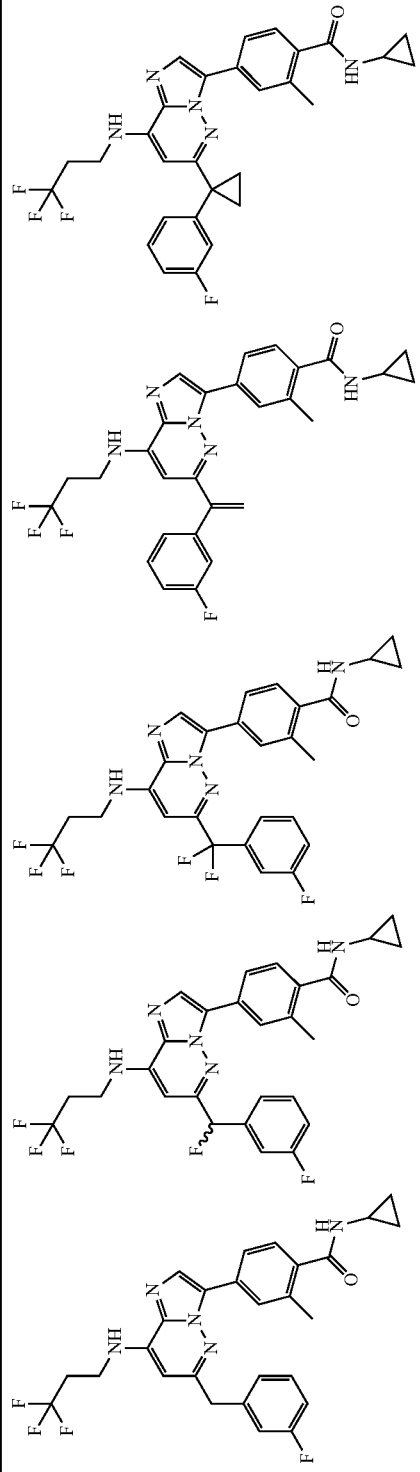
| Example | Comparative Example 3 | Example 5 | Example 6 | Example 24 | Example 25 |
|---|---|---|---|---|---|
| $F_{max}$ [%] | 43 | 49 | 70 | 48 | 52 |
| CL [L/h/kg] | 2.4 | 2.1 | 1.3 | 2.2 | 2.0 |

The set of compounds given in Table 5 clearly indicate an improved hepatic in vivo blood clearance and an improved maximal oral bioavailability if both $R^{3a}$ and $R^{3b}$ do not represent a hydrogen atom.

TABLE 5

| Example | Comparative Example 4 | Example 7 | Example 8 |
|---|---|---|---|
| $F_{max}$ [%] | 18 | 26 | 57 |
| CL [L/h/kg] | 3.4 | 3.1 | 1.8 |

The set of compounds given in Table 6 clearly indicate an improved hepatic in vivo blood clearance and an improved maximal oral bioavailability if both $R^{3a}$ and $R^{3b}$ do not represent a hydrogen atom.

TABLE 6

| Example | Comparative Example 5 | Example 9 | Example 10 | Example 16 |
|---|---|---|---|---|
| $F_{max}$ [%] | 35 | 71 | 48 | 56 |
| CL [L/h/kg] | 2.7 | 1.2 | 2.2 | 1.9 |

Table 7 lists hepatic in vivo blood clearance and the maximal oral bioavailability of additional compounds for which both, $R^{3a}$ and $R^{3b}$, do not represent a hydrogen atom.

TABLE 7

| Example | $F_{max}$ [%] | CL [L/h/kg] |
|---------|---------------|-------------|
| 11 | 45 | 2.3 |
| 12 | 67 | 1.4 |
| 14 | 51 | 2.1 |
| 15 | 53 | 2.0 |
| 17 | 50 | 2.1 |
| 18 | 76 | 1.0 |
| 22 | 28 | 3.0 |
| 23 | 40 | 2.5 |

The data given in Tables 2, 3, 4, 5, 6 and 7 clearly indicate that the hepatic in vivo blood clearance as well as the maximal oral bioavailability of the whole molecule can be surprisingly improved if at least one of $R^{3a}$ and $R^{3b}$ does not represent a hydrogen atom.

The invention claimed is:

1. A compound of general formula I:

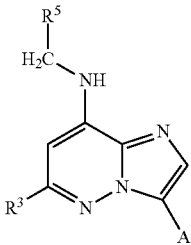

in which:
A represents

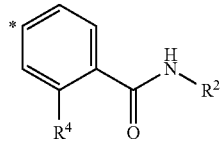

wherein * indicates the point of attachment of said group with the rest of the molecule;
$R^2$ represents a cyclopropyl- group;
$R^3$ represents
—C($R^{3a}$)($R^{3b}$)($R^{3c}$);
$R^{3a}$, $R^{3b}$
represent, independently from each other, a hydrogen atom or a fluorine atom or a hydroxy-, or a methyl-group, with the proviso that not both of $R^{3a}$ and $R^{3b}$ represent a hydrogen atom and not both of $R^{3a}$ and $R^{3b}$ represent a hydroxy group;
or
$R^{3a}$, $R^{3b}$
together represent =O or =C($R^{3d}$)($R^{3e}$);
or
$R^{3a}$, $R^{3b}$
together with the carbon atom they are attached to, form a cyclopropyl- ring;
$R^{3c}$ represents a phenyl group;

wherein said phenyl group is substituted, identically or differently, with 1, 2, or 3 $R^7$ groups;
$R^{3d}$, $R^{3e}$
represent a hydrogen atom;
$R^4$ represents a methyl group;
$R^5$ represents —$CH_2$—$CF_3$;
$R^7$ represents a fluorine atom, or a hydroxy-, or a methoxy group;
or a stereoisomer, a tautomer, an N-oxide, a hydrate, a solvate, or a salt thereof, or a mixture of same.

2. A compound according to claim 1, wherein
$R^{3a}$, $R^{3b}$
together with the carbon atom they are attached to, form a cyclopropyl-ring; or a stereoisomer, a tautomer, an N-oxide, a hydrate, a solvate, or a salt thereof, or a mixture of same.

3. A compound according to claim 1, which is selected from the group consisting of:
N-cyclopropyl-4-{6-[1-(3-fluoro-4-methoxyphenyl)ethenyl]-8-[(3,3,3-trifluoropropyl)amino]imidazo[1,2-b]pyridazin-3-yl}-2-methylbenzamide,
N-cyclopropyl-4-{6-[difluoro(3-fluoro-4-methoxyphenyl)methyl]-8-[(3,3,3-trifluoropropyl)amino]imidazo[1,2-b]pyridazin-3-yl}-2-methylbenzamide,
(RS)—N-cyclopropyl-4-{6-[(3-fluoro-2-hydroxyphenyl)(hydroxy)methyl]-8-[(3,3,3-trifluoropropyl)amino]imidazo[1,2-b]pyridazin-3-yl}-2-methylbenzamide,
(R)—N-cyclopropyl-4-{6-[(3-fluoro-2-hydroxyphenyl)(hydroxy)methyl]-8-[(3,3,3-trifluoropropyl)amino]imidazo[1,2-b]pyridazin-3-yl}-2-methylbenzamide,
(S)—N-cyclopropyl-4-{6-[(3-fluoro-2-hydroxyphenyl)(hydroxy)methyl]-8-[(3,3,3-trifluoropropyl)amino]imidazo[1,2-b]pyridazin-3-yl}-2-methylbenzamide,
(RS)—N-cyclopropyl-4-{6-[1-(3-fluoro-2-hydroxyphenyl)-1-hydroxyethyl]-8-[(3,3, 3-trifluoropropyl)amino]imidazo[1,2-b]pyridazin-3-yl}-2-methylbenzamide,
(R)—N-cyclopropyl-4-{6-[1-(3-fluoro-2-hydroxyphenyl)-1-hydroxyethyl]-8-[(3,3,3-trifluoropropyl)amino]imidazo[1,2-b]pyridazin-3-yl}-2-methylbenzamide,
(S)—N-cyclopropyl-4-{6-[1-(3-fluoro-2-hydroxyphenyl)-1-hydroxyethyl]-8-[(3,3,3-trifluoropropyl)amino]imidazo[1,2-b]pyridazin-3-yl}-2-methylbenzamide,
(RS)—N-cyclopropyl-4-{6-[fluoro(3-fluorophenyl)methyl]-8-[(3, 3,3-trifluoropropyl)amino]imidazo[1,2-b]pyridazin-3-yl}-2-methylbenzamide,
(R)—N-cyclopropyl-4-{6-[fluoro(3-fluorophenyl)methyl]-8-[(3, 3,3-trifluoropropyl)amino]imidazo[1,2-b]pyridazin-3-yl}-2-methylbenzamide,
(S)—N-cyclopropyl-4-{6-[fluoro(3-fluorophenyl)methyl]-8-[(3, 3,3-trifluoropropyl)amino]imidazo[1,2-b]pyridazin-3-yl}-2-methylbenzamide,
N-cyclopropyl-4-{6-[difluoro(3-fluorophenyl)methyl]-8-[(3,3,3-trifluoropropyl)amino]imidazo[1,2-b]pyridazin-3-yl}-2-methylbenzamide,
N-cyclopropyl-4-{6-(3-methoxybenzoyl)-8-[(3,3,3-trifluoropropyl)amino]imidazo[1,2-b]pyridazin-3-yl}-2-methylbenzamide,
N-cyclopropyl-4-{6-[1-(3-methoxyphenyl)vinyl]-8-[(3,3,3-trifluoropropyl)amino]imidazo[1,2-b]pyridazin-3-yl}-2-methylbenzamide,
N-cyclopropyl-4-{6-(4-methoxybenzoyl)-8-[(3,3,3-trifluoropropyl)amino]imidazo[1,2-b]pyridazin-3-yl}-2-methylbenzamide,
N-cyclopropyl-4-{6-[1-(4-methoxyphenyl)vinyl]-8-[(3, 3,3-trifluoropropyl)amino]imidazo[1, 2-b]pyridazin-3-yl}-2-methylbenzamide, N-cyclopropyl-4-{6-[(2,5-difluorophenyl)(hydroxy)methyl]-8-[(3,3,3-trifluoropropyl)amino]imidazo[1,2-b]pyridazin-3-yl}-2-methylbenzamide,
N-cyclopropyl-4-{6-(2,5-difluorobenzoyl)-8-[(3,3,3-trifluoropropyl)amino]imidazo[1,2-b]pyridazin-3-yl}-2-methylbenzamide,
N-cyclopropyl-4-{6-(3-fluoro-4-methoxybenzoyl)-8-[(3,3,3-trifluoropropyl)amino]imidazo[1,2-b]pyridazin-3-yl}-2-methylbenzamide,
N-cyclopropyl-4-{6-(2,3-difluorobenzoyl)-8-[(3,3,3-trifluoropropyl)amino]imidazo[1,2-b]pyridazin-3-yl}-2-methylbenzamide,
N-cyclopropyl-4-{6-[1-(2,3-difluorophenyl)vinyl]-8-[(3,3,3-trifluoropropyl)amino]imidazo[1,2-b]pyridazin-3-yl}-2-methylbenzamide,
N-cyclopropyl-4-{6-[difluoro(4-methoxyphenyl)methyl]-8-[(3,3,3-trifluoropropyl)amino]imidazo[1,2-b]pyridazin-3-yl}-2-methylbenzamide,
N-cyclopropyl-4-{6-[1-(2,3-difluorophenyl)cyclopropyl]-8-[(3,3,3-trifluoropropyl)amino]imidazo[1,2-b]pyridazin-3-yl}-2-methylbenzamide,
N-cyclopropyl-4-{6-[(2,3-difluorophenyl)(difluoro)methyl]-8-[(3,3,3-trifluoropropyl)amino]imidazo[1,2-b]pyridazin-3-yl}-2-methylbenzamide,
N-cyclopropyl-4-{6-[1-(2,5-difluorophenyl)vinyl]-8-[(3,3,3-trifluoropropyl)amino]imidazo[1,2-b]pyridazin-3-yl}-2-methylbenzamide,
N-cyclopropyl-4-{6-[1-(2,5-difluorophenyl)cyclopropyl]-8-[(3,3,3-trifluoropropyl)amino]imidazo[1,2-b]pyridazin-3-yl}-2-methylbenzamide,
N-cyclopropyl-4-{6-[(2,5-difluorophenyl)(difluoro)methyl]-8-[(3,3,3-trifluoropropyl)amino]imidazo[1,2-b]pyridazin-3-yl}-2-methylbenzamide,
N-cyclopropyl-4-{6-[1-(5-fluoro-2-hydroxyphenyl)ethenyl]-8-[(3,3,3-trifluoropropyl)amino]imidazo[1,2-b]pyridazin-3-yl}-2-methylbenzamide, and
N-cyclopropyl-4-{6-[1-(5-fluoro-2-hydroxyphenyl)cyclopropyl]-8-[(3,3,3-trifluoropropyl)amino]imidazo[1,2-b]pyridazin-3-yl}-2-methylbenzamide,
or a stereoisomer, a tautomer, an N-oxide, a hydrate, a solvate, or a salt thereof, or a mixture of same.

4. A method of preparing a compound according to claim 1, said method comprising the step of allowing an intermediate compound of general formula Ia:

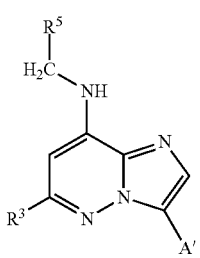

in which $R^3$ and $R^5$ are as defined in claim 1; and A' is

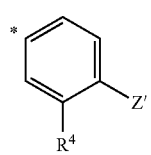

wherein * indicates the point of attachment of said group with the rest of the molecule; $R^4$ is as defined in claim 1, and Z' represents a group selected from: —C(=O)OH and —C(=O)O—($C_1$-$C_6$-alkyl);

to react with a compound of general formula Ib:

$$H_2NR^2 \qquad \qquad \text{Ib}$$

in which $R^2$ is as defined in claim 1, thereby giving, upon optional deprotection, a compound of general formula I:

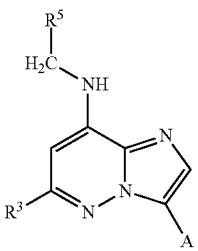

in which $R^3$, $R^5$ and A are as defined claim 1.

5. A method of preparing a compound according to claim 1, said method comprising the step of allowing an intermediate compound of general formula VII:

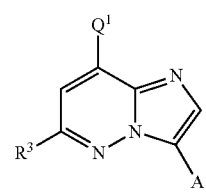

in which $R^3$ and A are as defined in claim 1, and $Q^1$ is a leaving group, to react with a compound of general formula VIIa:

$$R^5—CH_2—NH_2 \qquad \text{VIIa}$$

in which $R^5$ is as defined in claim 1, thereby giving, upon optional deprotection, a compound of general formula I:

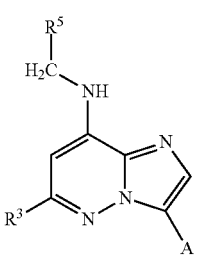

in which $R^3$, $R^5$ and A are as defined in claim 1.

6. A method of preparing a compound according to claim 1, said method comprising the step of conversion of an intermediate compound of general formula XVII:

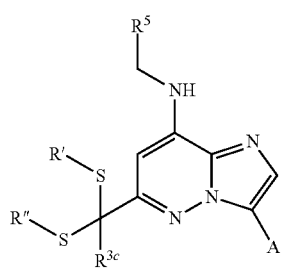

XVII in which $R^{3c}$, $R^5$ and A are as defined in claim 1; and
R' and R" represent, independent from each other, a $C_1$-$C_6$-alkyl- group; or
R' and R" together represent an alkylene group;
to a compound of general formula XIII:

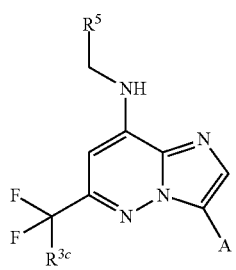

XIII in which $R^{3c}$, $R^5$ and A are as defined in claim 1.

7. A method of preparing a compound according to claim 1, said method comprising the step of conversion of an intermediate compound of general formula XXI:

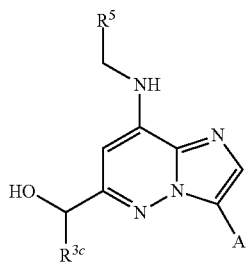

XXI in which $R^{3c}$, $R^5$ and A are as defined in claim 1;
to a compound of general formula XX:

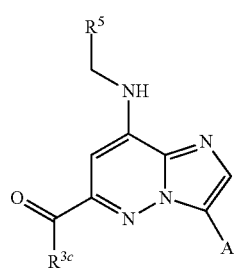

XX in which $R^{3c}$, $R^5$ and A are as defined in claim 1.

8. A method of preparing a compound according to claim 1, said method comprising the step of conversion of an intermediate compound of general formula XIX:

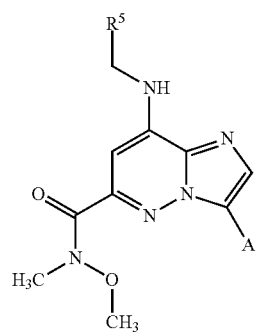

XIX in which $R^5$ and A are as defined in claim 1;
to a compound of general formula XX:

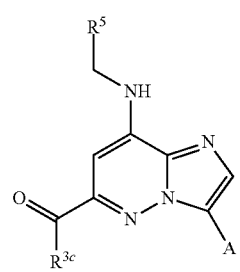

XX in which $R^{3c}$, $R^5$ and A are as defined in claim 1.

9. A method of preparing a compound according to claim 1, said method comprising the step of conversion of an intermediate compound of general formula XXII:

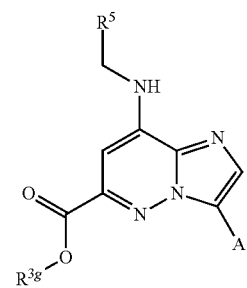

XXII in which $R^5$ and A are as defined in claim 1; and
$R^{3g}$ is a hydrogen atom or a $C_1$-$C_6$-alkyl- group;

to a compound of general formula XX:

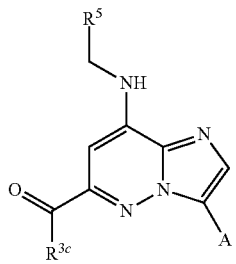

XX in which $R^{3c}$, $R^5$ and A are as defined in claim 1.

10. A method of preparing a compound according to claim 1, said method comprising the step of conversion of an intermediate compound of general formula XXI:

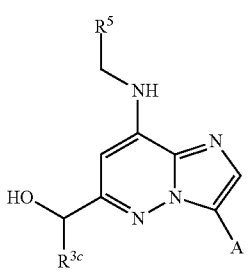

XXI in which $R^5$, $R^{3c}$ and A are as defined in claim 1; to a compound of general formula XVIII:

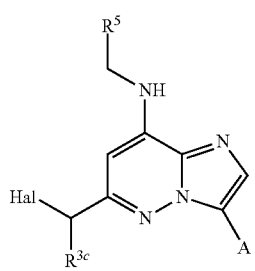

XVIII in which $R^{3c}$, $R^5$ and A are as defined in claim 1, and Hal is a fluorine atom.

11. A method of preparing a compound according to claim 1, said method comprising the step of conversion of an intermediate compound of general formula XX:

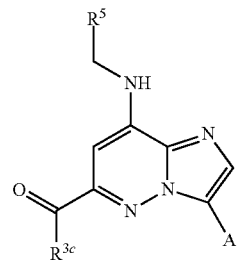

XX in which $R^5$, $R^{3c}$ and A are as defined in claim 1; to a compound of general formula XVI:

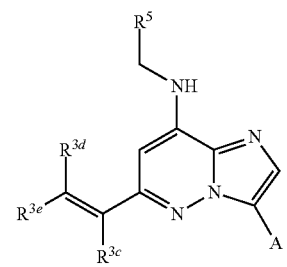

XVI in which $R^{3c}$, $R^{3d}$, $R^{3e}$, $R^5$ and A are as defined in claim 1.

12. A method of preparing a compound according to claim 1, said method comprising the step of conversion of an intermediate compound of general formula XVI:

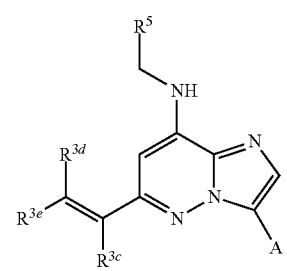

XVI in which $R^{3c}$, $R^{3d}$, $R^{3e}$, $R^5$ and A are as defined in claim 1; to a compound of general formula XXV:

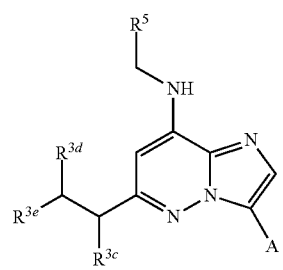

XXV in which $R^{3c}$, $R^{3d}$, $R^{3e}$, $R^5$ and A are as defined in claim 1.

13. A method of preparing a compound according to claim 1, said method comprising the step of conversion of an intermediate compound of general formula XVI:

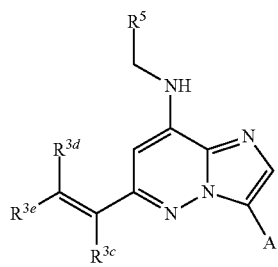

in which $R^{3c}$, $R^{3d}$, $R^{3e}$, $R^5$ and A are as defined in claim 1;
to a compound of general formula XII:

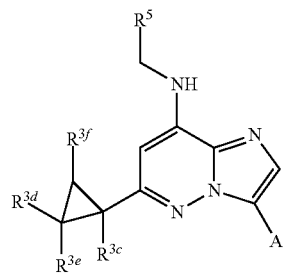

in which $R^{3c}$, $R^{3d}$, $R^{3e}$, $R^5$ and A are as defined in claim 1, and $R^{3f}$ is a hydrogen atom.

14. A method of preparing a compound according to claim 1, said method comprising the step of conversion of an intermediate compound of general formula XV:

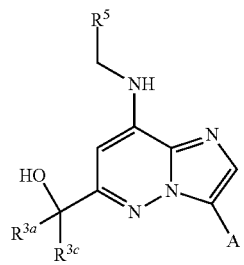

in which $R^{3a}$, $R^{3c}$, $R^5$ and A are as defined in claim 1;
to a compound of general formula XI:

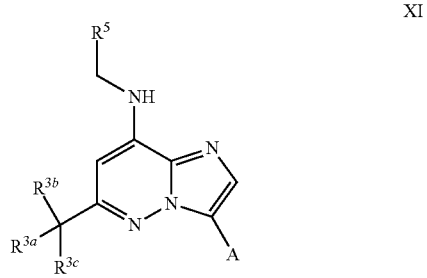

in which $R^{3a}$, $R^{3b}$, $R^{3c}$, $R^5$ and A are as defined in claim 1.

15. A pharmaceutical composition comprising a compound according to claim 1, or a stereoisomer, a tautomer, an N-oxide, a hydrate, a solvate, or a pharmaceutically acceptable salt thereof, or a mixture of same, and a pharmaceutically acceptable diluent or carrier.

16. A pharmaceutical combination comprising:
one or more compounds according to claim 1, or a stereoisomer, a tautomer, an N-oxide, a hydrate, a solvate, or a pharmaceutically acceptable salt thereof, or a mixture of same;
and
one or more agents selected from: a taxane, Docetaxel, Paclitaxel, or Taxol; an epothilone, Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, Flutamide, Cyproterone acetate, or Bicalutamide; Bortezomib; a platinum derivative, Cisplatin, or Carboplatin; Chlorambucil; Methotrexate; and Rituximab.

* * * * *